(12) United States Patent
Mjalli et al.

(10) Patent No.: US 7,582,673 B2
(45) Date of Patent: Sep. 1, 2009

(54) BISSULFONAMIDE COMPOUNDS AS AGONISTS OF GALR1, COMPOSITIONS, AND METHODS OF USE

(75) Inventors: Adnan M. M. Mjalli, Oak Ridge, NC (US); Bapu Gaddam, Greensboro, NC (US); Mohan Rao, Greensboro, NC (US); Muralidhar Bondlela, Greensboro, NC (US); Ramesh Gopalaswamy, Jamestown, NC (US); Robert C. Andrews, Jamestown, NC (US); Stephen Davis, Durham, NC (US); Suvi Simila, Austin, TX (US); Tan Ren, High Point, NC (US)

(73) Assignee: High Point Pharmaceuticals, LLC, High Point, NC (US)

( * ) Notice: Subject to any disclaimer, the term of this patent is extended or adjusted under 35 U.S.C. 154(b) by 309 days.

(21) Appl. No.: 11/255,000

(22) Filed: Oct. 20, 2005

(65) Prior Publication Data

US 2006/0106089 A1    May 18, 2006

Related U.S. Application Data

(60) Provisional application No. 60/670,752, filed on Apr. 13, 2005, provisional application No. 60/620,699, filed on Oct. 21, 2004.

(51) Int. Cl.
*A61K 31/381* (2006.01)
*A61K 31/18* (2006.01)
*C07D 333/66* (2006.01)
*C07C 311/21* (2006.01)

(52) U.S. Cl. .................. 514/443; 514/602; 549/55; 564/86

(58) Field of Classification Search .............. 514/443, 514/602; 564/86; 549/55
See application file for complete search history.

(56) References Cited

U.S. PATENT DOCUMENTS

| | | | |
|---|---|---|---|
| 2,258,162 A | 10/1941 | Northey et al. |
| 3,546,181 A | 12/1970 | Arnold et al. |
| 4,179,466 A | 12/1979 | Bollinger et al. |
| 4,342,875 A | 8/1982 | Gough et al. |
| 4,577,042 A | 3/1986 | Collins et al. |
| 5,250,549 A | 10/1993 | Yoshino et al. |
| 5,397,501 A | 3/1995 | Coope et al. |
| 5,750,366 A | 5/1998 | Sealfon |
| 5,780,483 A | 7/1998 | Widdowson et al. |
| 5,972,624 A | 10/1999 | Smith et al. |
| 6,262,113 B1 | 7/2001 | Widdowson et al. |
| 6,287,788 B1 | 9/2001 | Bard et al. |
| 6,287,855 B1 | 9/2001 | Tan et al. |
| 6,300,325 B1 | 10/2001 | Widdowson et al. |
| 6,329,197 B2 | 12/2001 | Bard et al. |
| 6,337,206 B1 | 1/2002 | Tan et al. |
| 6,368,812 B1 | 4/2002 | Bard et al. |
| 6,399,617 B1 | 6/2002 | Caldirola et al. |
| 6,407,136 B1 | 6/2002 | Scott et al. |
| 6,447,996 B1 | 9/2002 | Ortoli et al. |
| 6,498,156 B2 | 12/2002 | Glombik et al. |
| 6,511,827 B1 | 1/2003 | Howard et al. |
| 6,747,060 B2 | 8/2004 | Saar et al. |
| 7,064,181 B1 | 6/2006 | Ohtaki et al. |
| 2001/0016337 A1 | 8/2001 | Elshourbagy et al. |
| 2003/0009777 A1 | 1/2003 | Wynick et al. |
| 2003/0078271 A1 | 4/2003 | Blackburn et al. |
| 2003/0130318 A1 | 7/2003 | Barf et al. |
| 2003/0149019 A1 | 8/2003 | Bremberg et al. |
| 2003/0158202 A1 | 8/2003 | Caldirola et al. |
| 2003/0166663 A1 | 9/2003 | Caldirola et al. |
| 2003/0211493 A1 | 11/2003 | Baughn et al. |
| 2004/0136984 A1 | 7/2004 | Bayne et al. |
| 2004/0242583 A1 | 12/2004 | Petry et al. |
| 2005/0038248 A1 | 2/2005 | Henderson et al. |
| 2005/0090485 A1 | 4/2005 | Bromidge et al. |
| 2005/0154023 A1 | 7/2005 | Spinks et al. |
| 2006/0015954 A1 | 1/2006 | Aparicio et al. |
| 2006/0177853 A1 | 8/2006 | Bartfai et al. |
| 2007/0037988 A9 | 2/2007 | Gallop et al. |

FOREIGN PATENT DOCUMENTS

| | | |
|---|---|---|
| DE | 195 33 644 | 12/1995 |
| EP | 0 514 361 | 5/1992 |
| WO | WO 92-15015 | 9/1992 |
| WO | WO 92-15681 | 9/1992 |
| WO | WO 96-25157 | 8/1996 |

(Continued)

OTHER PUBLICATIONS

Anouar et al., "Both inducible and Costitutive Activator Protein-1-Like Transcription Factors are used for Transcriptional Activation on the Galanin Gene by Different First and Second Messenger", Molecular Pharmacology, vol. 56, pp. 162-169, (1999).

(Continued)

*Primary Examiner*—Rei-Tsang Shiao
*Assistant Examiner*—Joseph R Kosack
(74) *Attorney, Agent, or Firm*—Kilpatrick Stockton LLP

(57) ABSTRACT

Embodiments of the present invention provide bissulfonamide compounds that are agonists of GalR1. The present invention further provides compositions comprising bissulfonamide compounds that are agonists of GalR1, and methods of use of such compounds and compositions.

53 Claims, No Drawings

FOREIGN PATENT DOCUMENTS

| | | |
|---|---|---|
| WO | WO 97-46681 | 12/1997 |
| WO | WO 98-03059 | 1/1998 |
| WO | WO 00-50563 | 8/2000 |
| WO | WO 00-76495 | 12/2000 |
| WO | WO 00-76501 | 12/2000 |
| WO | WO 01-05398 | 1/2001 |
| WO | WO 01-19788 | 3/2001 |
| WO | WO 01-27273 | 4/2001 |
| WO | WO 01-28537 | 4/2001 |
| WO | WO 01-64643 | 9/2001 |
| WO | WO 01-79237 | 10/2001 |
| WO | WO 01-85791 | 11/2001 |
| WO | WO 01-90090 | 11/2001 |
| WO | WO 01-90092 | 11/2001 |
| WO | WO 01-90093 | 11/2001 |
| WO | WO 01-90094 | 11/2001 |
| WO | WO 02-096934 | 12/2002 |
| WO | WO 2004-028552 | 4/2004 |
| WO | WO 2005-004810 | 1/2005 |
| WO | WO 2005-039502 | 5/2005 |
| WO | WO 2005-066122 | 7/2005 |
| WO | WO 2005-080427 | 9/2005 |
| WO | WO 2006-004841 | 1/2006 |
| WO | WO 2006-015700 | 2/2006 |
| WO | WO 2006-015701 | 2/2006 |
| WO | WO 2006-071469 | 7/2006 |
| WO | WO 2006-074128 | 7/2006 |

OTHER PUBLICATIONS

Bedecs et al., "Galanin—10 Years with a Neuroendocrine Peptide", International Journal of Biochemistry & Cell Biology, vol. 27, pp. 337-349, (1995).

Bennett et al., "A peripheral mononeuropathy in rat that produces disorders of pain sensation like those seen in man", Pain, vol. 33, pp. 87-107, (1988).

Berger et al., "Galanin and galanin Receptors in Human Gliomas", Acta Neuropathol, vol. 105, pp. 555-560, (2003).

Branchek et al., "Galanin receptor subtypes", Trends in Pharmacological Sciences, vol. 21, pp. 109-117, (2000).

Church et al., "Molecular Modelling and site-directed Mutagenesis of human GALR1 galanin receptor defines determinants of receptor subtype specificity", Protein Engineering, vol. 15, pp. 313-323, (2002).

Fitzgerald et al., "Pharmacological and Biochemical Characterization of a Recombinant Human Galanin GALR1 Receptor: Agonist Character of Chimeric Galanin Pepties", The Journal of Pharmacology and Experimental Therapeutics, vol. 287, pp. 448-456, (1998).

Grass et al., "Flexor Reflex Excitability in Mice Lacking Galanin Receptor Galanin-R1", Neuroscience Letters, vol. 345, pp. 153-156, (2003).

Haberman et al., "Attenuation of Seizures and Neuronal Death by Adenoassociated Virus Vector Galanin Expression and Secretion", Nature Medicine, vol. 9, pp. 1076-1080, (2003).

Henson et al., "Galanin receptor 1 has anti-proliferative effects in oral squamous cell carcinoma", The Journal of biological chemistry, vol. 280, pp. 22564-22571, (2005).

Heuillet et al., "The human galanin receptor: ligand-binding and functional characteristics in the Bowes melanoma cell line" European Journal of Pharmacology, Molecular Pharmacology Section, vol. 269, pp. 139-147, (1994).

Hohmann et al., "Obesity and Endocrine Dysfunction in Mice with Deletions of Both Neuropeptide Y and Galanin", Molecular and Cellular Biology, vol. 24, pp. 2978-2985, (2004).

Hua et al., "Galanin acts at GalR1 receptors in spinal antinociception: Synergy with morphine and AP-5" Journal of Pharmacology and Experimental Therapeutics, vol. 308, pp. 574-582, (2004).

Kask et al, "Galanin- a neuropeptide with inhibitory actions", Cellular and Molecular Neurobiology, vol. 15, pp. 653-673, (1995).

Kask et al., "Galanin receptors: involvement in feeding, pain, depression and Alzheimer's disease", Life Sciences, vol. 60, pp. 1523-1533, (1997).

Liu et al., "Receptor subtype-specific pronociceptive and analgesic actions of galanin in the spinal cord: selective actions via GalR1 and GalR2 receptors", Proceedings of the National Academy of Sciences, vol. 98, pp. 9960-9964, (2001).

Liu et al, "The participation of galanin in pain processing at the spinal level", Trends in Pharmacological Sciences, vol. 23, pp. 468-474, (2002).

Ma et al., "Differential expression of galanin immunoreactivities in the primary sensory neurons following partial and complete sciatic nerve injuries", Neuroscience, vol. 79, pp. 1183-1195, (1997).

McQuay et al., "Anticonvulsant Drugs For the Management of Pain: A Systematic Review", British Medical Journal, vol. 311, pp. 1047-1052, (1995).

Saar et al., "Anticonvulsant Activity of a Nonpeptide Galanin Receptor Agonist", Proceedings of the National Academy of Sciences, vol. 99, pp. 7136-7141, (2002).

Wang et al., "Molecular Cloning and Pharmacological Characterization of a New Galanin Receptor Subtype", Molecular Pharmacology, vol. 52, pp. 337-343, (1997).

Waters et al., "Distibution of galanin-1,-2 and -3 receptor messenger RNAs in central and peripheral rat tissues", Neuroscience, vol. 95, pp. 265-271, (2000).

Wood et al., "Galanin receptors and actions", Drugs of the Future, vol. 29, pp. 149-161, (2004).

Yuan et al., "Gastric Effects of Galanin and Its Interaction with Leptin on Brainstem Neuronal Activity", The Journal of Pharmacology and Experimental Therapeutics, vol. 301, pp. 488-493, (2002).

Zachariou et al., "The neuropeptide galanin modulates behavioral and neurochemical signs of opiate withdrawal", Proceedings of the National Academy of Sciences, vol. 100, pp. 9028-9033, (2003).

Adams et al., "Quinone Imides. VII. 1.2- and 2.6-Naphthoquinone Disulfonimides" Journal of the American Chemical Society, vol. 73, pp. 2219-2221, (1951).

Adams et al., Quinone Imides. VIII. Synthesis and Reactions of o-Quinone Diimides Journal of the American Chemical Society, vol. 73, pp. 5687-5691. (1951).

Adams et al., "Quinone Imides. XLIII. The Reactions of o-Quinonedibenzenesulfonimides" Journal of the American Chemical Society, vol. 79, pp. 417-419, (1957).

Bell et al., "Derivatives of Naphthalen-2,7-Diamine" Journal of the Chemical Society, vol. 1962, pp. 4254-4257. (1962).

Friedrichsen et al., "Reaktionen von $N,N'$-Diarylsulfonyl-$o$-benzochinon-diiminen mit Fulvenen. 12)" Liebigs Annalen Der Chemie, vol. 1978, pp. 1146-1160, (1978).

International Search Report for related PCT application PCT/US2005/037932 mailed Apr. 6, 2006.

Katoh et al., "Studies Toward the Total Synthesis of Gch 202596, an Antagoinist of the Galanin Receptor Subtype GalR1: Synthesis of Geodin, the Spirocoumaranone Subunit of Sch 202596" Tetrahedron Letters, vol. 41, pp. 465-469, (2000).

Massacret et al., "Palladium (0)-Catalyzed Asymmetric Synthesis of 1,2,3,4- Tetrahydro -2 -vinylquinoxalines" European Journal of Organic Chemistry, vol. 1999, pp. 129-134, (1999).

Saunders et al., "Ring-Substituted derivatives fo 5,6,11,12-Tetrahyrodibenzo[$b,f$][1,4]-Diazocine" Journal of the Chemical Society, vol. 1970, pp. 1161-1165, (1970).

Wooley et al., "Relationship of Chemical Structure to Antibacterial Activity Among Analogues of Dimethyldiaminobenzene" Journal of Biological Chemistry, vol. 194, pp. 729-746, (1952).

Woolley et al., "Synthesis of Derivatives of 1,2-Dichloro-4-Benzenesulfonamido-5-Nitrobenzene and Their Use in the Chemotherapy of Spontaneous Cancers" Canadian Journal of Chemistry, vol. 43, pp. 1454-1459. (1965).

International Preliminary Report for related PCT application US2005/037932 mailed May 3, 2007.

BISSULFONAMIDE COMPOUNDS AS AGONISTS OF GALR1, COMPOSITIONS, AND METHODS OF USE

STATEMENT OF RELATED APPLICATIONS

The present application claims the benefit of priority of U.S. Provisional Application Ser. No. 60/620,699, filed Oct. 21, 2004, and U.S. Provisional Application Ser. No. 60/670,752, filed Apr. 13, 2005.

FIELD OF THE INVENTION

The present invention relates to bissulfonamide compounds as agonists of GalR1, and compositions, and methods of use of such compounds and compositions.

BACKGROUND

Galanin is a 30 amino acid neuropeptide in humans (29 amino acids in rodents) that is widely distributed in tissues including brain, spinal cord, and gut (1). Galanin regulates numerous processes including nociception, nerve regeneration, feeding, memory, neuroendocrine release, gut secretion and contractility (2,3). Three galanin receptor subtypes (GalR1, GalR2, and GalR3) have been cloned and belong to the superfamily of G protein-coupled 7-transmembrane receptors (4,5). These receptors have been shown to couple to various G-protein systems that modulate second messenger activity. Galanin stimulation of GalR1 is sensitive to pertussis toxin, consistent with coupling to Gi/o-type G proteins (6).

All three galanin receptor subtypes are expressed in the dorsal root ganglia (DRG) and the spinal cord (7). The anatomical location of both galanin and its receptors, and the upregulation of galanin in response to nerve damage suggests that the galanin-GalR pathway may play a key role in the regulation of spinal nociceptive transmission (8-10). Intrathecal dosing of galanin enhanced the spinal anti-nociceptive response to morphine and reduced the physical signs of opiate withdrawal (11, 12). GalR1 may be a key galanin receptor for anti-nociceptive transmission. Intrathecal administration of a galanin peptide analog with GalR1 selectivity improved pain threshold in a neuropathic pain model (13, 14).

In recent studies, the expression, mitogenic function, and signaling mechanism of GalR1 were investigated in normal and malignant oral epithelial cells. Upon competitive inhibition of GalR1, proliferation was upregulated in immortalized and malignant keratinocytes. Studies also demonstrated that GalR1 inhibits proliferation in immortalized and malignant keratinocytes by inactivating the MAPK pathway. (15)

SUMMARY OF INVENTION

The present invention provides compounds of Formula (I) as described herein, wherein the compounds of Formula (I) are GalR1 agonists. In another embodiment, the present invention also provides methods for the preparation of compounds of Formula (I).

The present invention also provides pharmaceutical compositions comprising compounds of Formula (I). In another embodiment, the present invention provides methods for the preparation of pharmaceutical compositions comprising the compounds of Formula (I). The pharmaceutical compositions may comprise pharmaceutically acceptable carriers, excipients, and/or diluents.

In another embodiment, the present invention provides methods for the use of compounds of Formula (I) and for the use of pharmaceutical compositions comprising compounds of Formula (I). The compounds and pharmaceutical compositions of the present invention may be used for the treatment of human or animal disorders.

The compounds of Formula (I) and pharmaceutical compositions comprising a compound of Formula (I) may provide a number of advantages when used for treating human or animal disorders. In one embodiment, the compounds and pharmaceutical compositions of the present invention may provide a variety of treatment options. As small molecule therapeutics, example embodiments of the compounds and pharmaceutical compositions of the present invention may be administered orally, topically, or parentally. Also, the compounds and pharmaceutical compositions of the present invention may comprise a primary therapeutic or may be used as an adjunct to other therapeutics.

In another embodiment, the present invention provides a pharmaceutical composition comprising a compound of Formula (I), wherein the compound of Formula (I) is a GalR1 agonist and the compound of Formula (I) is present in an amount sufficient to increase activity of a GalR1 receptor. In another embodiment, the pharmaceutical composition comprises a compound of Formula (I), wherein the compound of Formula (I) is a GalR1 agonist and the compound of Formula (I) is present in an amount sufficient to stimulate GalR1 in a subject.

In another embodiment, the present invention provides a method comprising: administering to a subject having a disorder ameliorated by the activation of a GalR1 receptor, a pharmaceutical composition comprising a compound of Formula (I) in an amount sufficient to increase activity of GalR1 in a subject. For example, the compounds and pharmaceutical compositions of the present invention may be useful in treating neuropathic pain or cancer. Further, at doses for which an analgesic effect may be observed, the compounds of the present invention may be capable of binding to at least one peripheral GalR1 while substantially unable to cross the blood-brain barrier. Partial or complete exclusion of the compounds of the present invention from the brain may reduce the risk or severity of one or more centrally mediated side effects associated with the compounds or pharmaceutical compositions.

Additional features of the present invention will be described hereinafter. It is to be understood that the invention is not limited in its application to the details set forth in the foregoing or following description but is capable of other embodiments and of being practiced or carried out in various ways.

DETAILED DESCRIPTION

Throughout this application, various publications are referenced. Full citations for these publications may be found immediately preceding the claims.

Pain is a sensation and a perception that is comprised of a complex series of mechanisms. In its most simple construction, pain is a signal from the firing of nociception, touch and pressure receptors in the periphery that is transmitted to the spinal cord and finally to lower and higher centers of the brain. However, this signal can be modified in a multitude of ways at each level of the pain pathway. (16).

Physiological pain is an important protective mechanism designed to warn of danger from potentially injurious stimuli from the external environment. The system operates through a specific set of primary sensory neurons and is exclusively activated by noxious stimuli via peripherally transducing mechanisms (16). These sensory fibres are known as nociceptors and are characterized by smaller diameter axons with slow conduction velocities. Nociceptors encode the intensity, duration, and quality of noxious stimulus. Nociceptors also encode the location of the stimulus by virtue of their topographically organized projection to the spinal cord. The nociceptors are found on nociceptive nerve fibres of which there are two main types, A-delta fibres (myelinated) and C fibres (non-myelinated). The activity generated by nociceptor input is transferred after complex processing in the dorsal horn, either directly or via brain stem relay nuclei to the ventrobasal thalamus and then on to the cortex where the sensation of pain is generated.

There are primarily three types of pain. Acute pain, termed nociception, is the instantaneous onset of a painful sensation in response to a noxious stimulus. It is considered to be adaptive because it can prevent an organism from damaging itself. For example, removing a hand from a hot stove as soon as pain is felt will prevent serious burns.

The second type of pain is persistent pain. Unlike acute pain, it usually has a delayed onset but can last for hours to days. It is predominately considered adaptive because the occurrence of persistent pain following injury can prevent further damage to the tissue. For example, the pain associated with a sprained ankle will prevent the patient from using the foot thereby preventing further trauma and aiding healing.

The final category of pain is chronic pain. It has a delayed onset and can last for months to years. In contrast to acute and persistent pain, chronic pain is considered maladaptive and is associated with conditions such as arthritis, nerve injury, AIDS and diabetes.

Chronic or neuropathic pain occurs in a variety of forms including spontaneous pain (painful sensation without an external stimulus), allodynia (painful sensation in response to a normally innocuous stimulus) and hyperalgesia (strong painful sensation to a mildly painful stimulus). It may be this diversity of symptoms that has made this condition difficult to treat clinically. In fact, current treatments are predominately off label use of antidepressants and anticonvulsants. Both antidepressants and anticonvulsants may present problems for a patient.

Tricyclic antidepressants have the longest history of use in the treatment of neuropathic pain. Such drugs typically target the serotonergic and noradrenergic systems and increase the available extracellular levels of both serotonin and norepinephrine. It has been proposed that the postsynaptic activation of alpha$_2$-adrenoceptors by norepinephrine may be the mechanism through which these compounds alleviate neuropathic pain. Since antidepressants may readily cross the blood-brain barrier, their ability to increase the levels of serotonin and norepinephrine may cause the undesired activation of other receptors leading to the high risk of centrally mediated side effects. Side effects of antidepressants may range from mild but irritating symptoms such as dry mouth and sedation to severe life threatening side effects such as postural hypotension and cardiac arrythmias. The elderly, who represent a large number of neuropathic patients, can be particularly vulnerable to the more serious side effects of antidepressants.

The effectiveness of anticonvulsants in the treatment of various pain states, including neuropathic pain, has recently been evaluated (17). Similar to antidepressants, side effects may frequently occur with these medications.

Due to the common occurrence of side effects with antidepressants and anticonvulsants and the limitations these side effects may place on the use of these compounds, there is a need for a treatment for neuropathic pain that may avoid centrally mediated side effects.

In one aspect, the present invention provides compounds of Formula (I): $Ar_2—SO_2NH—Ar_1—NHSO_2—Ar_3$(I), pharmceutically acceptable salts, or prodrugs thereof, wherein the compound of Formula (I) is a GalR1 agonist.

$Ar_1$ comprises an arylene, heteroarylene, fused cycloalkylarylene, fused heterocyclylarylene, fused cycloalkylheteroarylene, or fused heterocyclylheteroarylene group optionally independently substituted 1 to 4 times. In an embodiment, $Ar_1$ comprises an arylene group optionally independently substituted 1 to 4 times. In various embodiments, the substituents of $Ar_1$ may comprise:

a) hydrogen;
b) -halo;
c) -cyano;
d) -nitro;
e) -perhaloalkyl;
f) -alkyl;
g) -aryl;
h) -heteroaryl;
i) -cycloalkyl;
j) -L-aryl;
k) -L-arylene-aryl;
l) -L-arylene-alkyl;
m) -Q-alkyl;
n) -Q-aryl;
o) -Q-alkylene-aryl;
p) -Q-arylene-alkyl;
q) -L-Q-alkylene-aryl;
r) -arylene-Q-alkyl;
s) -L-Q-alkyl;
t) -L-Q-aryl;
u) -L-Q-heteroaryl;
v) -L-Q-cycloalkyl;
w) -L-Q-arylene-alkyl;
x) -$D_4$-alkylene-$NR_1R_2$;
y) -$D_4$-$NR_1R_2$;
z) -$D_4$-alkyl; or
aa) -$D_4$-H;
    wherein
        $D_4$ comprises a direct bond, —$CH_2$—, —O—, —N($R_4$)—, —C(O)—, —CON($R_4$)—, —N($R_4$)C(O)—, —N($R_4$)CON($R_{4'}$)—, —N($R_4$)C(O)O—, —OC(O)N($R_4$)—, —N($R_4$)$SO_2$—, —$SO_2$N($R_4$)—, —C(O)—O—, —O—C(O)—, —S—, —S(O)—, —S(O)$_2$—, —N($R_4$)$SO_2$N($R_{4'}$)—, or —N=N—;
        wherein
            $R_4$ and $R_{4'}$ independently comprise -hydrogen, -alkyl, -aryl, -arylene-alkyl, or -alkylene-aryl;
        $R_1$ and $R_2$ independently comprise hydrogen, alkyl, or aryl, wherein $R_1$ and $R_2$ may be taken together to form a ring having the formula —$(CH_2)_o$-$Z_4$-$(CH_2)_p$— bonded to the nitrogen atom to which $R_1$ and $R_2$ are attached,
        wherein
            o and p are, independently, 1, 2, 3, or 4 and the o+p is less than or equal to 6,
            $Z_4$ comprises a direct bond, —$CH_2$—, —C(O)—, —O—, —N(H)—, —S—, —S(O)—, —S(O)$_2$—, —CON(H)—, —NHC(O)—, —NHC(O)N(H)—, —NH($SO_2$)—, —S(O)$_2$N(H)—, —(O)CO—, —NHS(O)$_2$NH—, —OC(O)—, —N($R_{31}$)—, —N(C(O)$R_{31}$)—, —N(C(O)NH$R_{31}$)—, —N(C(O)N$R_{31}R_{32}$)—, —N(S(O)$_2$NH$R_{31}$)—, —N($SO_2R_{31}$)—, or —N(C(O)O$R_{31}$)—;

wherein
R$_{31}$ and R$_{32}$ independently comprise -hydrogen, -alkyl, -aryl, or -alkylene-aryl;
L comprises a direct bond, -alkylene, -alkenylene, or -alkynylene; and
Q comprises a direct bond, —CH$_2$—, —O—, or —S—.

In another embodiment, the —NHSO$_2$—Ar$_2$ and the —NHSO$_2$—Ar$_3$ groups are located on adjacent atoms in the Ar$_1$ ring. In a further embodiment, Ar$_1$ is

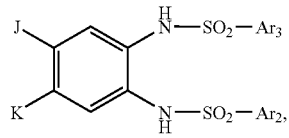

wherein J and K independently comprise
a) hydrogen;
b) -halo;
c) -cyano;
d) -nitro;
e) -perhaloalkyl;
f) -alkyl;
g) -aryl;
h) -heteroaryl;
i) -cycloalkyl;
j) -L-aryl;
k) -L-arylene-aryl;
l) -L-arylene-alkyl;
m) -Q-alkyl;
n) -Q-aryl;
o) -Q-alkylene-aryl;
p) -Q-arylene-alkyl;
q) -L-Q-alkylene-aryl;
r) -arylene-Q-alkyl;
s) -L-Q-alkyl;
t) -L-Q-aryl;
u) -L-Q-heteroaryl;
v) -L-Q-cycloalkyl;
w) -L-Q-arylene-alkyl;
x) -D$_4$-alkylene-NR$_1$R$_2$;
y) -D$_4$-NR$_1$R$_2$;
z) -D$_4$-alkyl; or
aa) -D$_4$-H;
wherein
D$_4$ comprises a direct bond, —CH$_2$—, —O—, —N(R$_4$)—, —C(O)—, —CON(R$_4$)—, —N(R$_4$)C(O)—, —N(R$_4$)CON(R$_{4'}$)—, —N(R$_4$)C(O)O—, —OC(O)N(R$_4$)—, —N(R$_4$)SO$_2$—, —SO$_2$N(R$_4$)—, —C(O)—O—, —O—C(O)—, —S—, —S(O)—, —S(O)$_2$—, —N(R$_4$)SO$_2$N(R$_{4'}$)—, or —N=N—;
wherein
R$_4$ and R$_{4'}$ independently comprise -hydrogen, -alkyl, -aryl, -arylene-alkyl, or -alkylene-aryl;
R$_1$ and R$_2$ independently comprise hydrogen, alkyl, or aryl, wherein R$_1$ and R$_2$ may be taken together to form a ring having the formula —(CH$_2$)$_o$-Z$_4$-(CH$_2$)$_p$— bonded to the nitrogen atom to which R$_1$ and R$_2$ are attached,
wherein
o and p are, independently, 1, 2, 3, or 4 and the o+p is less than or equal to 6,
Z$_4$ comprises a direct bond, —CH$_2$—, —C(O)—, —O—, —N(H)—, —S—, —S(O)—, —S(O)$_2$—, —CON(H)—, —NHC(O)—, —NHC(O)N(H)—, —NH(SO$_2$)—, —S(O)$_2$N(H)—, —(O)CO—, —NHS(O)$_2$NH—, —OC(O)—, —N(R$_{31}$)—, —N(C(O)R$_{31}$)—, —N(C(O)NHR$_{31}$)—, —N(C(O)NR$_{31}$R$_{32}$)—, —N(S(O)$_2$NHR$_{31}$)—, —N(SO$_2$R$_{31}$)—, or —N(C(O)OR$_{31}$)—;
wherein
R$_{31}$ and R$_{32}$ independently comprise -hydrogen, -alkyl, -aryl, or -alkylene-aryl;
L comprises a direct bond, -alkylene, -alkenylene, or -alkynylene; and
Q comprises a direct bond, —CH$_2$—, —O—, or —S—.

In a further embodiment, J and K independently comprise hydrogen, halo, haloalkyl, alkoxy, haloalkoxy, cyano, carboxy, amide, -D$_4$-alkyl, -D$_4$-alkylene-NR$_1$R$_2$, -D$_4$-NR$_1$R$_2$, -D$_4$-alkyl; -D$_4$-H, wherein D$_4$ comprises a —C(O)—, —CON(R$_4$)—, —SO$_2$N(R$_4$)—, —C(O)—O—, wherein R$_4$ comprises -hydrogen, -alkyl, -aryl, -arylene-alkyl, or -alkylene-aryl;
wherein
R$_1$ and R$_2$ independently comprise hydrogen, alkyl, or aryl, wherein R$_1$ and R$_2$ may be taken together to form a ring having the formula —(CH$_2$)$_o$-Z$_4$-(CH$_2$)$_p$— bonded to the nitrogen atom to which R$_1$ and R$_2$ are attached,
wherein
o and p are, independently, 1, 2, 3, or 4 and the o+p is less than or equal to 6,
Z$_4$ comprises a direct bond, —CH$_2$—, —C(O)—, —O—, —N(H)—, —S—, —S(O)—, —S(O)$_2$—, —CON(H)—, —NHC(O)—, —NHC(O)N(H)—, —NH(SO$_2$)—, —S(O)$_2$N(H)—, —(O)CO—, —NHS(O)$_2$NH—, —OC(O)—, —N(R$_{31}$)—, —N(C(O)R$_{31}$)—, —N(C(O)NHR$_{31}$)—, —N(C(O)NR$_{31}$R$_{32}$)—, —N(S(O)$_2$NHR$_{31}$)—, —N(SO$_2$R$_{31}$)—, or —N(C(O)OR$_{31}$)—;
wherein
R$_{31}$ and R$_{32}$ independently comprise -hydrogen, -alkyl, -aryl, or -alkylene-aryl,
wherein at least one of J and K is a group other than hydrogen.

In a further embodiment, Ar$_1$ is

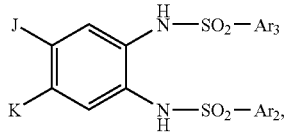

wherein J and K are defined as above, and wherein Ar$_2$ and Ar$_3$ are unsubstituted benzothiophene group.

In another embodiment, Ar$_1$ comprises an unsubstituted phenylene group. In another embodiment, Ar$_1$ comprises an unsubstituted phenylene group and the —NHSO$_2$—Ar$_2$ and the —NHSO$_2$—Ar$_3$ substituent groups are located on adjacent carbon atoms in the Ar$_1$ ring.

In another embodiment, the compound of Formula (I) is not C2 symmetric about a plane dividing Ar$_1$ with Ar$_2$ and Ar$_3$ on opposites sides of the plane.

Ar$_2$ and Ar$_3$ independently comprise an aryl, heteroaryl, fused cycloalkylaryl, fused cycloalkylheteroaryl, fused heterocyclylaryl, or fused heterocyclylheteroaryl group optionally independently substituted 1 to 5 times, wherein at least one of Ar$_2$ and Ar$_3$ comprise an oxygen atom or sulfur atom vicinal or geminal to the point of attachment to the —NHSO$_2$— group. In various embodiments, the substituents of Ar$_2$ and Ar$_3$ may independently comprise:
a) -hydrogen;
b) -halo;
c) -cyano;
d) -nitro;
e) -alkyl;
f) -aryl;
g) -cycloalkyl;
h) -heterocyclyl;
i) -alkylene-cycloalkyl;
j) -perhaloalkyl;
k) heteroaryl;
l) -alkylene-aryl;
m) -D$_1$-H;
n) -D$_1$-R$_3$;
o) -D$_1$-alkyl;
p) -D$_1$-aryl;
q) -D$_1$-perhaloalkyl;
r) -D$_1$-alkylene-R$_3$;
s) -D$_1$-alkylene-aryl;
t) -D$_1$-alkylene-D$_2$-R$_3$;
u) -D$_1$-cycloalkyl;
v) -D$_1$-heterocyclyl;
w) -D$_1$-aryl;
x) -D$_1$-heteroaryl;
y) -D$_1$-arylene-D$_2$-R$_3$;
z) -D$_1$-heteroarylene-D$_2$-R$_3$;
aa) -D$_1$-alkylene-heteroaryl;
bb) -D$_1$-alkylene-heterocyclyl;
cc) -D$_1$-alkylene-aryl;
dd) -D$_1$-alkylene-arylene-D$_2$-R$_3$;
ee) -D$_1$-alkylene-heteroarylene-D$_2$-R$_3$;
ff) -D$_1$-alkylene-NR$_5$R$_6$;
gg) -D$_1$-arylene-NR$_5$R$_6$; or
hh) -acid isostere;
   wherein
   D$_1$ comprises a direct bond, —CH$_2$—, —O—, —N(R$_7$)—, —C(O)—, —CON(R$_7$)—, —N(R$_7$)C(O)—, —N(R$_7$)CON(R$_8$)—, —N(R$_7$)C(O)O—, —OC(O)N(R$_7$)—, —N(R$_7$)SO$_2$—, —SO$_2$N(R$_7$)—, —C(O)—O—, —O—C(O)—, —S—, —S(O)—, —S(O)$_2$—, —N(R$_7$)SO$_2$N(R$_8$)—, or —N=N—;
     wherein
     R$_7$ and R$_8$ independently comprise -hydrogen, -alkyl, -aryl, -arylene-alkyl, -alkylene-aryl, or -alkylene-arylene-alkyl;
   R$_3$ comprises: -hydrogen, -alkyl, -aryl, -heterocyclyl, or -heteroaryl; and
   R$_5$ and R$_6$ independently comprise hydrogen, alkyl, or aryl, wherein R$_5$ and R$_6$ may be taken together to form a ring having the formula —(CH$_2$)$_o$-Z$_1$-(CH$_2$)$_p$— bonded to the nitrogen atom to which R$_5$ and R$_6$ are attached,
     wherein
     o and p are, independently, 1, 2, 3, or 4 and the o+p is less than or equal to 6,
     Z$_1$ comprises a direct bond, —CH$_2$—, —C(O)—, —O—, —N(H)—, —S—, —S(O)—, —S(O)$_2$—, —CON(H)—, —NHC(O)—, —NHC(O)N(H)—, —NH(SO$_2$)—, —S(O)$_2$N(H)—, —(O)CO—, —NHS(O)$_2$NH—, —OC(O)—, —N(R$_9$)—, —N(C(O)R$_9$)—, —N(C(O)NHR$_9$)—, —N(C(O)NR$_9$R$_{10}$)—, —N(S(O)$_2$NHR$_9$)—, —N(SO$_2$R$_9$)—, or —N(C(O)OR$_9$)—;
     wherein
     R$_9$ and R$_{10}$ independently comprise -hydrogen, -alkyl, -aryl, or -alkylene-aryl;
   D$_2$ comprises -alkylene-, -alkenylene-, -alkylene-S—, —S-alkylene-, -alkylene-O—, —O-alkylene-, -alkylene-S(O)$_2$—, —S(O)$_2$-alkylene, —O—, —N(R$_{11}$)—, —C(O)—, —CON(R$_{11}$)—, —N(R$_{11}$)C(O)—, —N(R$_{11}$)CON(R$_{12}$)—, —N(R$_{11}$)C(O)O—, —OC(O)N(R$_{11}$)—, —N(R$_{11}$)SO$_2$—, —SO$_2$N(R$_{11}$)—, —C(O)—O—, —O—C(O)—, —S—, —S(O)—, —S(O)$_2$—, or —N(R$_{11}$)SO$_2$N(R$_{12}$)—,
     wherein
     R$_{11}$ and R$_{12}$ independently comprise: -hydrogen, -alkyl, or -aryl.

In an embodiment, Ar$_2$ and Ar$_3$ independently comprise an aryl, heteroaryl, fused cycloalkylaryl, fused cycloalkylheteroaryl, fused heterocyclylaryl, or fused heterocyclylheteroaryl group optionally independently substituted 1 to 5 times, wherein at least one of Ar$_2$ and Ar$_3$ comprise an oxygen atom or sulfur atom vicinal or geminal to the point of attachment to the —NHSO$_2$— group and Ar$_2$ and Ar$_3$ are different.

In another embodiment, Ar$_2$ and Ar$_3$ independently comprise an aryl, heteroaryl, or fused heterocyclylheteroaryl group optionally independently substituted 1 to 5 times, wherein at least one of Ar$_2$ and Ar$_3$ comprise an oxygen atom or sulfur atom vicinal or geminal to the point of attachment to the —NHSO$_2$— group.

In another embodiment, Ar$_2$ and Ar$_3$ independently comprise an aryl, heteroaryl, or fused heterocyclylheteroaryl group optionally independently substituted 1 to 5 times, wherein at least one of Ar$_2$ and Ar$_3$ comprise an oxygen atom or sulfur atom vicinal or geminal to the point of attachment to the —NHSO$_2$— group and wherein Ar$_2$ and Ar$_3$ are different.

In another embodiment, Ar$_2$ and Ar$_3$ independently comprise an optionally substituted or unsubstituted phenyl, benzothiophenyl, benzofuranyl, or 4,5,6,7-tetrahydrothieno[3,2-c]pyridinyl, wherein at least one of Ar$_2$ and Ar$_3$ comprise an oxygen atom or sulfur atom vicinal or geminal to the point of attachment to the —NHSO$_2$— group.

In another embodiment, Ar$_2$ and Ar$_3$ independently comprise an aryl, heteroaryl, fused cycloalkylaryl, fused cycloalkylheteroaryl, fused heterocyclylaryl, or fused heterocyclylheteroaryl group optionally independently substituted 1 to 5 times, wherein at least one of Ar$_2$ and Ar$_3$ comprise either

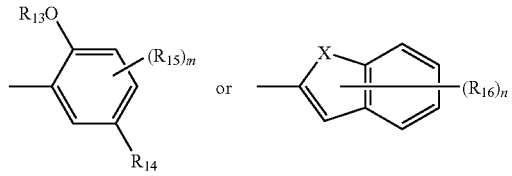

wherein
R$_{13}$ comprises alkyl, alkylene-cycloalkyl, haloalkyl, perhaloalkyl, or cycloalkyl;

$R_{14}$ comprises
  a) -halo;
  b) -cyano;
  c) -nitro;
  d) -perhaloalkyl;
  e) $-D_1-R_{17}$;
  f) $-D_1$-alkyl;
  g) $-D_1$-alkylene-$R_{17}$;
  h) $-D_1$-alkylene-$D_2$-$R_{17}$;
  i) $-D_1$-aryl;
  j) $-D_1$-heteroaryl;
  k) $-D_1$-arylene-$D_2$-$R_{17}$;
  l) $-D_1$-heteroarylene-$D_2$-$R_{17}$;
  m) -D-alkylene-heteroaryl;
  n) -D-alkylene-heterocyclyl;
  o) $-D_1$-alkylene-aryl;
  p) $-D_1$-alkylene-arylene-$D_2$-$R_{17}$;
  q) $-D_1$-alkylene-heteroarylene-$D_2$-$R_{17}$;
  r) $-D_1$-alkylene-$NR_{18}R_{19}$;
  s) $-D_1$-arylene-$NR_{18}R_{19}$; or
  t) -acid isostere;
  wherein
    $D_1$ comprises direct bond, $-S(O)_2-$, $-CON(R_{20})-$, $-SO_2N(R_{20})-$, $-C(O)-O-$, $-S-$, $-S(O)-$;
      wherein $R_{20}$ comprises -hydrogen, -alkyl, -aryl, -heterocyclyl, or -heteroaryl;
    $R_{17}$ comprises: -hydrogen, -alkyl, -aryl, -heterocyclyl, or -heteroaryl;
    $R_{18}$ and $R_{19}$ independently comprise hydrogen, aryl, or alkyl, wherein $R_{18}$ and $R_{19}$ may be taken together to form a ring having the formula $-(CH_2)_o-Z_2-(CH_2)_p-$ bonded to the nitrogen atom to which $R_{18}$ and $R_{19}$ are attached,
      wherein
        o and p are, independently, 1, 2, 3, or 4 and the o+p is less than or equal to 6,
        $Z_2$ comprises a direct bond, $-CH_2-$, $-C(O)-$, $-O-$, $-N(H)-$, $-S-$, $-S(O)-$, $-S(O)_2-$, $-CON(H)-$, $-NHC(O)-$, $-NHC(O)N(H)-$, $-NH(SO_2)-$, $-S(O)_2N(H)-$, $-(O)CO-$, $-NHS(O)_2NH-$, $-OC(O)-$, $-N(R_{20})-$, $-N(C(O)R_{20})-$, $-N(C(O)NHR_{20})-$, $-N(C(O)NR_2OR_{21})-$, $-N(S(O)_2NHR_{20})-$, $-N(SO_2R_{20})-$, or $-N(C(O)OR_{20})-$;
          wherein
            $R_{20}$ and $R_{21}$ independently comprise -hydrogen, -alkyl, -aryl, or -alkylene-aryl;
    $D_2$ comprises -alkylene-, -alkenylene-, -alkylene-S—, —S-alkylene-, -alkylene-O—, —O-alkylene-, -alkylene-S(O)$_2$—, —S(O)$_2$-alkylene, —O—, —N(R$_{22}$)—, —C(O)—, —CON(R$_{22}$)—, —N(R$_{22}$)C(O)—, —N(R$_{22}$)CON(R$_{23}$)—, —N(R$_{22}$)C(O)O—, —OC(O)N(R$_{22}$)—, —N(R$_{22}$)SO$_2$—, —SO$_2$N(R$_{22}$)—, —C(O)—O—, —O—C(O)—, —S—, —S(O)—, —S(O)$_2$—, or —N(R$_{22}$)SO$_2$N(R$_{23}$)—,
      wherein
        $R_{22}$ and $R_{23}$ independently comprise: -hydrogen, -alkyl, or -aryl;

$R_{15}$ and $R_{16}$ independently comprise
  a) -hydrogen;
  b) -halogen;
  c) -cyano;
  d) -alkyl;
  e) -aryl;
  f) -alkylene-aryl;
  g) $-D_3$-H;
  h) $-D_3$-alkyl;
  i) $-D_3$-aryl;
  j) $-D_3$-alkylenearyl;
  k) -Y-alkyl;
  l) -Y-aryl;
  m) -Y-alkylene-aryl;
  n) -Y-alkylene-$NR_{24}R_{25}$; or
  o) -Y-alkylene-W—$R_{26}$;
  wherein
    $D_3$ comprises —O—, —C(O)—O—, —C(O)—NH—, —SO$_2$—, —SO$_2$—NH—, or —C(O)—;
    Y and W independently comprise, —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, or —O—CO—,
    $R_{26}$ comprises aryl, alkyl, alkylene-aryl, alkoxy, and alkoxyaryl;
    $R_{24}$ and $R_{25}$ independently comprise hydrogen, aryl, or alkyl, wherein $R_{24}$ and $R_{25}$ may be taken together to form a ring having the formula $-(CH_2)_o-Z_3-(CH_2)_p-$ bonded to the nitrogen atom to which $R_{24}$ and $R_{25}$ are attached,
      wherein
        o and p are, independently, 1, 2, 3, or 4 and the o+p is less than or equal to 6,
        $Z_3$ comprises a direct bond, —CH$_2$—, —C(O)—, —O—, —N(H)—, —S—, —S(O)—, —S(O)$_2$—, —CON(H)—, —NHC(O)—, —NHC(O)N(H)—, —NH(SO$_2$)—, —S(O)$_2$N(H)—, —(O)CO—, —NHS(O)$_2$NH—, —OC(O)—, —N(R$_{29}$)—, —N(C(O)R$_{29}$)—, —N(C(O)NHR$_{29}$)—, —N(C(O)NR$_{29}$R$_{30}$)—, —N(S(O)$_2$NHR$_{29}$)—, —N(SO$_2$R$_{29}$)—, or —N(C(O)OR$_{29}$)—;
          wherein
            $R_{29}$ and $R_{30}$ independently comprise hydrogen, aryl, alkyl, or -alkylaryl;
            $R_{26}$ comprises hydrogen, alkyl, aryl, and alkylene-aryl;

X comprises sulfur or oxygen; and m and n are independently 0, 1, or 2.

In another embodiment, $Ar_2$ comprises

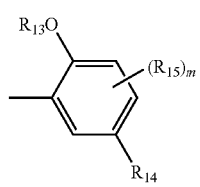

wherein
  $R_{14}$ comprises
    a) $-D_1$-perhalo-$C_2$-$C_6$ alkyl;
    b) $-D_1$-alkylene-heteroaryl;
    c) $-D_1$-alkylene-heterocyclyl;
    d) $-D_1$-alkylene-$NR_{18}R_{19}$; or
    e) -acid isostere;
    wherein
      $R_{13}$, $R_{15}$, $R_{18}$, $R_{19}$, and $D_1$ are defined as above.

In another embodiment, $Ar_2$ comprises

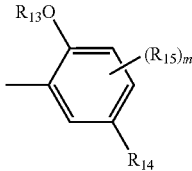

and $Ar_3$ comprises

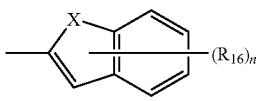

wherein $R_{13}$, $R_{14}$, $R_{15}$, $R_{16}$, X, m and n are defined as above.

In another embodiment, $Ar_2$ comprises

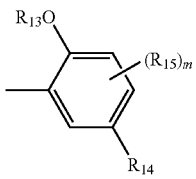

and $Ar_3$ comprises a phenyl group independently substituted 1 to 5 times, wherein $Ar_2$ and $Ar_3$ are different, and $R_{13}$, $R_{14}$, $R_{15}$, and m are defined as above. In a further embodiment, $Ar_3$ comprises a phenyl group substituted with at least one halo group.

In another embodiment, $Ar_2$ comprises

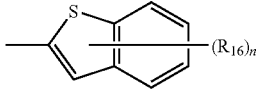

and $Ar_3$ comprises a phenyl, a benzothiopheneyl, or benzofuranyl group optionally independently substituted 1 to 5 times, wherein $Ar_2$ and $Ar_3$ are the same or different and $R_{16}$ and n are defined as above.

In another embodiment, $Ar_2$ comprises an unsubstituted benzothiophene group.

In another embodiment, $Ar_2$ and $Ar_3$ are different.

The alkyl, cycloalkyl, heterocyclyl, aryl, heteroaryl, alkylene, cycloalkylene, heterocyclylene, arylene, and heteroaryl groups in J, K, $Ar_2$, $Ar_3$, and $R_1$ through $R_{32}$ may be optionally independently substituted 1 to 4 times with a substituent group comprising:

a) -hydrogen;
b) -halo;
c) -cyano;
d) -nitro;
e) -perhaloalkyl;
f) -A-perhaloalkyl
g) -A-$R_{40}$;
h) -A-alkyl;
i) -A-aryl;
j) -A-alkylene-aryl;
k) -A-alkylene-$NR_{41}R_{42}$; or
l) -A-alkyl-E-$R_{43}$;

wherein

A and E independently comprise: $—CH_2—$, $—O—$, $—N(R_{44})—$, $—C(O)—$, $—CON(R_{44})—$, $—N(R_{44})C(O)—$, $—N(R_{44})CON(R_{45})—$, $—N(R_{44})C(O)O—$, $—OC(O)N(R_{44})—$, $—N(R_{44})SO_2—$, $—SO_2N(R_{44})—$, $—C(O)—O—$, $—O—C(O)—$, or $—N(R_{44})SO_2N(R_{45})—$, wherein $R_{44}$ and $R_{45}$ independently comprise: -hydrogen, -alkyl, -aryl, -arylene-alkyl, -alkylene-aryl, or -alkylene-arylene-alkyl;

$R_{40}$ and $R_{43}$ independently comprise: -hydrogen, -alkyl, -aryl, -arylene-alkyl, -alkylene-aryl, or -alkylene-arylene-alkyl; and $R_{41}$ and $R_{42}$ independently comprise hydrogen, aryl, or alkyl, wherein $R_{41}$ and $R_{42}$ may be taken together to form a ring having the formula $—(CH_2)_o-Z_4-(CH_2)_p—$ bonded to the nitrogen atom to which $R_{41}$ and $R_{42}$ are attached, wherein o and p are, independently, 1, 2, 3, or 4 and the o+p is less than or equal to 6, $Z_4$ comprises a direct bond a direct bond, $—CH_2—$, $—C(O)—$, $—O—$, $—N(H)—$, $—S—$, $—S(O)—$, $—S(O)_2—$, $—CON(H)—$, $—NHC(O)—$, $—NHC(O)N(H)—$, $—NH(SO_2)—$, $—S(O)_2N(H)—$, $—(O)CO—$, $—NHS(O)_2NH—$, $—OC(O)—$, $—N(R_{46})—$, $—N(C(O)R_{46})—$, $—N(C(O)NHR_{46})—$, $—N(C(O)NR_{46}R_{47})—$, $—N(S(O)_2NHR_{46})—$, $—N(SO_2R_{46})—$, or $—N(C(O)OR_{46})—$;

wherein $R_{46}$ and $R_{47}$ independently comprise hydrogen, aryl, alkyl, or -alkylene-aryl.

Examples of compounds of Formula (I) of the present invention are shown in Table 1 and in the Examples section.

TABLE 1

| Ex. | Structure | Name |
|---|---|---|
| 1 | 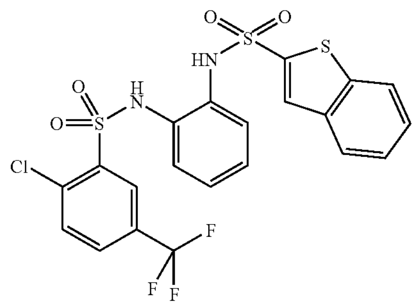 | Benzo[b]thiophene-2-sulfonic acid [2-(2-chloro-5-trifluoromethylbenzenesulfonyl-amino)phenyl]amide |
| 2 | 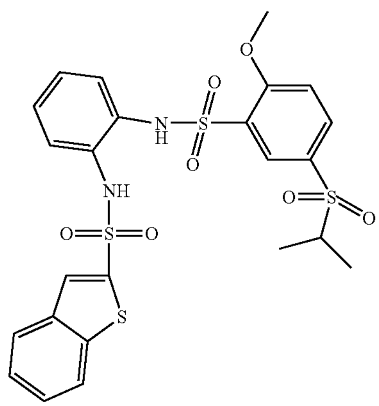 | Benzo[b]thiophene-2-sulfonic acid {2-[2-methoxy-5-(propane-2 sulfonyl)benzenesulfonylamino]phenyl}amide |
| 3 | 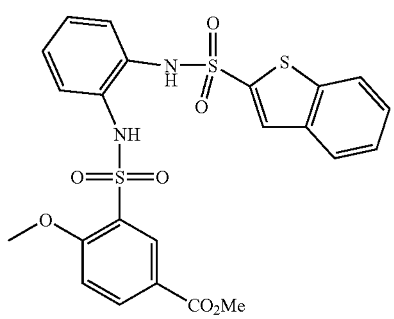 | 3-[2-(Benzo[b]thiophene-2-sulfonylamino)-phenylsulfamoyl]-4-methoxy-benzoic acid methyl ester |
| 4 | 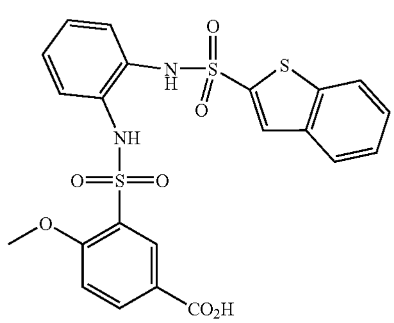 | 3-[2-(Benzo[b]thiophene-2-sulfonylamino)-phenylsulfamoyl]-4-methoxy-benzoic acid |

TABLE 1-continued

| Ex. | Structure | Name |
|---|---|---|
| 5 | 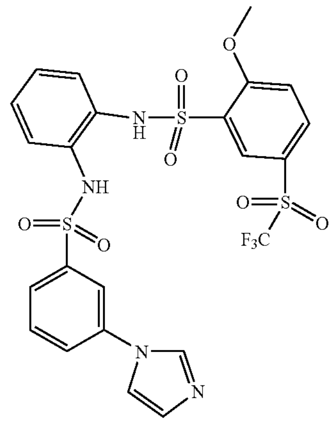 | N-[2-(3-Imidazol-1-yl-benzenesulfonylamino)-phenyl]-2-methoxy-5-trifluoromethanesulfonyl-benzenesulfonamide |
| 6 | 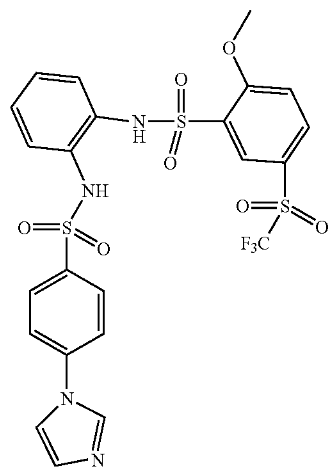 | N-[2-(4-Imidazol-1-yl-benzenesulfonylamino)-phenyl]-2-methoxy-5-trifluoromethanesulfonyl-benzenesulfonamide |
| 7 | 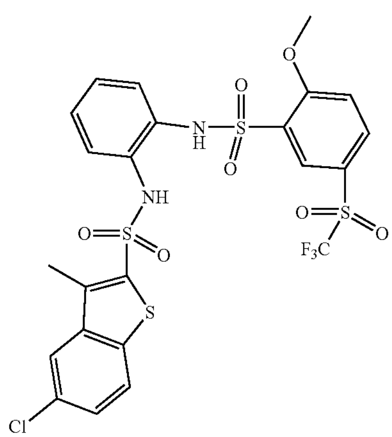 | 5-Chloro-3-methyl-benzo[b]thiophene-2-sulfonic acid [2-(2-methoxy-5-trifluoromethane sulfonyl-benzenesulfonyl-amino)phenyl]-amide |

TABLE 1-continued

| Ex. | Structure | Name |
| --- | --- | --- |
| 8 | 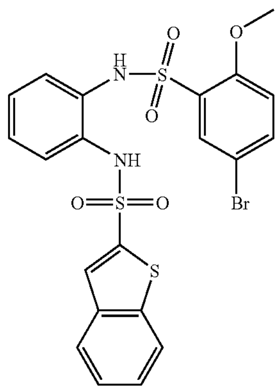 | Benzo[b]thiophene-2-sulfonic acid [2-(5-bromo-2-methoxy-benzene sulfonylamino)-phenyl]-amide |
| 9 | 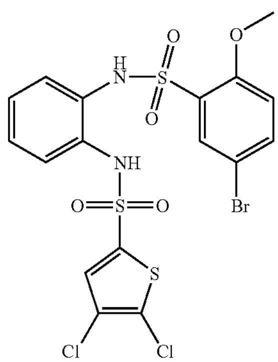 | 4,5-Dichlorothiophene-2-sulfonic acid [2-(5-bromo-2-methoxy-benzenesulfonylamino)-phenyl]-amide |
| 10 | 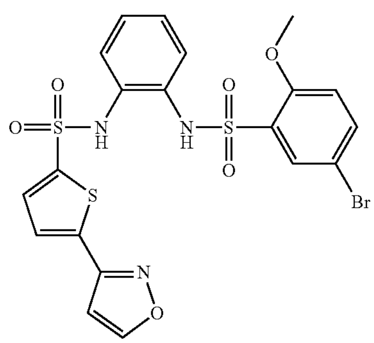 | 5-Isoxazol-3-yl-thiophene-2-sulfonic acid [2-(5-bromo-2-methoxy-benzenesulfonylamino)-phenyl]-amide |
| 11 | 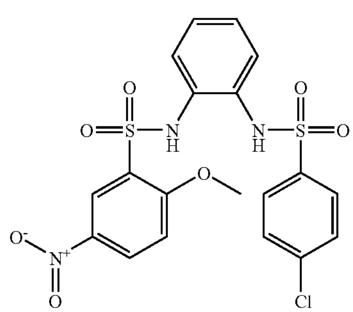 | N-[2-(4-Chloro-benzenesulfonylamino)phenyl]-2-methoxy-5-nitrobenzenesulfonamide |

TABLE 1-continued

| Ex. | Structure | Name |
|---|---|---|
| 12 | 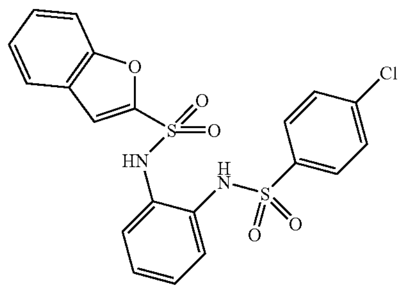 | Benzofuran-2-sulfonic acid [2-(4-chloro-benzenesulfonylamino)phenyl] amide |
| 13 | 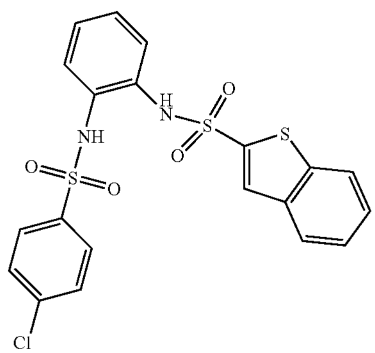 | Benzo[b]thiophene-2-sulfonic acid [2-(4-chloro-benzenesulfonylamino)phenyl] amide |
| 14 | 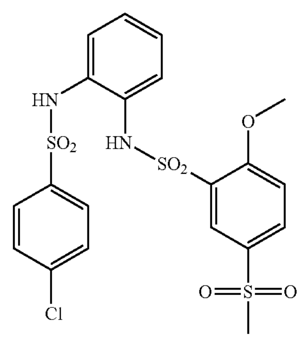 | N-[2-(4-Chlorobenzenesulfonylamino)phenyl]-5-methanesulfonyl-2-methoxybenzenesulfonamide |
| 15 | 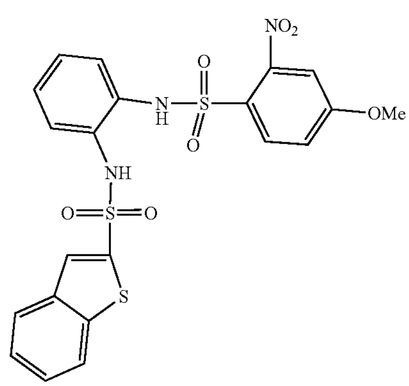 | Benzo[b]thiophene-2-sulfonic acid [2-(4-methoxy-2-nitro-benzenesulfonylamino)phenyl]amide |
| 16 | 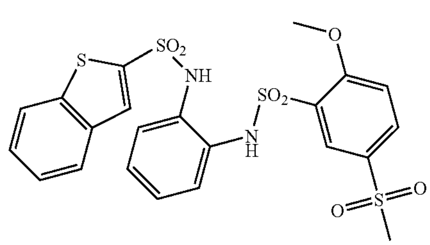 | Benzo[b]thiophene-2-sulfonic acid [2-(4-methanesulfonyl-2-methoxy-benzenesulfonylamino)-phenyl] amide |

TABLE 1-continued

| Ex. | Structure | Name |
|---|---|---|
| 17 | 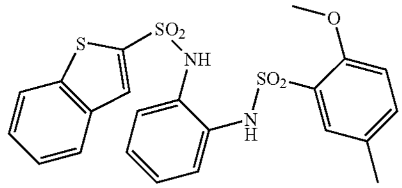 | Benzo[b]thiophene-2-sulfonic acid [2-(2-methoxy-5-methylbenzenesulfonylamino)phenyl] amide |
| 18 | 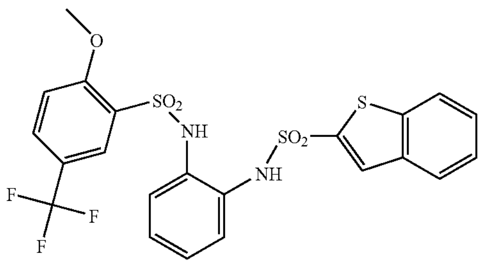 | Benzo[b]thiophene-2-sulfonic acid [2-(2-methoxy-5-trifluoromethyl-benzenesulfonylamino)phenyl] amide |
| 19 | 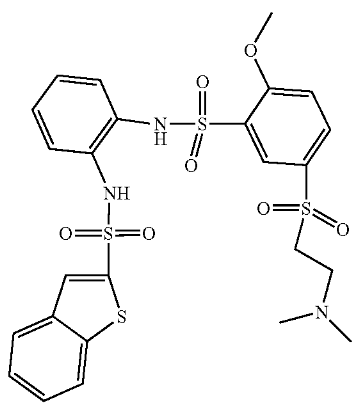 | Benzo[b]thiophene-2-sulfonic acid {2-[5-(2-dimethylaminoethanesulfonyl)-2-methoxy-benzenesulfonylamino]phenyl} amide |
| 20 | 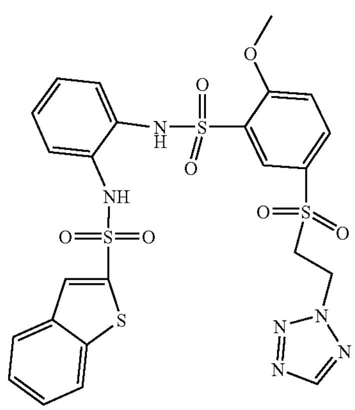 | Benzo[b]thiophene-2-sulfonic acid {2-[2-methoxy-5-(2-tetrazol-2-yl-ethanesulfonyl)-benzenesulfonylamino]-phenyl}-amide |

TABLE 1-continued

| Ex. | Structure | Name |
|---|---|---|
| 21 | 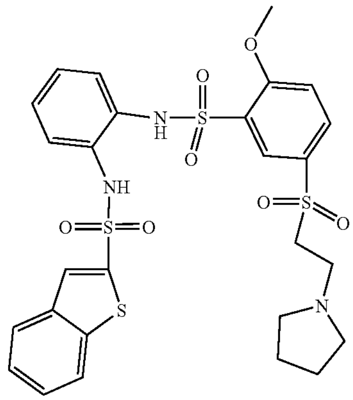 | Benzo[b]thiophene-2-sulfonic acid {2-[2-methoxy-5-(2-pyrrolidin-1-yl-ethanesulfonyl)-benzenesulfonylamino]-phenyl}-amide |
| 22 | 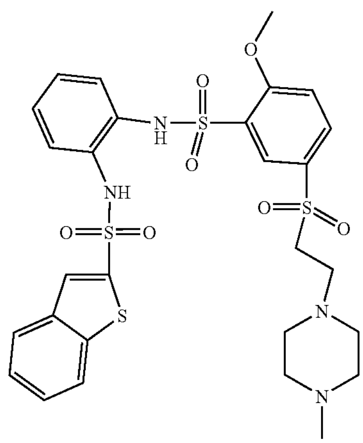 | Benzo[b]thiophene-2-sulfonic acid {2-[2-methoxy-5-(2-pyrrolidin-1-yl-ethanesulfonyl)-benzenesulfonylamino]-phenyl}-amide |
| 23 | 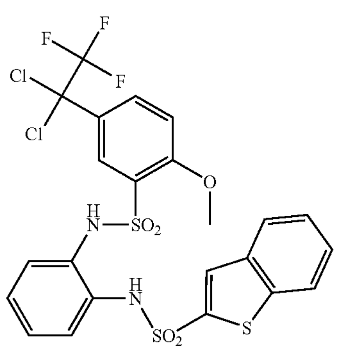 | Benzo[b]thiophene-2-sulfonic acid [2-(5-(1,1-Dichloro-2,2,2-trifluoroethyl)-2-methoxy-benzenesulfonylamino)phenyl]amide |
| 24 | 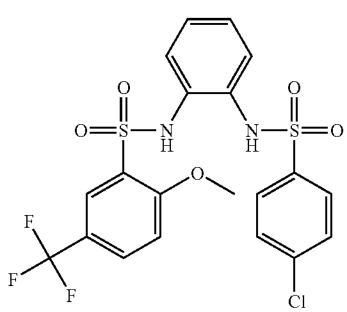 | N-[2-(4-Chlorobenzenesulfonylamino)phenyl]-2-methoxy-5-trifluoromethylbenzenesulfonamide |

TABLE 1-continued

| Ex. | Structure | Name |
|---|---|---|
| 25 | 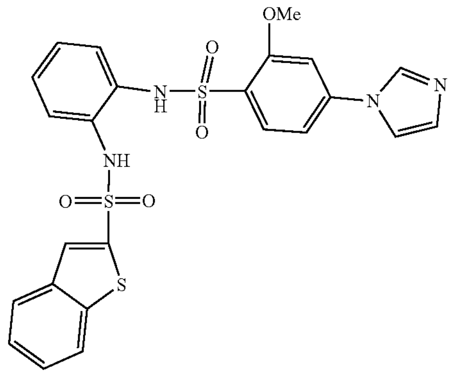 | Benzo[b]thiophene-2-sulfonic acid [2-(4-imidazol-1-yl-2-methoxybenzenesulfonylamino)phenyl]amide |
| 26 | 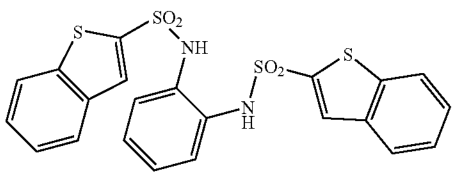 | N-[2-(Benzothiophene-2-sulfonyl)amino]phenyl-benzothiophene-2-sulfonamide |
| 27 | 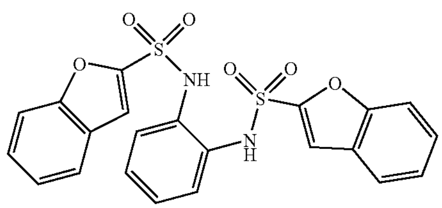 | N-[2-(Benzothiophene-2-sulfonyl)amino]phenyl-benzothiophene-2-sulfonamide |
| 28 | 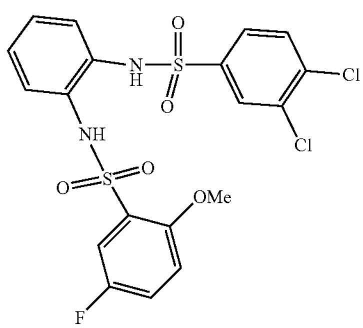 | N-[2-(3,4-Dichlorobenzenesulfonylamino)-phenyl]-5-fluoro-2-methoxybenzenesulfonamide |
| 29 | 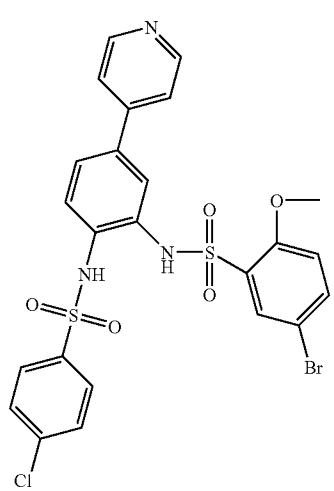 | 5-Bromo-N-[2-(4-chlorobenzenesulfonylamino)-5-pyridin-4-ylphenyl]-2-methoxybenzenesulfonamide |

TABLE 1-continued

| Ex. | Structure | Name |
|---|---|---|
| 30 | 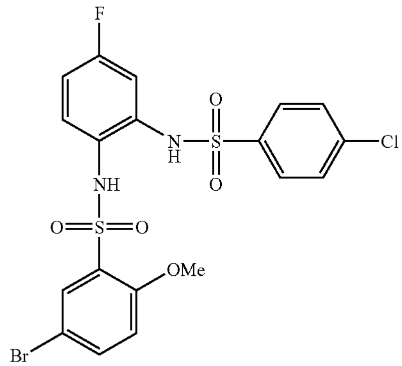 | 5-Bromo-N-[2-(4-chlorobenzenesulfonylamino)-4-fluorophenyl]-2-methoxybenzenesulfonamide |
| 31 | 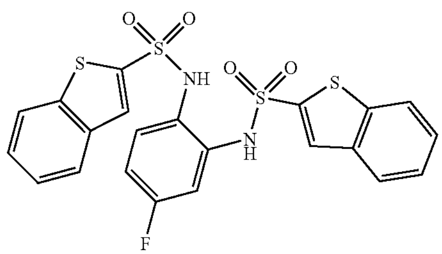 | N,N'-(4-fluoro-1,2-phenylene)bis(1-benzothiophene-2-sulfonamide) |
| 32 | 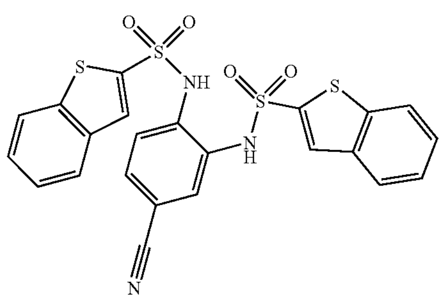 | N,N'-(4-cyano-1,2-phenylene)bis(1-benzothiophene-2-sulfonamide) |
| 33 | 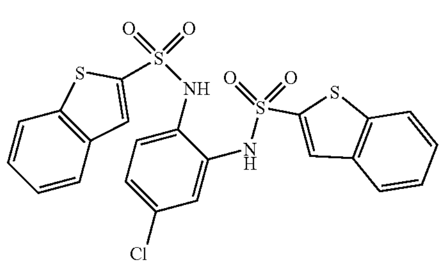 | N,N'-(4-chloro-1,2-phenylene)bis(1-benzothiophene-2-sulfonamide) |

TABLE 1-continued

| Ex. | Structure | Name |
|---|---|---|
| 34 | 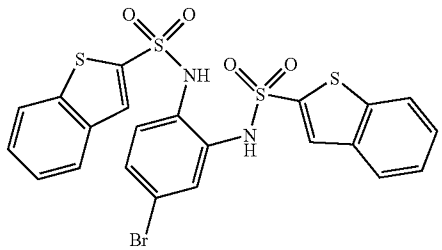 | N,N'-(4-bromo-1,2-phenylene)bis(1-benzothiophene-2-sulfonamide) |
| 35 | 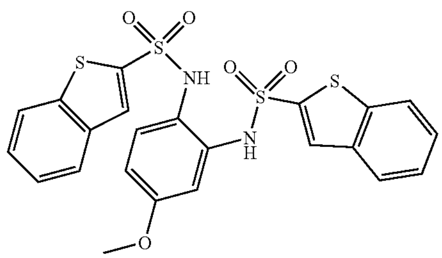 | N,N'-(4-methoxy-1,2-phenylene)bis(1-benzothiophene-2-sulfonamide) |
| 36 | 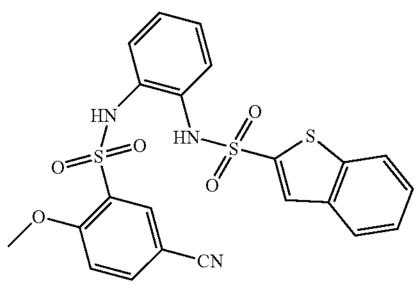 | Benzo[b]thiophene-2-sulfonic acid [2-(5-cyano-2-methoxy-benzenesulfonylamino)-phenyl]-amide |
| 37 | 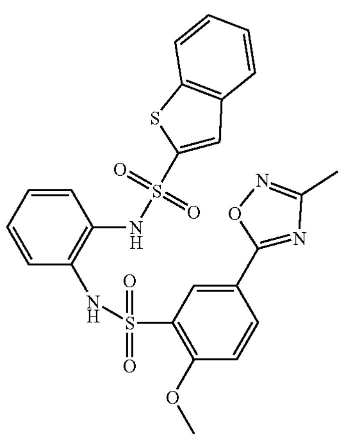 | Benzo[b]thiophene-2-sulfonic acid {2-[2-methoxy-5-(3-methyl-[1,2,4]oxadiazol-5-yl)-benzenesulfonylamino]-phenyl}-amide |
| 38 | 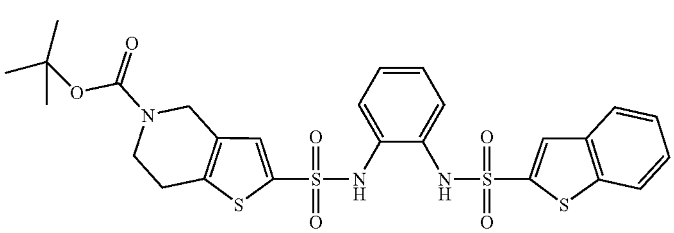 | 2-[2-(Benzo[b]thiophene-2-sulfonylamino)-phenylsulfamoyl]-6,7-dihydro-4H-thieno[3,2-c]pyridine-5-carboxylic acid tert-butyl ester |

TABLE 1-continued

| Ex. | Structure | Name |
|---|---|---|
| 39 | 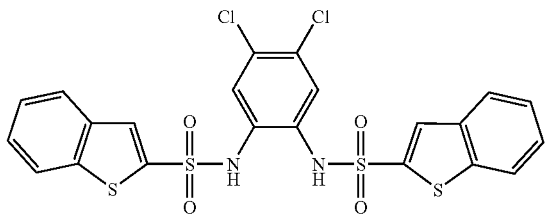 | N,N'-(4,5-dichloro-1,2-phenylene)bis(1 benzothiophene-2-sulfonamide) |
| 40 | 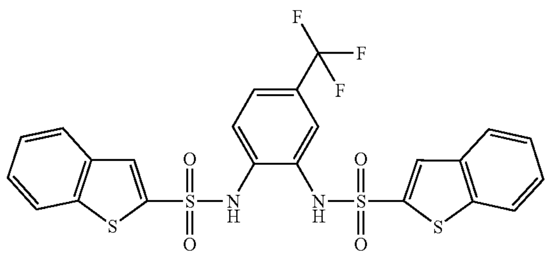 | N,N'-(4-trifluoromethyl-1,2-phenylene)bis(1-benzothiophene-2-sulfonamide) |
| 41 | 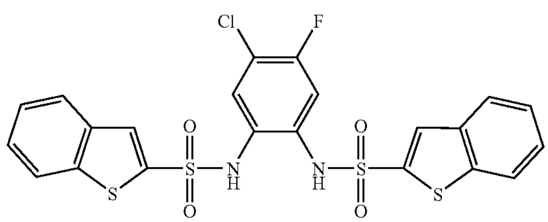 | N,N'-(4-chloro-5-fluoro-1,2-phenylene)bis(1-benzothiophene-2-sulfonamide) |
| 42 | 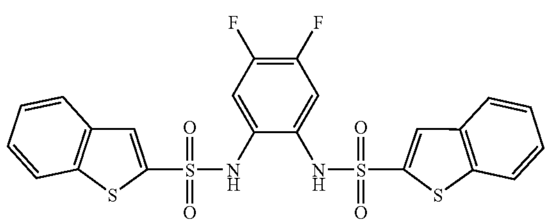 | N,N'-(4,5-fluoro-1,2-phenylene)bis(1-benzothiophene-2-sulfonamide) |

Unless indicated otherwise, the structures of the Examples of compounds of Formula (I) having vacant connectivity for heteroatoms, such as oxygen and nitrogen, are assumed to have a hydrogen atom attached thereto.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may containing one or more O, S, S(O), or S(O)$_2$ atoms. Examples of "alkyl" as used herein include, but are not limited to, methyl, n-butyl, t-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may containing one or more O, S, S(O), or S(O)$_2$ atoms. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may containing one or more O, S, S(O), or S(O)$_2$ atoms.

As used herein, the term "alkenylene" refers to a straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenylene" group may containing one or more O, S, S(O), or $S(O)_2$ atoms. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may containing one or more O, S, S(O), or $S(O)_2$ atoms.

As used herein, the term "alkynylene" refers to a straight or branched chain divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may containing one or more O, S, S(O), or $S(O)_2$ atoms. Examples of "alkynylene" as used herein include, but are not limited to, ethyne-1,2-diyl, propyne-1,3-diyl, and the like.

As used herein, "cycloalkyl" refers to a alicyclic hydrocarbon group optionally possessing one or more degrees of unsaturation, having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an nonaromatic alicyclic divalent hydrocarbon radical having from three to twelve carbon atoms and optionally possessing one or more degrees of unsaturation, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring optionally possessing one or more degrees of unsaturation, containing one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "heterocyclylene" refers to a three to twelve-membered heterocyclic ring diradical optionally having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-dyil, and the like.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include 5-indanyl, 5,6,7,8-tetrahydro-2-naphthyl,

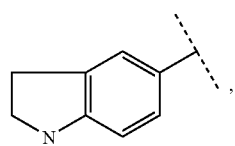

and the like.

As used herein, the term "fused cycloalkylarylene" refers to a fused cycloalkylaryl, wherein the aryl group is divalent. Examples include

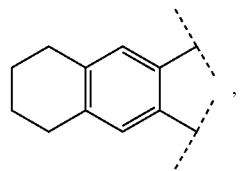

and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

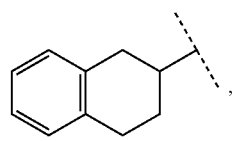

and the like.

As used herein, the term "fused arylcycloalkylene" refers to a fused arylcycloalkyl, wherein the cycloalkyl group is divalent. Examples include

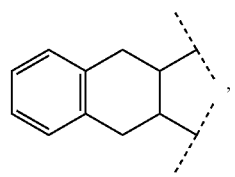

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include 3,4-methylenedioxy-1-phenyl, and the like As used herein, the term "fused heterocyclylarylene" refers to a fused heterocyclylaryl, wherein the aryl group is divalent. Examples include

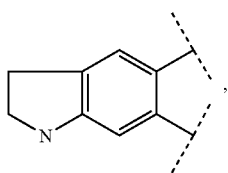

and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include 2-(1,3-benzodioxolyl),

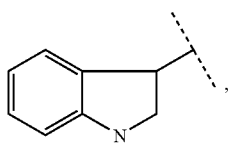

and the like.

As used herein, the term "fused arylheterocyclylene" refers to a fused arylheterocyclyl, wherein the heterocyclyl group is divalent. Examples include

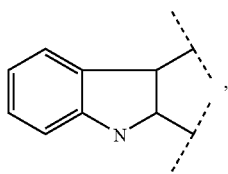

and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include 5-aza-6-indanyl,

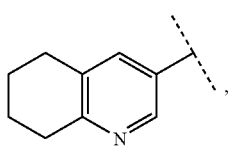

and the like.

As used herein, the term "fused cycloalkylheteroarylene" refers to a fused cycloalkylheteroaryl, wherein the heteroaryl group is divalent. Examples include

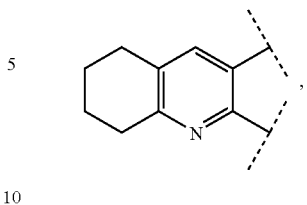

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include 5-aza-1-indanyl,

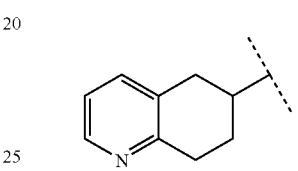

and the like.

As used herein, the term "fused heteroarylcycloalkylene" refers to a fused heteroarylcycloalkyl, wherein the cycloalkyl group is divalent. Examples include

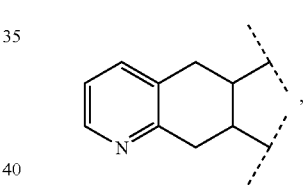

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include 1,2,3,4-tetrahydro-beta-carbolin-8-yl, 6,7-dihydro-4H-thieno[3,2-c]pyridine,

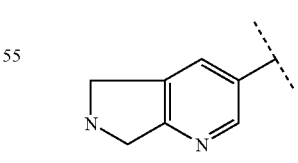

and the like.

As used herein, the term "fused heterocyclylheteroarylene" refers to a fused heterocyclylheteroaryl, wherein the heteroaryl group is divalent. Examples include

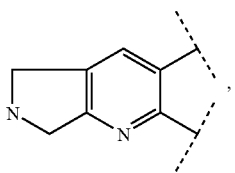

and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroarylheterocyclyl" used herein include -5-aza-2,3-dihydrobenzofuran-2-yl,

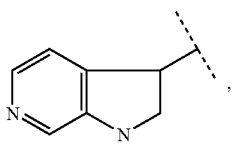

and the like.

As used herein, the term "fused heteroarylheterocyclylene" refers to a fused heteroarylheterocyclyl, wherein the heterocyclyl group is divalent. Examples include

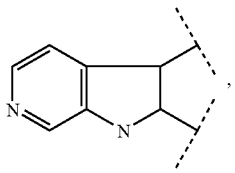

and the like.

As used herein, the term "acid isostere" refers to a substituent group, which will ionize at physiological pH to bear a net negative charge. Examples of such "acid isosteres" include but are not limited to heteroaryl groups such as but not limited to isoxazol-3-ol-5-yl, 1H-tetrazole-5-yl, or 2H-tetrazole-5-yl. Such acid isosteres include but are not limited to heterocyclyl groups such as but not limited to imidazolidine-2,4-dione-5-yl, imidazolidine-2,4-dione-1-yl, 1,3-thiazolidine-2,4-dione-5-yl, or 5-hydroxy-4H-pyran-4-on-2-yl.

As used herein, the term "direct bond", where part of a structural variable specification, refers to the direct joining of the substituents flanking (preceding and succeeding) the variable taken as a "direct bond".

As used herein, the term "perhaloalkyl" refers to a straight or branched chain hydrocarbon having from one to ten carbon atoms, where each position for substitution is substituted with a halogen atom. A perhaloalkyl group may be substituted with one or more types of halogen atoms. Examples of "perhaloalkyl" as used herein include, but are not limited to, a trifluoromethyl group and a 1,1-dichloro-2,2,2-trifluoroethyl group, and the like.

As used herein, the term "geminal" refers to two individual atoms, chemical groups or substituents, either the same or different, which are connected to the same atom. Such a "geminal" relationship may occur in a chain of atoms or in a ring system. By way of example, in 2-methoxypyridine, the nitrogen atom and the methoxy group are in a "geminal" relationship.

As used herein, the term "vicinal" refers to two individual atoms, chemical groups or substituents, either the same or different, which are connected to adjacent atoms. Two such "vicinal" atoms, substituents, or chemical groups may substitute consecutive, adjacent atoms in a chain of atoms or in a ring system. By way of example, in catechol, the two phenolic hydroxy groups are said to be in a "vicinal" relationship.

As used herein, the term "alkoxy" refers to the group $R_aO-$, where $R_a$ is alkyl.

As used herein, the term "alkenyloxy" refers to the group $R_aO-$, where $R_a$ is alkenyl.

As used herein, the term "alkynyloxy" refers to the group $R_aO-$, where $R_a$ is alkynyl.

As used herein, the term "alkylsulfanyl" refers to the group $R_aS-$, where $R_a$ is alkyl.

As used herein, the term "alkenylsulfanyl" refers to the group $R_aS-$, where $R_a$ is alkenyl.

As used herein, the term "alkynylsulfanyl" refers to the group $R_aS-$, where $R_a$ is alkynyl.

As used herein, the term "alkylsulfenyl" refers to the group $R_aS(O)-$, where $R_a$ is alkyl.

As used herein, the term "alkenylsulfenyl" refers to the group $R_aS(O)-$, where $R_a$ is alkenyl.

As used herein, the term "alkynylsulfenyl" refers to the group $R_aS(O)-$, where $R_a$ is alkynyl.

As used herein, the term "alkylsulfonyl" refers to the group $R_aSO_2-$, where $R_a$ is alkyl.

As used herein, the term "alkenylsulfonyl" refers to the group $R_aSO_2-$, where $R_a$ is alkenyl.

As used herein, the term "alkynylsulfonyl" refers to the group $R_aSO_2-$, where $R_a$ is alkynyl.

As used herein, the term "acyl" refers to the group $R_aC(O)-$, where $R_a$ is alkyl, alkenyl, alkynyl, cycloalkyl, cycloalkenyl, or heterocyclyl.

As used herein, the term "aroyl" refers to the group $R_aC(O)-$, where $R_a$ is aryl.

As used herein, the term "heteroaroyl" refers to the group $R_aC(O)-$, where $R_a$ is heteroaryl.

As used herein, the term "alkoxycarbonyl" refers to the group $R_aOC(O)-$, where $R_a$ is alkyl.

As used herein, the term "acyloxy" refers to the group $R_aC(O)O-$, where $R_a$ is alkyl, alkenyl, alkynyl, cycloalkyl, cycloalkenyl, or heterocyclyl.

As used herein, the term "aroyloxy" refers to the group $R_aC(O)O-$, where $R_a$ is aryl.

As used herein, the term "heteroaroyloxy" refers to the group $R_aC(O)O-$, where $R_a$ is heteroaryl.

As used herein, the term "optionally" means that the subsequently described event(s) may or may not occur, and includes both event(s), which occur, and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, $-CH_2-O-CH_2-$, $-CH_2-SO_2-CH_2-$, $-CH_2-NH-CH_3$ and so forth.

Whenever the terms "alkyl" or "aryl" or either of their prefix roots appear in a name of a substituent (e.g. arylalkoxyaryloxy) they shall be interpreted as including those limitations given above for "alkyl" and "aryl". Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —$C(O)NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

The compounds of Formula (I) may be prepared according to the following reaction Schemes (in which variables are as defined before or are defined in the Schemes and Examples). In these reactions, it is also possible to make use of variants that are themselves known to those of ordinary skill in this art, but are not mentioned in greater detail.

Scheme 1 describes the preparation of a compound of formula (2). In this scheme $Ar_1$ and $Ar_3$ have the same meaning as for formula (I). $R_{51}$ represents a substituent such as but not limited to alkyl, aryl, heteroaryl, alkoxy or halogen.

Scheme 1

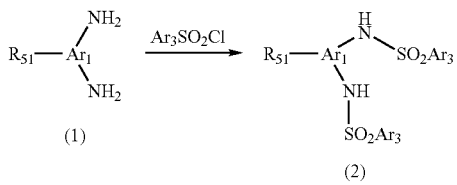

(1) → (2)

Bissulfonamides (2) may be prepared by treatment of a phenylenediamine (1) with an aryl or heteroaryl sulfonyl chloride in presence of a base such as pyridine or triethylamine in an aprotic solvent such as dichloromethane or DMF at a temperature of from 0° C. to 100° C.

Scheme 2 describes a synthesis of a compound of formula (4).

Scheme 2

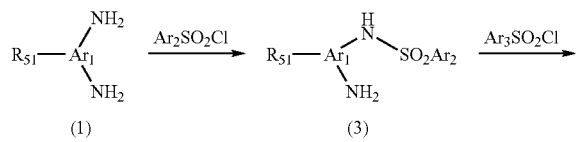

(1) → (3) →

-continued

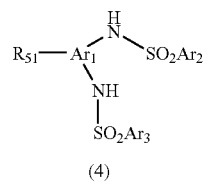

(4)

Phenylenediamine (1) may be monosulfonated with an aryl or heteroaryl sulfonyl chloride in presence of a base such as pyridine or triethylamine in an aprotic solvent such as but not limited to dichloromethane or DMF at a temperature of from 0° C. to 100° C. to afford sulfonamidoanilines (3). Such a monosulfonylation may take place preferentially when 0.5 to 1.5 molar equivalents of the sulfonyl chloride are employed. The sulfonamidoaniline (3) obtained may be further sulfonated with an aryl or heteroaryl sulfonyl chloride in the presence of a base such as pyridine or triethylamine in an aprotic solvent such as dichloromethane or DMF at a temperature of from 0° C. to 100° C. to provide the bissulfonamide (4).

Scheme 3 describes an alternative synthesis of a compound of formula (4).

Scheme 3

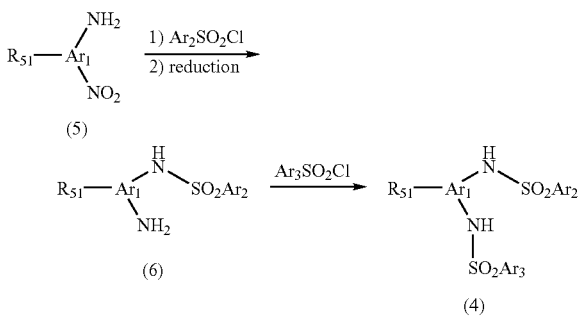

2-Nitroanilines (5), either unsubstituted or substituted with a substituent $R_{51}$, may be sulfonylated with an aryl or heteroaryl sulfonyl chloride in pyridine as solvent, optionally in a aprotic cosolvent like DMF or acetonitrile in the presence of a base such as pyridine or triethylamine, at a temperature of from 0° C. to 100° C., to afford a 2-sulfonamidonitroaryl intermediate. The 2-sulfonamidonitroarene thus obtained may be reduced using methods such as but not limited to hydrogenation with a noble metal catalyst such as palladium on carbon, or reduction with $SnCl_2$ in EtOH (alternatively with $LiAlH_4$) to provide 2-sulfonamidoanilines (6). The aniline (6) may be sulfonylated as described previously to afford (4).

Scheme 4 describes the preparation of a sulfonyl chloride (8). $R_{52}$ is a substituent such as but not limited to alkyl, aryl, alkoxy, or -alklylaryl.

Scheme 4

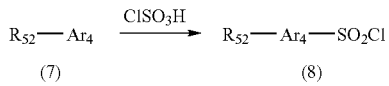

(7) → (8)

The sulfonyl chloride (8) may be prepared by reacting an arene or heteroarene (7) with chlorosulfonic acid in a solvent such as DCM or DCE at a temperature of from 0° C. to 100° C., to afford the desired sulfonyl chloride (8).

Scheme 5 describes an alternate synthesis of a sulfonyl chloride (8). X is Br or I. M is —MgX or Li.

Scheme 5

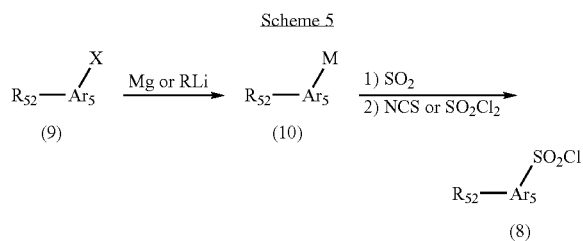

An arene or heteroarene with a halogen substituent (9) may be metallated by treatment with magnesium metal in a solvent such as ether or THF, at a temperature of from −20° C. to 100° C., to afford the organometallic reagent (10) where M is —MgX. Alternately, treatment of (9) with n-butyllithium under inert atmosphere in a solvent such as ether or THF, at a temperature of from −78° C. to 0° C. affords (10) where M is Li. Alternately, treatment of (9) with 2 equivalents of tert-butyllithium under inert atmosphere in a solvent such as ether or THF, at a temperature of from −78° C. to 0° C., affords (10) where M is Li. The metalloarene or metalloheteroarene intermediate (10) thus formed may be treated with sulfur dioxide in an ethereal solvent such as THF to afford a sulfinate salt that is subsequently treated with N-chlorosuccinimide or sulfuryl chloride to provide the desired sulfonyl chloride (8).

The present invention also provides a method for the synthesis of compounds useful as intermediates in the preparation of compounds of Formula (I) along with methods for the preparation of compounds of Formula (I).

Procedure A

To a solution of o-phenylenediamine (1 mmol) in and DCM (4 mL) pyridine (1 mL) at 0° C., arylsulfonyl chloride (2.2 mmol) was added at 0° C. in small portions at 0° C. The reaction mixture was then gradually warmed to RT with stirring continued until the reaction is complete as determined by TLC or LC-MS. In some cases, the reaction is allowed to proceed overnight to ensure completion and/or may be aided by adding catalytic amount of DMAP. The reaction mixture was then diluted with DCM (5 mL). The organic phase was washed with 10% HCl aqueous solution (5 mL), water (5 mL) and 5 mL of brine. The organic phase was dried over anhydrous sodium sulfate, and concentrated under vacuum. The residue obtained was purified by flash column chromatography eluting with DCM/EtOAc system to obtain the requisite bissulfonamide.

Procedure B

To a solution of o-phenylenediamine (1 mmol) in and DCM (4 mL) pyridine (1 mL) at 0° C., arylsulfonyl chloride (1.1 mmol) is added at 0° C. in small portions at 0° C. The reaction mixture is then gradually warmed to RT with stirring continued until the reaction is complete as determined by TLC or LC-MS. The reaction mixture is then diluted with DCM (5 mL). The organic phase is washed with water (2×5 mL) and 5 mL of brine. The organic phase is dried over anhydrous sodium sulfate, and concentrated under vacuum. The residue obtained is purified by flash column chromatography eluting with DCM/EtOAc system to obtain the sulfonamide.

The monosulfonamide (1 mmol) obtained as above is dissolved in DCM (2 mL) and pyridine (2 mL). Arylsulfonyl chloride (1.1 mmol) is then added at RT and the reaction mixture is then allowed to stir at RT overnight or until the reaction is complete as determined by TLC or LC-MS. In some cases, the reaction is allowed to proceed overnight to ensure completion and/or may be aided by adding catalytic amount of DMAP. The reaction mixture is then diluted with DCM (5 mL). The organic phase is washed with 10% HCl aqueous solution (5 mL), water (5 mL) and 5 mL of brine. The organic phase is dried over anhydrous sodium sulfate, and concentrated under vacuum. The residue obtained is purified by flash column chromatography eluting with DCM/EtOAc system to obtain the requisite bissulfonamide.

Procedure C

To a stirred solution of nitroaniline (2 mmol) in pyridine (4 mL) at RT, sulfonyl chloride (2.2 mmol) is added and the resulting reaction mixture is then heated at 100° C. until the reaction is complete as determined by TLC or LC-MS. The reaction mixture is diluted with EtOAc (20 mL) and washed with 10% aq. HCl (2×10 mL), $H_2O$ (2×10 mL) and brine (10 mL). The product may be used without further purification or may be purified on a silica gel column chromatography using EtOAc/hexane as eluant.

Hydrogenation is carried out in MeOH using 10% Pd/C (wet) under 1 atm. Alternatively, when hydrogenation is not compatible, reduction is performed using Fe/AcOH as follows: Sulfonamide from above (2 mmol) in AcOH (2 mL) is added with Fe powder (20 mmol). The reaction mixture is then heated at 100° C. until the reaction is complete as determined by TLC or LC-MS. The reaction mixture is then cooled to RT and diluted with EtOAc (20 mL) with vigorous stirring. The suspension is then filtered on a Celite pad and the filtrate is then concentrated in vacuo to remove most of the acetic acid. The residue obtained is redissolved in EtOAc (20 mL), washed with saturated aqueous bicarbonate solution (20 mL), followed by water (20 mL) and brine (20 mL). The product may be used for further transformation without any purification.

The monosulfonamide (1 mmol) obtained as above is dissolved in DCM (2 mL) and pyridine (2 mL). Arylsulfonyl chloride (1.1 mmol) is then added at RT and the reaction mixture is then allowed to stir at RT overnight or until the reaction is complete as determined by TLC or LC-MS. In some cases, the reaction is allowed to proceed overnight to ensure completion and/or may be aided by adding catalytic amount of DMAP. The reaction mixture was then diluted with DCM (5 mL). The organic phase was washed with 10% HCl aqueous solution (5 mL), water (5 mL) and 5 mL of brine. The organic phase is dried over anhydrous sodium sulfate, and concentrated under vacuum. The residue obtained is purified by flash column chromatography eluting with DCM/EtOAc system to obtain the requisite bissulfonamide.

The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like.

The term "parenteral" as used herein, includes subcutaneous injections, intravenous, intramuscular, intracisternal injection, or by infusion techniques.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. The tablets may also be coated by the techniques described in U.S. Pat. Nos. 4,356,108; 4,166,452; and 4,265,874, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alchol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient, which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

As used herein, the term "solvate" is a complex of variable stoichiometry formed by a solute (in this invention, a compound of Formula (I)) and a solvent. Such solvents for the purpose of the invention may not sunstantially interfere with the biological activity of the solute. Solvents may be, by way of example, water, ethanol, or acetic acid.

As used herein, the term "biohydrolyzable ester" is an ester of a drug substance (in this invention, a compound of Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to Formula (I) in plasma. Many examples of such are known in the art and include by way of example lower alkyl esters (e.g., C1-C4), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. A biohydrolyzable amide may be orally absorbed from the gut and transformed to Formula (I) in plasma. Many examples of such are known in the art and include by way of example lower alkyl amides, alpha-amino acid amides, alkoxyacyl amides, and alkylaminoalkylcarbonyl amides.

Prodrugs of the compounds of the present invention are also included within the scope of the invention. As used herein, the term "prodrug" includes biohydrolyzable amides and biohydrolyzable esters and encompasses a) compounds in which the biohydrolyzable functionality in such a prodrug is encompassed in the compound of Formula (I), and b) compounds that may be oxidized or reduced biologically at a given functional group to yield drug substances of Formula (I). Examples of these functional groups include, but are not limited to, 1,4-dihydropyridine, N-alkylcarbonyl-1,4-dihydropyridine, 1,4-cyclohexadiene, tert-butyl, and the like.

The term "pharmacologically effective amount" shall mean that amount of a drug or pharmaceutical agent that will elicit the biological or medical response of a tissue, animal or human that is being sought by a researcher or clinician. This amount can be a therapeutically effective amount.

The term "therapeutically effective amount" is used herein to denote that amount of a drug or pharmaceutical agent that will elicit the therapeutic response of an animal or human that is being sought.

The term "treatment" as used herein, refers to the full spectrum of treatments for a given disorder from which the patient is suffering, including alleviation of one, most of all symptoms resulting from that disorder, to an outright cure for the particular disorder or prevention of the onset of the disorder.

Pharmaceutically acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Methanesulfonate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19.

Other salts that are not pharmaceutically acceptable may be useful in the preparation of compounds of the invention and these form a further aspect of the invention.

In addition, some of the compounds of Formula (I) may form solvates with water or common organic solvents. Such solvates are also encompassed within the scope of the invention.

The terms "analgesia", "antinociception", and "anti-allodynia" are used to describe pain reduction and the reduction of pain associated with neuropathic pain, as well as allodynia often associated with neuropathic pain.

As used herein, a compound that is "substantially unable to cross the blood-brain barrier" or "partially or completely excluded from the brain" is a compound that diffuses across the blood-brain barrier at a lower rate than the rate of diffusion in the periphery of a subject.

In an embodiment, at dose levels that are able to stimulate GalR1 receptors in the periphery of a subject, a compound that is "substantially unable to cross the blood-barrier" or "partially or completely excluded form the brain" may be present in the brain of a subject at about or below the limit of detection.

In another embodiment, at dose levels in which an analgesic effect is observed in a subject, a compound that is "substantially unable to cross the blood-brain barrier" or "partially or completely excluded from the brain" may be present in the brain of a subject at about or below the limit of detection.

As used herein, the term "subject" includes mammalian subjects such as, but not limited to, humans, dogs, cats, cows, horses, and other agricultural live stock. In an embodiment, a subject may include one that either suffers from one or more aforesaid diseases, disease states, or one that is at risk for contracting one or more aforesaid diseases, or disease states.

As used herein, a GalR1 agonist comprises compounds: 1) that are capable of binding to a GalR1 receptor and inhibiting forskolin induced cAMP production in Bowes cells that express the human GalR1 receptor; and 2) that do not inhibit forskolin induced cAMP production in cell lines that do not express the GalR1 receptor. In an embodiment, a GalR1 agonist is a compound that exhibits greater efficacy in a functional assay in comparison to no ligand.

In another embodiment, the present invention provides a pharmaceutical composition comprising a compound of Formula (I)

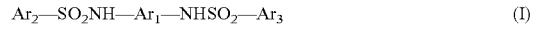

$$Ar_2—SO_2NH—Ar_1—NHSO_2—Ar_3 \quad (I)$$

wherein $Ar_1$, $Ar_2$ and $Ar_3$ are as defined above, and the compound of Formula (I) is a GalR1 agonist.

In another embodiment, the present invention provides a pharmaceutical composition comprising a compound of Formula (I) and a pharmaceutically suitable carrier, excipient, diluent, or a mixture thereof.

In another embodiment, the present invention also provides a pharmaceutical composition comprising a compound of Formula (I), wherein the compound of Formula (I) is a GalR1 agonist and the compound of Formula (I) is present in an amount sufficient to increase activity of a GalR1 receptor. In another embodiment, the pharmaceutical composition comprises a compound of Formula (I), wherein the compound of Formula (I) is a GalR1 agonist and the compound of Formula (I) is present in an amount sufficient to stimulate GalR1 in a subject.

In another embodiment, the present invention provides a pharmaceutical composition comprising a therapeutically effective amount of a compound of Formula (I), wherein said therapeutically effective amount comprises an amount of the compound of Formula (I) capable of at least partially activating the GalR1 receptor in a subject, or an amount of the compound of Formula (I) capable of at least partial amelioration of at least one GalR1 mediated disease.

Diseases or disorders that may be ameliorated by a GalR1 agonist may include a seizure disorder, a neuroendocrine disorder, a gastrointestinal disorder, a musculoskeletal disorder, psychotic behavior such as schizophrenia, migraine, morphine tolerance, drug addition, particularly opiate addiction, pain, particularly neuropathic pain, inflammatory pain, chronic pain, a sleep disorder, eating/body weight disorders such as bulimia, bulimia nervosa, and anorexia nervosametabolic wasting disorders such as cachexia, neuropathological disorders, diabetes, dyslipidimia, hypertension, memoryloss, depression, anxiety, cerebral hemorrhage, diarrhea, and one or more cancers such as, but not limited to, squamous cell carcinoma. Accordingly, treatment of such disorders may be affected by the administration of a GalR1 agonist. It is contemplated within the scope of the invention that compounds of Formula (I) and pharmaceutical compositions comprising a compound of Formula (I) may be formulated to treat disorders that are not associated with binding of galanin (or lack thereof) to the GalR1 receptor but where the symptoms of the disorder may be mediated by a GalR1 agonist.

In another embodiment, the pharmaceutical composition is in the form of an oral dosage. In another embodiment, the pharmaceutical composition is in the form of a parenteral dosage unit.

In another aspect, the present invention provides a pharmaceutical composition comprising a compound of Formula (I), and one or more additional therapeutic agents. In another embodiment, the pharmaceutical composition may further comprise one or more therapeutic agents selected from the group consisting of biologic response modifiers, analgesics, NSAIDs, DMARDs, glucocorticoids, sulfonylureas, biguanides, acarbose, PPAR agonists, DPP-IV inhibitors, GK activators, insulin, insulin mimetics, insulin secretagogues, insulin sensitizers, GLP-1, GLP-1 mimetics, cholinesterase inhibitors, antipsychotics, antidepressants, anticonvulsants, HMG CoA reductase inhibitors, cholestyramine, and fibrates. In another embodiment, the pharmaceutical composition may further comprise one or more therapeutic agents such as anti-cancer agents: such as, but not limited to, cyclophosphamide, nitrosoureas, carboplatin, cisplatin, procarbazine, Bleomycin, Daunorubicin, Doxorubicin, Methotrexate, Cytarabine, Fluorouracil, Vinblastine, Vincristine, Etoposide, Paclitaxel, Tamoxifen, Octreotide acetate, Finasteride, Flutamide, Interferons, Interleukins, and anti-tumor antibodies and antiangiogenic compounds and proteins.

In another embodiment, the present invention provides a method comprising: administering to a subject a pharmaceutical composition comprising a compound of Formula (I), wherein the compound of Formula (I) is a GalR1 agonist.

In another embodiment, the present invention provides a method comprising: administering a pharmaceutical composition to a subject having a disorder ameliorated by the activation of a GalR1 receptor, wherein the pharmaceutical composition comprises a compound of Formula (I) in an amount sufficient to increase activity of GalR1 in a subject. Diseases or disorders that may be treated with a GalR1 agonist include seizure disorders, neuroendocrine disorders, gastrointestinal disorders, musculoskeletal disorders, psychotic behavior such as schizophrenia, migraine, morphine tolerance, drug addition, particularly opiate addiction, pain, particularly neuropathic pain, inflammatory pain, chronic pain, sleep disorders, eating/body weight disorders such as bulimia, bulimia nervosa, and anorexia nervosa, metabolic wasting disorders such as cachexia, neuropathological disorders, diabetes, dyslipidimia, hypertension, memoryloss, depression, anxiety, cerebral hemorrhage, diarrhea, and one or more cancers such as, but not limited to, squamous cell carcinoma.

For example, the compounds and pharmaceutical compositions of the present invention comprising a GalR1 agonist may be useful in treating neuropathic pain. Further, at doses for which an analgesic effect may be observed, the compounds of the present invention may be capable of binding to at least one peripheral GalR1 while being substantially unable to cross the blood-brain barrier. Partial or complete exclusion of a GalR1 agonist from the brain may reduce the risk or severity of one or more centrally-mediated side effect associated with the administration of a GalR1 agonist to a subject.

It is contemplated within the scope of the invention that compounds of Formula (I) and that pharmaceutical compositions comprising a compound of Formula (I) may be formulated to treat disorders that are not associated with binding of galanin (or lack thereof) to the GalR1 receptor but where the symptoms of the disorder may be mediated by a GalR1 agonist.

The compounds of the present invention may be administered at a dosage level at about or below 1000 mg/kg of the body weight of the subject being treated. In another embodiment, the compounds of the present invention may be administered at a dosage level at about or below 100 mg/kg. In another embodiment, the compounds of the present invention may be administered at a dosage level at about or below 10 mg/kg of body weight per day. In another embodiment, the compounds of the present invention may be administered at a dosage level at about or above 0.01 mg/kg of body weight per day. In another embodiment, the compounds of the present invention may be admistered at a dosage level at about or above 0.5 mg/kg of body weight per day.

The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I) with an appropriate and convenient amount of carrier material that may vary from about 5 to 95 percent of the total composition. Dosage unit forms will generally contain between from about 5 mg to about 500 mg of active ingredient. The dosage may be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

In another embodiment, the pharmaceutical composition comprising a compound of Formula (I) may be administered to a subject in combination with one or more therapeutic agents selected from the group consisting of biologic response modifiers, analgesics, NSAIDs, DMARDs, glucocorticoids, sulfonylureas, biguanides, acarbose, PPAR agonists, DPP-IV inhibitors, GK activators, insulin, insulin mimetics, insulin secretagogues, insulin sensitizers, GLP-1, GLP-1 mimetics, cholinesterase inhibitors, antipsychotics, antidepressants, anticonvulsants, HMG CoA reductase inhibitors, cholestyramine, and fibrates. In another embodiment, the pharmaceutical composition comprising a compound of Formula (I) may be administered in a subject in combination with one or more therapeutic agents selected from the group consisting of anticancer agents such as, but not limted to, Cyclophosphamide, nitrosoureas, carboplatin, cisplatin, procarbazine, Bleomycin, Daunorubicin, Doxorubicin; Methotrexate, Cytarabine, Fluorouracil; Vinblastine, Vincristine, Etoposide, Paclitaxel; Tamoxifen, Octreotide acetate, Finasteride, Flutamide, Interferons, Interleukins, and anti-tumor antibodies and antiangiogenic compounds and proteins.

Neuropathic pain may be ameliorated, at least in part, by a GalR1 agonist binding to the peripheral GalR1 receptors in a subject. Where the GalR1 agonist is partially or completely prevented from passing through the blood-brain barrier, the risk of inducing centrally mediated central nervous system (CNS) side effects may be reduced or avoided. In an embodiment, the present invention provides a method of treating neuropathic pain in a subject that may avoid or reduce the risk of centrally mediated side effects in the subject. This method may be practiced with any GalR1 agonist that is substantially unable to cross the blood-brain barrier. Because peripheral GalR1 receptors in neuropathic pain may be associated with allodynia, this discovery provides a novel method of treating a subject in need of relief from allodynia by administering to the subject a GalR1 agonist of Formula (I) that is substantially unable to cross the blood-brain barrier. This method of treating allodynia may reduce or eliminate the risk of one or more centrally mediated CNS side effects.

In another embodiment, the present invention provides a method comprising: administering to a subject suffering from neuropathic pain a GalR1 agonist wherein the amount of GalR1 agonist is capable of stimulating peripheral GalR1 receptors in the subject and the GalR1 agonist is partially or completely excluded from the brain. In a further embodiment of the method, the GalR1 agonist comprises a compound of Formula (I).

In another embodiment, the present invention provides a method comprising: administering to a subject suffering from allodynia a GalR1 agonist in an amount capable of stimulating peripheral GalR1 receptors to induce an analgesic effect in the subject and wherein the GalR1 agonist is substantially unable to cross the blood-brain barrier at doses for which an analgesic effect is observed in the subject. In a further embodiment of the method, the GalR1 agonist comprises a compound of Formula (I).

In another embodiment, the present invention provides a method comprising: administering a GalR1 agonist to a subject suffering from neuropathic pain and modulating peripheral GalR1 receptors in the subject at the level of the dorsal root ganglia (DRG), wherein the GalR1 agonist is substantially unable to cross the blood-brain barrier in the subject at doses for which an analgesic effect is observed in the subject. In a further embodiment of the method, the GalR1 agonist comprises a compound of Formula (I).

In another embodiment, the present invention provides a method of treatment comprising: administering a compound of Formula (I) to a subject suffering from cancer. In another embodiment of the method of treatement, the cancer is squamous cell carcinoma. In another embodiment of the method of treatment, the compound of Formula (I) is administered in an amount effective to inhibit cancer cell proliferation in a subject. In another embodiment of the treatment, the compound of Formula (I) is administerd in an amount effective to inhibit or inactivate the MAPK pathway in cancer cells in the subject.

EXAMPLES

LC-MS data was obtained using gradient elution on a parallel MUX™ system, running four Waters 1525 binary HPLC pumps, equipped with a Mux-UV 2488 multichannel UV-Vis detector (recording at 215 and 254 nM) and a Leap Technologies HTS PAL Auto sampler using a Waters Xterra MS C18 4.6×50 mm column. A three minute gradient was run from 25% B (97.5% acetonitrile, 2.5% water, 0.05% TFA) and 75% A (97.5% water, 2.5% acetonitrile, 0.05% TFA) to 100% B. The system is interfaced with a Waters Micromass ZQ mass spectrometer using electrospray ionization. All MS data was obtained in the positive mode unless otherwise noted. $^1$H NMR data was obtained on a Varian 400 MHz spectrometer.

Abbreviations used in the Examples are as follows:
APCI=atmospheric pressure chemical ionization
BOC=tert-butoxycarbonyl
BOP=(1-benzotriazolyloxy)tris(dimethylamino)phosphonium hexafluorophosphate
d=day
DIAD=diisopropyl azodicarboxylate
DCC=dicyclohexylcarbodiimide
DCM=dichloromethane
DIC=diisopropylcarbodiimide
DIEA=diisopropylethylamine
DMA=N,N-dimethylacetamide
DMAP=dimethylaminopyridine
DME=1,2 dimethoxyethane
DMF=N,N-dimethylformamide
DMPU=1,3-dimethypropylene urea
DMSO=dimethylsulfoxide
EDC=1-ethyl-3-(3-dimethylaminopropyl)-carbodiimide hydrochloride
EDTA=ethylenediamine tetraacetic acid
ELISA=enzyme-linked immunosorbent assay
ESI=electrospray ionization
ether=diethyl ether
EtOAc=ethyl acetate
FBS=fetal bovine serum
g=gram
h, hr=hour
HBTU=O-benzotriazol-1-yl-N,N,N',N'-tetramethyluronium hexafluorophosphate
HMPA=hexamethylphosphoric triamide
HOBt=1-hydroxybenzotriazole
Hz=hertz
i.v.=intravenous
kD=kiloDalton
L=liter
LAH=lithium aluminum hydride
LDA=lithium diisopropylamide
LPS=lipopolysaccharide
M=molar
m/z=mass to charge ratio
mbar=millibar
MeOH=methanol
mg=milligram
min=minute
mL=milliliter
mM=millimolar
mmol=millimole
mol=mole mp=melting point
MS=mass spectrometry
N=normal
NMM=N-methylmorpholine, 4-methylmorpholine
NMR=nuclear magnetic resonance spectroscopy
p.o.=per oral
PBS=phosphate buffered saline solution
PMA=phorbol myristate acetate
ppm=parts per million
psi=pounds per square inch
$R_f$=relative TLC mobility
rt, RT=room temperature
s.c.=subcutaneous
SPA=scintillation proximity assay
TEA=triethylamine
TFA=trifluoroacetic acid
THF=tetrahydrofuran
THP=tetrahydropyranyl
TLC=thin layer chromatography
TMSBr=bromotrimethylsilane, trimethylsilylbromide
$T_r$=retention time Example A N-(2-Aminophenyl)-2-methoxy-5-trifluoromethane-sulfonylbenzenesulfonamide To a solution of 2-methoxy-5-trifluoromethanesulfonyl-1-benzenesulfonyl chloride (5 g) in dry dichloromethane (10 mL), benzene-1,2-diamine (5 g) was added followed by addition of dry pyridine (10 mL) at 0° C. The resulting deep red reaction mixture was then stirred at room temperature for 4 h. The reaction mixture was diluted with dichloromethane (250 mL). The contents were washed with saturated aqueous sodium chloride solution (50 mL) and saturated aqueous sodium carbonate solution (50 mL). The organic phase was dried over sodium sulfate and concentrated under vacuum. The residue obtained was purified by flash column chromatography eluting with DCM/EtOAc (7:1 to 4:1) to give N-(2-aminophenyl)-2-methoxy-5-trifluoromethanesulfonylbenzenesulfonamide (6 g). LC: $T_r$ 0.95 min, MS: 411 (M+1)$^+$. $^1$H NMR (CDCl$_3$, 400 MHz): δ 4.18 (bs, 2H), 4.21 (s, 3H), 6.43 (m, 2H), 6.57 (bs, 1H), 6.75 (dd, 1H), 7.02 (t, 1H), 7.35 (d, 1H), 8.22 (dd, 1H), 8.40 (d, 1H) ppm.

Example B

2-Methoxy-5-nitrobenzenesulfonyl chloride

To a solution of 4-nitroanisole (3.1 g; 20 mmol) in 1,2-dichloroethane (20 mL), 2 mL of chlorosulfonic acid was added at 0° C. The resulting reaction mixture was gradually warmed to room temperature and then heated to reflux for 2 h at which time all the anisole had been consumed. The reaction mixture was then cooled to room temperature and diluted with chloroform (30 mL). The contents were then transferred to a separatory funnel, washed with water (50 mL), and the layers were separated. The aqueous layer was then extracted with chloroform (30 mL). The combined organic layers was washed with brine (50 mL) and dried over anhydrous sodium sulfate. The solvent was removed in vacuo and the residue obtained was purified by silica gel flash column chromatography using ethyl acetate/hexanes as eluant (1:5 to 1:1 gradient) to afford 2-methoxy-5-nitrobenzenesulfonyl chloride as a dark brown solid. $^1$H NMR (CDCl$_3$, 400 MHz): δ 4.21 (s, 3H), 7.28 (d, 1H), 8.59 (dd, 1H), 8.88 (d, 1H) ppm.

Example 1

To a solution of o-phenylenediamine (5 mmol) in DCM (25 mL) and pyridine (5 mL) at 0° C., benzo[b]thiophene-2-sulfonyl chloride (5.5 mmol) was added in small portions. The reaction mixture was then gradually warmed to RT with stirring continued until the reaction was complete as determined by TLC or LC-MS. The reaction mixture was then diluted with DCM (25 mL). The organic phase was washed with water (2×25 mL) and 25 mL of brine. The organic phase was dried over anhydrous sodium sulfate, and concentrated under vacuum. The residue obtained was purified by flash column chromatography eluting with DCM/EtOAc to give 1.2 g of benzo[b]thiophene-2-sulfonic acid (2-amino-phenyl)-amide. $T_r$ 0.94 min, MS: 305.7 (M+1)$^+$. $^1$H NMR (DMSO-d$_6$, 400 MHz): δ 6.40 (t, 1H), 6.60 (d, 1H), 6.78 (d, 1H), 6.89 (t, 1H), 7.45 (t, 1H), 7.50 (t, 1H), 7.80 (s, 1H), 7.90 (d, 1H), 8.80 (d, 1H) ppm.

The monosulfonamide (2 mmol) obtained as above was dissolved in DCM (4 mL) and pyridine (4 mL). 2-Chloro-5-(trifluoromethyl)benzenesulfonyl chloride (2.2 mmol) was then added at RT and the reaction mixture was then allowed to stir at RT overnight or until the reaction was complete as determined by TLC or LC-MS. The reaction mixture was then diluted with DCM (10 mL). The organic phase was washed with 10% HCl aqueous solution (10 mL), water (10 mL) and brine (10 mL). The organic phase was dried over anhydrous sodium sulfate, and concentrated under vacuum. The residue obtained was purified by flash column chromatography eluting with DCM/EtOAc to obtain 710 mg of benzo[b]thiophene-2-sulfonic acid [2-(2-chloro-5-trifluoromethyl-benzenesulfonylamino)phenyl]-amide. $T_r$ 1.2 min, MS: 547.6 (M+1)$^+$. $^1$H NMR (DMSO-d$_6$, 400 MHz): δ 7.0-7.2 (m, 4H), 7.48 (dd, 1H), 7.53 (dd, 1H), 7.90 (d, 1H), 7.92 (d, 1H), 7.98 (d, 1H), 8.02-8.06 (m, 3H), 9.74 (bs, 1H), 9.88 (bs, 1H) ppm.

Example 2

To a solution of 4-methoxybenzenethiol (10 mmol) in dry THF (50 mL), solid t-BuOK (12 mmol) was added at 0° C. in small portions. The reaction mixture was stirred for 30 min followed by dropwise addition of 2-bromopropane (1.6 g) at 0° C. The reaction mixture was then stirred for 1 h at room temperature and was heated at 60° C. for 1 h. After cooling to the room temperature, the reaction was diluted with ethyl acetate (250 mL). The organic phase was washed with water (50 mL) and then with saturated sodium chloride aqueous solution (100 mL). The organic layer was dried over anhydrous sodium sulfate and concentrated under vacuum. The crude 1-isopropylsulfanyl-4-methoxybenzene (10 mmol) was used for further transformation without any purification.

To a solution of the aforementioned crude 1-isopropylsulfanyl-4-methoxybenzene (ca. 10 mmol) in DCM (20 ml), 32% aqueous ethaneperoxoic acid solution (7 mL) was added at 0° C. The reaction mixture was then stirred at room temperature for 2 h then diluted with ethyl acetate (150 mL). The organic phase was washed with water (50 mL) and 1% aqueous KOH solution (75 mL). The organic phase was then dried over anhydrous sodium carbonate and concentrated under vacuum to furnish 2 g of crude 1-methoxy-4-(propane-2-sulfonyl)-benzene as a pale yellow oil. $^1$H NMR (CDCl$_3$, 400 MHz): δ 1.28 (d, 6H), 3.16 (m, 1H), 3.89 (s, 3H), 7.02 (d, 2H), 7.80 (d, 2H) ppm.

To a solution of crude 1-methoxy-4-(propane-2-sulfonyl) benzene (8 mmol) in dry dichloromethane (20 mL), chlorosulfonic acid (1 mL) was added dropwise at 0° C. The reaction mixture was warmed to room temperature followed by the addition of PCl$_5$ (0.5 g). The resulting reaction mixture was refluxed for 1 h. After cooling to room temperature, the reaction mixture was poured into ice water (50 mL) with vigorous stirring. The aqueous layer was then extracted with EtOAc (2×75 mL). The combined organic extracts was washed with saturated sodium chloride aqueous solution (2×50 mL), dried over anhydrous sodium sulfate, and concentrated under vacuum. The residue was purified by flash column chromatography eluting with hexanes/EtOAc (3:1) to give 1.25 g of 2-methoxy-5-(propane-2-sulfonyl)benzenesulfonyl chloride. $^1$H NMR (CDCl$_3$, 400 MHz): δ 1.31 (d, 1H), 3.23 (m, 1H), 4.18 (s, 3H), 7.30 (d, 1H), 8.18 (dd, 1H). 8.46 (d, H) ppm.

To a solution of benzo[b]thiophene-2-sulfonic acid (2-aminophenyl)-amide (1 mmol) (prepared as in example 1) in DCM (2 mL) and pyridine (2 mL), 2-methoxy-5-(propane-2-sulfonyl)benzenesulfonyl chloride (1.1 mmol) was added at RT and the reaction mixture was then allowed to stir at RT overnight. The reaction mixture was then diluted with DCM (10 mL). The organic phase was washed with 10% aqueous HCl (10 mL), water (10 mL) and brine (10 mL). The organic phase was dried over anhydrous sodium sulfate, and concentrated under vacuum. The residue obtained was purified by flash column chromatography eluting with DCM/EtOAc to obtain 460 mg of benzo[b]thiophene-2-sulfonic acid {2-[2-methoxy-5-(propane-2 sulfonyl) benzenesulfonylamino] phenyl-amide. T$_r$ 1.09 min; MS: 581.4 (M+1)$^+$. $^1$H NMR (DMSO-d$_6$, 400 MHz): δ 0.97 (d, 6H), 3.58 (m, 1H), 4.02 (s, 3H), 6.84 (dd, 1H), 7.96 (td, 1H), 7.10 (td, 1H), 7.23 (dd, 1H), 7.44-7.54 (m, 3H), 7.86 (d, 1H), 7.90 (s, 1H), 7.96 (d, 1H), 8.03 (dd, 2H), 9.22 (bs, 1H), 9.79 (s, 1H) ppm.

Example 3

To a solution of benzo[b]thiophene-2-sulfonic acid (2-aminophenyl)-amide (1 mmol) in DCM (2 mL) and pyridine (2 mL), methyl 3-(chlorosulfonyl)-4-methoxybenzoate (1.1 mmol) was added at RT and the reaction mixture was then allowed to stir at RT overnight. The reaction mixture was then diluted with DCM (10 mL). The organic phase was washed with 10% aqueous HCl (10 mL), water (10 mL) and brine (10 mL). The organic phase was dried over anhydrous sodium sulfate, and concentrated under vacuum. The residue obtained was purified by flash column chromatography eluting with DCM/EtOAc to obtain 350 mg of 3-[2-(benzo[b]thiophene-2-sulfonylamino)phenylsulfamoyl]-4-methoxy-benzoic acid methyl ester. T$_r$ 1.10 min, MS: 533.7 (M+1)$^+$. $^1$H NMR (CDCl$_3$, 400 MHz): δ 3.84 (s, 3H), 4.18 (s, 3H), 7.0-7.2 (m, 5H), 7.4-7.6 (m, 3H), 7.66 (s, 1H), 7.80 (d, 1H), 7.83 (d, 1H), 8.22 (dd, 1H), 8.34 (d, 1H) ppm.

Example 4

To a solution of 3-[2-(Benzo[b]thiophene-2-sulfonylamino)-phenyl sulfamoyl]-4-methoxy-benzoic acid methyl ester (5 mmol, obtained as in Example 3) in THF (10 mL) and methanol (10 mL), 4 M aq. NaOH (5 mL) was added at RT. The reaction mixture was stirred at room temperature till the reaction was complete. The reaction mixture was then concentrated in vacuo and acidified with 10% aq. HCl to pH ~3. A white precipitate was formed which was filtered, washed with ether and dried, affording 2.5 g of 3-[2-(benzo[b]thiophene-2-sulfonylamino)-phenylsulfamoyl]-4-methoxy-benzoic acid. MS: 519.8 (M+1)$^+$. $^1$H NMR (DMSO-d$_6$, 400 MHz): δ 4.05 (s, 3H), 6.89 (d, 1H), 6.99 (dd, 1H), 7.11 (dd, 1H), 7.25 (d, 1H), 7.38 (d, 1H), 7.48 (dd, 1H), 7.53 (dd, 1H), 7.91 (s, 1H), 7.98 (d, 1H), 8.65 (d, 1H), 8.13 (dd, 1H), 8.16 (dd, 1H) ppm.

Example 5

To a solution of N-(2-aminophenyl)-2-methoxy-5-trifluoromethanesulfonylbenzenesulfonamide (2 mmol, prepared as in Example A) in DCM (4 mL) and pyridine (4 mL), 3-nitrobenzenesulfonyl chloride (2.2 mmol) was added at RT and the reaction mixture was then allowed to stir at RT. The reaction mixture was then diluted with DCM (20 mL). The organic phase was washed with 10% aqueous HCl (20 mL), water (20 mL) and brine (20 mL). The organic phase was dried over anhydrous sodium sulfate and concentrated under vacuum. The residue obtained was purified by flash column chromatography eluting with DCM/EtOAc to afford 1.04 g of 2-methoxy-N-[2-(3-nitrobenzenesulfonylamino)phenyl]-5-trifluoromethanesulfonylbenzenesulfonamide. LC: T$_r$ 1.17 min, MS: 596.6 (M+1)$^+$. $^1$H NMR (CDCl$_3$, 400 MHz): δ 4.27 (s, 3H), 6.76 (d, 1H), 6.78(bs, 1H), 7.05 (m, 1H), 7.16 (m, 2H), 7.34 (d, 1H), 7.68 (bs, 1H), 7.72 (t, 1H), 8.01 (dd, 1H), 8.20 (dd, 1H), 8.25 (d, 1H), 8.46 (dd, 1H), 8.55 (d, 1H) ppm.

To a solution of the bissulfonamide (1 mmol) obtained as above in AcOH (5 mL), iron powder (300 mg) was added and the resulting reaction mixture was heated at 100° C. for 30 min. The reaction mixture was filtered through a short pad of Celite and the pad was washed with methanol (50 mL) and dichloromethane (25 mL). The filtrate was concentrated under vacuum. The residue obtained was dissolved in EtOAc (50 mL) and washed with of 1% aqueous KOH solution (25 mL). The organic layer was dried over anhydrous sodium sulfate and the solvent was removed to dryness in vacuo to give 155 mg of crude N-[2-(3-amino-benzenesulfonylamino) - phenyl]-2-methoxy-5-trifluoro methanesulfonyl-benzenesulfonamide. LC: T$_r$ 1.09 min; MS: 566.4 (M+1)$^+$.

To a solution of the amino intermediate (0.5 mmol) obtained as above in AcOH (2 mL) was added NH$_4$OAc (10 mmol), 37% aqueous formaldehyde solution (2 mL), and 40% aqueous glyoxal (1 mL). The reaction mixture was heated at 100° C. for 1.5 h. After cooling to room temperature, the reaction mixture was diluted with ethyl acetate (50 mL). The organic phase was washed with water (25 mL) and 1% aqueous KOH solution (25 mL). The organic phase was dried over sodium sulfate and concentrated under vacuum. The residue was purified by flash column chromatography eluting with EtOAc then ethyl acetate/methanol (100:2 to 100:10) to afford 155 mg of N-[2-(3-imidazol-1-yl-benzenesulfonylamino)phenyl]-2-methoxy-5-trifluoromethanesulfonyl-benzenesulfonamide. LC: T$_r$ 0.90 min; MS: 617.7 (M+1)$^+$. $^1$H NMR (CDCl$_3$, 400 MHz): δ 4.15 (s, 3H), 6.75 (d, 1H), 7.01 (bs, 1H), 7.05 (t, 1H), 7.17 (t, 1H), 7.30 (m 5H), 7.53 (m, 3H), 7.73 (d, 2H), 8.04 (dd, 1H), 8.25 (d, 1H) ppm.

Example 6

To a solution of N-(2-amino-phenyl)-2-methoxy-5-trifluoromethane sulfonylbenzenesulfonamide (1 mmol, prepared as in Example 3) in DCM (2 mL) and pyridine (2 mL), 4-nitrobenzenesulfonyl chloride (1.1 mmol) was added at RT and the reaction mixture was then allowed to stir at RT overnight. The reaction mixture was then diluted with DCM (10 mL). The organic phase was washed with 10% aqueous HCl (10 mL), water (10 mL) and brine (10 mL). The organic phase was dried over anhydrous sodium sulfate, and concentrated under vacuum. The residue obtained was purified by flash column chromatography eluting with DCM/EtOAc to afford 446 mg of 2-methoxy-N-[2-(4-nitrobenzenesulfonylamino) phenyl]-5-trifluoromethanesulfonyl benzenesulfonamide. LC: $T_r$ 1.15 min, MS: 596.8 (M+1)$^+$. $^1$H NMR (CDCl$_3$, 400 MHz): δ 4.27 (s, 3H), 6.79 (d, 1H), 6.83 (bs, 1H), 7.07 (m, 1H), 7.17 (m, 2H), 7.34 (d, 1H), 7.59 (bs, 1H), 7.90 (d, 2H), 8.20 (t, 1H), 8.25 (d, 1H), 8.30 (d, 2H) ppm.

To a solution of the 2-methoxy-N-[2-(4-nitrobenzenesulfonylamino)phenyl]-5-trifluoromethanesulfonylbenzenesulfonamide (1 mmol) in AcOH (5 mL), iron powder (300 mg) was added and the resulting reaction mixture was heated at 100° C. for 30 min. The reaction mixture was filtered through a short pad of Celite and the pad was washed with methanol (50 mL) and dichloromethane (25 mL). The filtrate was concentrated under vacuum. The residue obtained was dissolved in EtOAc (50 mL) and washed with 1% aqueous KOH solution (25 mL). The organic layer was dried over anhydrous sodium sulfate and the solvent was removed to dryness in vacuo to give 486 mg of crude N-[2-(4-aminobenzenesulfonylamino)-phenyl]-2-methoxy-5-trifluoro methanesulfonyl-benzenesulfonamide. LC: $T_r$ 1.09 min; MS: 566.7 (M+1)$^+$.

To a solution of the amino intermediate (0.5 mmol) obtained as above in AcOH (2 mL) was added NH$_4$OAc (10 mmol), 37% aqueous formaldehyde solution (2 mL), and 40% aqueous glyoxal (1 mL). The reaction mixture was heated at 100° C. for 1.5 h. After cooling to room temperature, the reaction mixture was diluted with ethyl acetate (50 mL). The organic phase was washed with water (25 mL) and 1% KOH aqueous solution (25 mL). The organic phase was dried over sodium sulfate and concentrated under vacuum. The residue was purified by flash column chromatography eluting with EtOAc then ethyl acetate/methanol (100:2 to 100:10) to afford 200 mg of N-[2-(4-imidazol-1-yl-benzenesulfonylamino)phenyl]-2-methoxy-5-trifluoromethanesulfonyl-benzenesulfonamide. LC: $T_r$ 0.90 min; MS: 617.6 (M+1)$^+$. $^1$H NMR (CDCl$_3$, 400 MHz): δ 4.16 (s, 3H), 6.81 (d, 1H), 7.05 (m, 2H), 7.14 (m, 2H), 7.24 (m, 3H), 7.43 (d, 2H), 7.55 (bs, 1H), 7.75 (d, 2H), 7.83 (s, 1H), 8.06 (dd, 1H), 8.25 (d, 1H) ppm.

Example 7

To a solution of of N-(2-aminophenyl)-2-methoxy-5-trifluoromethanesulfonylbenzenesulfonamide (0.5 mmol, prepared as in Example A) in DCM (1 mL) and pyridine (1 mL), 5-chloro-3-methylbenzo[b]thiophene-2-sulfonyl chloride (0.55 mmol) was added at RT and the reaction mixture was then allowed to stir at RT overnight. The reaction mixture was then diluted with DCM (5 mL). The organic phase was washed with 10% aqueous HCl (5 mL), water (5 mL) and brine (5 mL). The organic phase was dried over anhydrous sodium sulfate and concentrated under vacuum. The residue obtained was purified by flash column chromatography eluting with DCM/EtOAc to afford 202 mg of 5-chloro-3-methylbenzo[b]thiophene-2-sulfonic acid [2-(2-methoxy-5-trifluoromethanesulfonyl-benzenesulfonylamino)phenyl]-amide. LC: $T_r$ 1.32 min, MS: 655.4 (M+1)$^+$. $^1$H NMR (CDCl$_3$, 400 MHz): δ 2.14 (s, 3H), 4.29 (s, 3H), 6.33 (bs, 1H), 6.54 (d, 1H), 6.98 (t, 1H), 7.24 (t, 1H), 7.35 (d, 1H), 7.45 (dd, 1H), 7.49 (dd, 1H), 7.70 (d, 1H), 7.75 (d, 1H), 8.14 (bs, 1H), 8.17 (dd, 1H), 8.31(d, 1H) ppm.

Example 8

To a solution of o-phenylenediamine (5 mmol) in DCM (25 mL) and pyridine (5 mL) at 0° C., 5-bromo-2-methoxybenzenesulfonyl chloride (5.5 mmol) was added in small portions. The reaction mixture was then gradually warmed to RT with stirring continued until the reaction was complete as determined by TLC or LC-MS. The reaction mixture was then diluted with DCM (25 mL). The organic phase was washed with water (2×25 mL) and 25 mL of brine. The organic phase was dried over anhydrous sodium sulfate, and concentrated under vacuum. The residue obtained was purified by flash column chromatography eluting with DCM/EtOAc to give 1.07 g of N-(2-aminophenyl)-5-bromo-2-methoxybenzene sulfonamide. $^1$H NMR (CDCl$_3$, 400 MHz): δ 4.08 (s, 3H), 4.22(bs, 2H), 6.52 (m, 2H), 6.75 (m, 2H), 7.01 (d, 1H), 7.03 (m, 1H), 7.65(dd, 1H), 7.88 (d, 1H) ppm.

The monosulfonamide (1 mmol) obtained as above was dissolved in DCM (2 mL) and pyridine (2 mL). Benzo[b]thiophene-2-sulfonyl chloride (1.1 mmol) was then added at RT and the reaction mixture was then allowed to stir at RT overnight. The reaction mixture was then diluted with DCM (10 mL). The organic phase was washed with 10% aqueous HCl (10 mL), water (10 mL) and brine (10 mL). The organic phase was dried over anhydrous sodium sulfate, and concentrated under vacuum. The residue obtained was purified by flash column chromatography eluting with DCM/EtOAc to give 390 mg of benzo[b]thiophene-2-sulfonic acid [2-(5-bromo-2-methoxybenzene sulfonylamino)phenyl]-amide. LC: $T_r$ 1.19 min, MS: 553.5 (M+)$^+$. $^1$H NMR (CDCl$_3$, 400 MHz): δ 4.11 (s, 3H), 7.00 (d, 1H), 7.1-7.2 (m, 5H), 7.47 (m, 2H), 7.62 (d, 1H), 7.64 (d, 1H), 7.68 (s, 1H), 7.78 (d, 1H), 7.84 (dd, 2H) ppm.

Example 9

To a solution of N-(2-aminophenyl)-5-bromo-2-methoxybenzene sulfonamide (0.5 mmol; prepared as in Example 7) in DCM (1 mL) and pyridine (1 mL), 4,5-dichlorothiophene-2-sulfonyl chloride (0.55 mmol) was added at RT and the reaction mixture was then allowed to stir at RT overnight. The reaction mixture was then diluted with DCM (5 mL). The organic phase was washed with 10% aqueous HCl (5 mL), water (5 mL) and brine (5 mL). The organic phase was dried over anhydrous sodium sulfate and concentrated under vacuum. The residue obtained was purified by flash column chromatography eluting with DCM/EtOAc to afford 214 mg of 4,5-dichlorothiophene-2-sulfonic acid [2-(5-bromo-2-methoxybenzenesulfonylamino)-phenyl]-amide. LC: $T_r$ 1.30 min, MS: 572.8 (M+1)$^+$. $^1$H NMR (CDCl$_3$, 400 MHz): δ 4.12 (s, 3H), 7.00 (d, 1H), 7.10 (d, 1H), 7.12 (dd, 1H), 7.22 (dd, 1H), 7.23-7.32 (m, 3H), 7.66 (dd, 1H), 7.70 (d, 1H) ppm.

Example 10

To a solution of of N-(2-aminophenyl)-5-bromo-2-methoxybenzenesulfonamide (0.5 mmol; prepared as in Example 7) in DCM (1 mL) and pyridine (1 mL), 5-isoxazol-3-yl-thiophene-2-sulfonyl chloride (0.55 mmol) was added at RT and the reaction mixture was then allowed to stir at RT overnight. The reaction mixture was then diluted with DCM (5 mL). The organic phase was washed with 10% aqueous HCl (5 mL), water (5 mL) and brine (5 mL). The organic phase was dried over anhydrous sodium sulfate and concentrated under vacuum. The residue obtained was purified by flash column chromatography eluting with DCM/EtOAc to afford 140 mg of 5-isoxazol-3-yl-thiophene-2-sulfonic acid [2-(5-bromo-2-methoxy-benzenesulfonylamino)phenyl]-amide. LC: $T_r$ 1.15 min, MS: 572.0 (M+1)$^+$. $^1$H NMR (CDCl$_3$, 400 MHz): δ 4.10 (s, 3H), 6.51 (s, 1H), 6.99 (d, 1H), 7.04 (d, 1H), 7.11 (dd, 1H), 7.18 (dd, 12H), 7.25 (dd, 1H), 7.40 (d, 1H), 7.46 (d, 1H), 7.54 (dd, 1H), 7.64 (dd, 1H), 7.75 (dd, 1H), 8.31 (s, 1H) ppm.

Example 11

To a solution of o-phenylenediamine (4 mmol) in DCM (20 mL) and pyridine (4 mL) at 0° C., 4-chlorobenzenesulfonyl chloride (4.4 mmol) was added in small portions. The reaction mixture was then gradually warmed to RT with stirring continued until the reaction was complete as determined by TLC or LC-MS. The reaction mixture was then diluted with DCM (20 mL). The organic phase was washed with water (2×20 mL) and 20 mL of brine. The organic phase was dried over anhydrous sodium sulfate and concentrated under vacuum. The residue obtained was purified by flash column chromatography eluting with DCM/EtOAc to give 960 mg of N-(2-aminophenyl)-4-chlorobenzenesulfonamide. LC: $T_r$ 0.92 min, MS: 284.0 (M+1)$^+$.

The monosulfonamide (1 mmol) obtained as above was dissolved in DCM (2 mL) and pyridine (2 mL). 2-methoxy-5-nitrobenzenesulfonyl chloride (1.1 mmol, prepared as in Example B) was then added at RT and the reaction mixture was then allowed to stir at RT overnight. The reaction mixture was then diluted with DCM (10 mL). The organic phase was washed with 10% aqueous HCl (10 mL), water (10 mL) and brine (10 mL). The organic phase was dried over anhydrous sodium sulfate, and concentrated under vacuum. The residue obtained was purified by flash column chromatography eluting with DCM/EtOAc to give 325 mg of N-[2-(4-chlorobenzenesulfonylamino)phenyl]-2-methoxy-5-nitrobenzenesulfonamide. LC: $T_r$ 1.2 min, MS: 498.1 (M+1)$^+$.

Example 12

To a solution of benzofuran (10 mmol) in dry THF (15 mL) at −40° C., n-BuLi (2.5 M in hexanes; 4.4 mL; 11 mmol) was added dropwise. The reaction mixture was stirred at −40° C. for 30-40 min. Sulfur dioxide gas was passed into the reaction mixture, keeping the tip of the needle just above the reaction mixture, for about 5-10 min. A white precipitate was formed. The reaction mixture was then brought to RT and the stirring was continued for 1 h, then the mixture was diluted with hexane (20 mL) to give benzofuran-2-sulfinic acid lithium salt as a white precipitate. The solid was filtered and dried in vacuo to afford the salt.

The solid obtained as above was suspended in DCM (50 mL) and was treated with N-chlorosuccinimide (11 mmol) at 0° C. The resulting suspension was then brought to RT with stirring maintained vigorously overnight. The dark brown reaction mixture was filtered and washed with DCM. The filtrate was concentrated in vacuo and the residue obtained was purified through silica gel column chromatography using EtOAc/hexane as eluant to furnish 1.19 g of benzofuran-2-sulfonyl chloride as a pale brown solid.

To a solution of N-(2-aminophenyl)-4-chlorobenzenesulfonamide (0.5 mmol, prepared as in Example 11) in DCM (1 mL) and pyridine (1 mL), benzofuran-2-sulfonyl chloride (0.55 mmol), prepared as above, was added at RT and the reaction mixture was then allowed to stir at RT overnight or until the reaction was complete as determined by TLC or LC-MS. The reaction mixture was then diluted with DCM (5 mL). The organic phase was washed with 10% aqueous HCl (5 mL), water (5 mL) and brine (5 mL). The organic phase was dried over anhydrous sodium sulfate, and concentrated under vacuum. The residue obtained was purified by flash column chromatography eluting with DCM/EtOAc to afford 92 mg benzofuran-2-sulfonic acid [2-(4-chlorobenzenesulfonylamino)phenyl]-amide. LC: $T_r$ 1.13 min, MS: 464.0 (M+1)$^+$.

Example 13

To a solution of N-(2-aminophenyl)-4-chlorobenzenesulfonamide (0.5 mmol, prepared as in Example 11) in DCM (1 mL) and pyridine (1 mL), benzo[b]thiophene-2-sulfonyl chloride (0.55 mmol), prepared as above, was added at RT and the reaction mixture was then allowed to stir at RT overnight or until the reaction was complete as determined by TLC or LC-MS. The reaction mixture was then diluted with DCM (5 mL). The organic phase was washed with 10% HCl aqueous solution (5 mL), water (5 mL) and brine (5 mL). The organic phase was dried over anhydrous sodium sulfate and concentrated under vacuum. The residue obtained was purified by flash column chromatography eluting with DCM/EtOAc to afford 180 mg of benzo[b]thiophene-2-sulfonic acid [2-(4-chlorobenzenesulfonylamino)phenyl]-amide. LC: $T_r$ 1.23 min, MS: 479.8 (M+1)$^+$.

Example 14

To a solution of 1-methoxy-4-methylsulfanylbenzene (10 mmol) in DCM (20 ml), 32% aqueous ethaneperoxoic acid solution (7 mL) was added at 0° C. The reaction mixture was then stirred at room temperature for 2 h then diluted with ethyl acetate (100 mL). The organic phase was washed with water (50 mL) and 1% aqueous KOH solution (75 mL). The organic phase was then dried over anhydrous sodium carbonate and concentrated under vacuum to furnish 1.5 g of crude 1-methanesulfonyl-4-methoxybenzene as an off-white solid.

To a solution of crude 1-methanesulfonyl-4-methoxybenzene (8 mmol) in dry dichloromethane (20 mL), chlorosulfonic acid (1 mL) was added dropwise at 0° C. The reaction mixture was warm to room temperature followed by the addition of $PCl_5$ (0.5 g). The resulting reaction mixture was refluxed for 1 h. After cooling to room temperature, the reaction mixture was poured into stirring ice water (50 mL). The water layer was then extracted with EtOAc (2×40 mL.) The combined organic extracts was washed with saturated sodium chloride aqueous solution (2×40 mL), dried over anhydrous sodium sulfate, and concentrated under vacuum. The residue was purified by flash column chromatography eluting with hexanes/EtOAc (3:1) to give 1.6 g of 5-methanesulfonyl-2-methoxybenzenesulfonyl chloride.

To a solution of N-(2-aminophenyl)-4-chlorobenzenesulfonamide (0.5 mmol, prepared as in Example 11) in DCM (1 mL) and pyridine (1 mL), 5-methanesulfonyl-2-methoxybenzenesulfonyl chloride (0.55 mmol), prepared as above, was added at RT and the reaction mixture was then allowed to stir at RT overnight. The reaction mixture was then diluted with DCM (5 mL). The organic phase was washed with 10% aqueous HCl (5 mL), water (5 mL), and brine (5 mL). The organic phase was dried over anhydrous sodium sulfate, and concentrated under vacuum. The residue obtained was purified by flash column chromatography eluting with DCM/EtOAc to afford 160 mg of; N-[2-(4-chlorobenzenesulfonylamino)phenyl]-5-methanesulfonyl-2-methoxybenzenesulfonamide. LC: $T_r$ 1.05 min, MS: 531.9 (M+1)$^+$.

Example 15

To a solution of benzo[b]thiophene-2-sulfonic acid (2-aminophenyl) amide (1 mmol, prepared as in Example 1) in DCM (2 mL) and pyridine (2 mL), 4-methoxy-2-nitrobenzenesulfonyl chloride (1.1 mmol) was added at RT and the reaction mixture was then allowed to stir at RT overnight. The reaction mixture was then diluted with DCM (10 mL). The organic phase was washed with 10% aqueous HCl (10 mL), water (10 mL) and brine (10 mL). The organic phase was dried over anhydrous sodium sulfate and concentrated under vacuum. The residue obtained was purified by flash column chromatography eluting with DCM/EtOAc to obtain 348 mg of benzo[b]thiophene-2-sulfonic acid [2-(4-methoxy-2-nitro-benzenesulfonylamino)phenyl]-amide. LC: $T_r$ 1.09 min; MS: 520.7 $(M+1)^+$.

Example 16

To a solution of benzo[b]thiophene-2-sulfonic acid (2-amino-phenyl)-amide (1 mmol, prepared as in Example 1) in DCM (2 mL) and pyridine (2 mL), 5-methanesulfonyl-2-methoxybenzenesulfonyl chloride (1.1 mmol) was added at RT and the reaction mixture was then allowed to stir at RT overnight. The reaction mixture was then diluted with DCM (10 mL). The organic phase was washed with 10% aqueous HCl (10 mL), water (10 mL) and brine (10 mL). The organic phase was dried over anhydrous sodium sulfate and concentrated under vacuum. The residue obtained was purified by flash column chromatography eluting with DCM/EtOAc to obtain 330 mg of benzo[b]thiophene-2-sulfonic acid [2-(4-methanesulfonyl-2-methoxy-benzenesulfonylamino)phenyl]-amide. LC: $T_r$ 1.06 min; MS: 553.8 $(M+1)^+$.

Example 17

To a solution of benzo[b]thiophene-2-sulfonic acid (2-aminophenyl)-amide (1 mmol, prepared as in Example 1) in DCM (2 mL) and pyridine (2 mL), 2-methoxy-5-methylbenzenesulfonyl chloride (1.1 mmol) was added at RT and the reaction mixture was then allowed to stir at RT overnight. The reaction mixture was then diluted with DCM (10 mL). The organic phase was washed with 10% aqueous HCl (10 mL), water (10 mL) and brine (10 mL). The organic phase was dried over anhydrous sodium sulfate and concentrated under vacuum. The residue obtained was purified by flash column chromatography eluting with DCM/EtOAc to obtain 390 mg of benzo[b]thiophene-2-sulfonic acid [2-(2-methoxy-5-methylbenzenesulfonylamino)phenyl]-amide. LC: $T_r$ 1.25 min; MS: 489.1 $(M+1)^+$.

Example 18

To a solution of benzo[b]thiophene-2-sulfonic acid [2-(2-chloro-5-trifluoromethylbenzenesulfonylamino)phenyl]-amide (0.5 mmol) in dioxane (5 mL), solid sodium methoxide (2 mmol) was added in one portion and the resulting reaction mixture was then heated to reflux for ca. 4 h. After the completion of the reaction, the reaction mixture was cooled to RT and concentrated in vacuo. The residue obtained was redissolved in EtOAc (10 mL) and was washed with water (10 mL) and brine (10 mL). The organic phase was dried over anhydrous sodium sulfate and concentrated under vacuum. The residue obtained was purified by flash column chromatography eluting with DCM/EtOAc to obtain 204 mg of benzo[b]thiophene-2-sulfonic acid [2-(2-methoxy-5-trifluoromethylbenzenesulfonylamino)phenyl]-amide. LC: $T_r$ 1.20 min; MS: 544.1 $(M+1)^+$.

Example 19

To a solution of 2-(4-methoxybenzenesulfonyl)ethanol (20 mmol) in dry DCM (20 mL), triethylamine (4 mL) was added. The reaction mixture was cooled to 0° C. followed by dropwise addition of methanesulfonyl chloride (3 mL). The reaction mixture was then stirred at room temperature for 12 h after which it was diluted with DCM (150 mL). The organic phase was washed with 10% aqueous HCl (50 mL), dried over anhydrous sodium sulfate, and concentrated under vacuum. The residue obtained was purified by flash column chromatography eluting with hexanes/EtOAc (3:1 to 1:1) to give 5-ethenesulfonyl-2-methoxybenzene (3 g).

To a solution of 5-ethenesulfonyl-2-methoxybenzene (3 g), obtained as above, in dry dichloromethane (30 mL), chlorosulfonic acid (3 mL) was added dropwise at 0° C. The reaction mixture was warm to room temperature followed by the addition of $PCl_5$ (3 g) in three portions. The resulting reaction mixture was refluxed for 2 h. After cooling to room temperature, the reaction mixture was poured into ice water (100 mL) with stirring. The contents were extracted with EtOAc (2×150 mL). The combined organic phase was washed with saturated sodium chloride aqueous solution (2×100 mL), dried over anhydrous sodium sulfate, and concentrated under vacuum. The residue obtained was purified by column chromatography eluting with ethyl acetate/hexanes (1:4 to 1:1) to give 5-ethenesulfonyl-2-methoxybenzenesulfonyl chloride (3 g).

To a solution of benzo[b]thiophene-2-sulfonic acid (2-aminophenyl)-amide (10 mmol, prepared as in Example 1) in DCM (20 mL) and pyridine (20 mL), 5-ethenesulfonyl-2-methoxybenzenesulfonyl chloride (11 mmol) was added at RT and the reaction mixture was then allowed to stir at RT overnight. The reaction mixture was then diluted with DCM (100 mL). The organic phase was washed with 10% aqueous HCl (100 mL), water (100 mL) and brine (100 mL). The organic phase was dried over anhydrous sodium sulfate, and concentrated under vacuum. The residue obtained was purified by flash column chromatography eluting with DCM/EtOAc to obtain benzo[b]thiophene-2-sulfonic acid [2-(5-ethenesulfonyl-2-methoxybenzenesulfonylamino)phenyl] amide (2.8 g). LC: $T_r$ 1.15 min; MS: 565.9 $(M+1)^+$. $^1$H NMR ($CDCl_3$, 400 MHz): δ 4.17 (s, 3H), 6.03 (d, 1H), 6.42 (d, 1H), 6.56 (dd, 1H), 6.81 (dd, 1H), 6.97 (t, 1H), 7.13 (t, 1H), 7.18 (d, 1H), 7.32 (d, 1H), 7.42-7.52 (m, 2H), 7.62 (s, 1H), 7.80 (d, 1H), 7.83 (d, 1H), 8.04 (dd, 1H), 8.19 (d, 1H) ppm.

To a solution of benzo[b]thiophene-2-sulfonic acid [2-(5-ethenesulfonyl-2-methoxy-benzenesulfonylamino) -phenyl]-amide (0.5 mmol), as prepared above, in dry THF (10 mL), $Me_2NH$-THF solution (2.5 mL; 2 M $Me_2NH$ in THF solution) was added. The resulting reaction mixture was stirred at room temperature for 30 min. After removal of the solvent under vacuum, the residue obtained was purified by flash column chromatography eluting with EtOAc then DCM/methanol (100:2 to 100:10) to give 290 mg of benzo[b]thiophene-2-sulfonic acid {2-[5-(2-dimethylaminoethanesulfonyl)-2-methoxybenzenesulfonylamino]phenyl}-amide. LC: $T_r$ 0.99 min; MS: 610.7 $(M+1)^+$.

Example 20

To a solution of benzo[b]thiophene-2-sulfonic acid [2-(5-ethenesulfonyl-2-methoxybenzenesulfonylamino)phenyl]-amide (0.2 mmol, prepared as in Example 19) in dry DMF (3 mL), 2H-tetrazole (25 mg) was added. The resulting reaction mixture was stirred in a sealed tube for 2 hours at 110° C. The reaction mixture was diluted with DCM (20 mL) and washed with saturated sodium chloride solution (25 mL). The organic phase was dried over anhydrous sodium sulfate, and concentrated under vacuum. The residue obtained was purified by flash column chromatography eluting with EtOAc then DCM/methanol/AcOH (100:2:1 to 100:10:2) to furnish two separable regio-isomers. The less polar was benzo[b] thiophene-2-sulfonic acid {2-[2-methoxy-5-(2-tetrazol-2-yl-ethanesulfonyl)-benzenesulfonylamino]-phenyl}-amide (51 mg). LC: $T_r$ 1.08 min; MS: 635.6 (M+1)$^+$.

Example 21

To a solution of benzo[b]thiophene-2-sulfonic acid [2-(5-ethenesulfonyl-2-methoxybenzenesulfonylamino)phenyl]-amide (0.2 mmol, prepared as in Example 19) in dry THF (2 mL) was added 0.2 mL of pyrrolidine. The resulting reaction mixture was stirred at room temperature for 1 h. The reaction mixture was diluted with DCM (10 mL) and was washed with saturated sodium chloride aqueous solution (25 mL). The organic phase was dried over anhydrous sodium sulfate and concentrated under vacuum. The residue obtained was purified by flash column chromatography eluting with EtOAc then DCM/methanol/AcOH (100:2:1 to 100:10:2) to furnish 121 mg of benzo[b]thiophene-2-sulfonic acid {2-[2-methoxy-5-(2-pyrrolidin-1-yl-ethanesulfonyl)-benzenesulfonylamino]phenyl} amide. LC: $T_r$ 0.94 min; MS: 636.8 (M+1)$^+$. $^1$H NMR (CDCl$_3$, 400 MHz): δ 1.68 (m, 4H), 2.38 (m, 4H), 2.78(t, 2H), 3.28 (t, 2H), 4.20 (s, 3H), 6.76 (d, 1H), 6.96 (d, 1H), 7.14 (t, 1H), 7.21 (d, 1H), 7.36 (d, 1H), 7.41 (t, 1H), 7.49(t, 1H), 7.60 (s, 1H), 7.79 (d, 1H), 7.83 (d, 1H), 8.07 (d, 1H), 8.26 (d, 1H) ppm.

Example 22

To a solution of benzo[b]thiophene-2-sulfonic acid [2-(5-ethenesulfonyl-2-methoxybenzenesulfonylamino)phenyl] amide (0.2 mmol, prepared as in Example 19) in dry THF (2 mL) was added 0.2 mL of 1-methylpiperazine. The resulting reaction mixture was stirred at room temperature for 1 h. The reaction mixture was diluted with DCM (10 mL) and washed with saturated sodium chloride aqueous solution (25 mL). The organic phase was dried over anhydrous sodium sulfate and concentrated under vacuum. The residue obtained was purified by flash column chromatography eluting with EtOAc then DCM/methanol/AcOH (100:2:1 to 100:10:2) to furnish 118 mg of benzo[b]thiophene-2-sulfonic acid {2-[2-methoxy-5-(2-pyrrolidin-1-yl-ethanesulfonyl)-benzenesulfonylamino]-phenyl}-amide. LC: $T_r$ 0.84 min; MS: 666.0 (M+1)$^+$.

Example 23

To a solution of 4'-methoxy-2,2,2-trifluoroacetophenone (5 mmol) in 1,2-dichloroethane (10 mL), 0.5 mL of chlorosulfonic acid was added at 0° C. The resulting reaction mixture was gradually warmed to room temperature and then heated to reflux for 4 h. The reaction mixture was then cooled to room temperature and was diluted with chloroform (30 mL). The contents were then transferred to a separatory funnel, washed with water (50 mL), and the layers were separated. The aqueous layer was then extracted with chloroform (30 mL). The combined organic layers were washed with brine (50 mL) and dried over anhydrous sodium sulfate. The solvent was removed in vacuo and the residue obtained was purified by silica gel flash column chromatography using ethyl acetate/hexanes as eluant (1:10 to 1:2 gradient) to afford 440 mg of 5-(1,1-dichloro-2,2,2-trifluoroethyl)-2-methoxybenzenesulfonyl chloride. $^1$H NMR (CDCl$_3$, 400 MHz): δ 4.14 (s, 3H), 7.14 (d, 1H), 8.14 (dd, 1H), 8.44 (d, 1H) ppm.

To a solution of benzo[b]thiophene-2-sulfonic acid (2-aminophenyl)-amide (1 mmol, prepared as in Example 1) in DCM (2 mL) and pyridine (2 mL), 5-(1,1-dichloro-2,2,2-trifluoroethyl)-2-methoxybenzenesulfonyl chloride (1.1 mmol) was added at RT and the reaction mixture was then allowed to stir at RT overnight. The reaction mixture was then diluted with DCM (20 mL). The organic phase was washed with 10% aqueous HCl (20 mL), water (20 mL) and brine (20 mL). The organic phase was dried over anhydrous sodium sulfate and concentrated under vacuum. The residue obtained was purified by flash column chromatography eluting with DCM/EtOAc to afford 374 mg of benzo[b]thiophene-2-sulfonic acid [2-(5-(1,1-dichloro-2,2,2-trifluoroethyl)-2-methoxy-benzenesulfonylamino)phenyl]-amide. LC: $T_r$ 1.40 min; MS: 625.8 (M+1).

Example 24

To a solution of N-(2-amino-phenyl)-4-chlorobenzenesulfonamide (1.0 mmol, prepared as in Example 11) in DCM (2 mL) and pyridine (2 mL), 2-chloro-5-(trifluoromethyl) benzenesulfonyl chloride (1.1 mmol) was added at RT and the reaction mixture was then allowed to stir at RT overnight. The reaction mixture was then diluted with DCM (10 mL). The organic phase was washed with 10% aqueous HCl (10 mL), water (10 mL), and brine (10 mL). The organic phase was dried over anhydrous sodium sulfate and concentrated under vacuum. The residue obtained was purified by flash column chromatography eluting with DCM/EtOAc to obtain 419 mg of 2-chloro-N-[2-(4-chloro-benzenesulfonylamino)phenyl]-5-trifluoromethylbenzenesulfonamide. LC: $T_r$ 1.25 min; MS: 525.9 (M+1).

To a solution of 2-chloro-N-[2-(4-chloro-benzenesulfonylamino)phenyl]-5-trifluoromethylbenzenesulfonamide (0.5 mmol) in dioxane (5 mL), solid sodium methoxide (2 mmol) was added in one portion and the resulting reaction mixture was then heated to reflux for ca. 4 h. After the completion of the reaction, the reaction mixture was cooled to RT and concentrated in vacuo. The residue obtained was redissolved in EtOAc (10 mL) and washed with water (10 mL) and brine (10 mL). The organic phase was dried over anhydrous sodium sulfate and concentrated under vacuum. The residue obtained was purified by flash column chromatography eluting with DCM/EtOAc to obtain 160 mg of N-[2-(4-chlorobenzenesulfonylamino)phenyl]-2-methoxy-5-trifluoromethylbenzenesulfonamide. LC: $T_r$ 1.22 min; MS: 521.8 (M+1)$^+$.

Example 25

To a solution of benzo[b]thiophene-2-sulfonic acid (2-amino-phenyl)-amide (1 mmol, prepared as in Example 1) in DCM (2 mL) and pyridine (2 mL), 2-methoxy-4-nitrobenzenesulfonyl chloride (1.1 mmol) was added at RT and the reaction mixture was then allowed to stir at RT overnight or until the reaction was complete as determined by TLC or LC-MS. The reaction mixture was then diluted with DCM (20 mL). The organic phase was washed with 10% aqueous HCl (20 mL), water (20 mL), and brine (20 mL). The organic phase was dried over anhydrous sodium sulfate and concentrated under vacuum. The residue obtained was purified by flash column chromatography eluting with DCM/EtOAc to yield 353 mg of benzo[b]thiophene-2-sulfonic acid [2-(2-methoxy-4-nitrobenzenesulfonylamino)phenyl]-amide. LC: $T_r$ 1.21 min; MS: 520.7.7 (M+1)$^+$. $^1$H NMR (CDCl$_3$, 400 MHz): δ 4.24 (s, 3H), 6.72 (bs, 1H), 6.88 (d, 1H), 7.03 (t, 1H), 7.16 (t, 1H), 7.30 (d, 1H), 7.52 (t, 1H), 7.51 (t, 1H), 7.64 (s, 1H), 7.67-7.88 (m, 5H), 7.92 (s, 1H) ppm.

To a solution of the aforementioned benzo[b]thiophene-2-sulfonic acid [2-(2-methoxy-4-nitrobenzenesulfonylamino) phenyl]amide (0.5 mmol) in ethyl acetate (5 mL) and methanol (5 mL) was added palladium on activated carbon (10%, wet, ~20 mg). The reaction mixture was deaerated under vacuum for 5 min and stirred under hydrogen atmosphere (1 atm) for 20 min. The reaction mixture was filtered through a short pad of Celite and the pad was washed with methanol (20 mL) and dichloromethane (20 mL). The combined organic phase was concentrated under vacuum to afford 238 mg of the amino intermediate. LC: $T_r$ 1.13 min, MS: 490.9 $(M+1)^+$. $^1$H NMR (DMSO-$d_6$, 400 MHz): δ 3.82 (s, 3H), 6.03 (dd, 1H), 6.06 (bs, 2H), 6.21 (d, 1H), 6.90 (m, 2H), 7.05 (td, 1H), 7.20 (dd, 1H), 7.46 (td, 1H), 7.52 (td, 1H), 7.88 (s, 1H), 7.97(dd, 1H), 8.06 (dd, 1H), 8.66 (bs, 1H), 9.78 (bs, 1H) ppm.

To a solution of the amino intermediate (0.3 mmol) obtained as above in AcOH (2 mL) was added NH$_4$OAc (10 mmol), 37% aqueous formaldehyde solution (2 mL), and 40% aqueous glyoxal (1 mL). The reaction mixture was heated at 100° C. for 1.5 h. After cooling to room temperature, the reaction mixture was diluted with ethyl acetate (50 mL). The organic phase was washed with water (25 mL) and 1% aqueous KOH (25 mL). The organic phase was dried over sodium sulfate and concentrated under vacuum. The residue obtained was purified by flash column chromatography eluting with hexane/EtOAc (1:1) then with DCM/methanol (100:2 to 100:10) to afford 98 mg of benzo[b]thiophene-2-sulfonic acid [2-(4-imidazol-1-yl-2-methoxybenzenesulfonylamino)phenyl]-amide. LC: $T_r$ 0.87 min; MS: 541.6 $(M+1)^+$. $^1$H NMR (DMSO-$d_6$, 400 MHz): δ 4.06 (s, 3H), 6.80 (dd, 1H), 6.95 (td, 1H), 7.06 (m, 2H), 7.13 (s, 1H), 7.23(dd, 1H), 7.29 (d, 1H), 7.52-7.42(m, 3H), 7.67 (d, 1H), 7.88 (s, 1H), 7.90 (s, 1H), 7.94 (d, 1H), 8.02 (d, 1H), 8.46 (s, 1H), 9.06 (bs, 1H) ppm.

Example 26

To a solution of benzene-1,2-diamine (1 mmol) in DCM (4 mL) and pyridine (1 mL) at 0° C., benzo[b]thiophene-2-sulfonyl chloride (2.2 mmol) was added at 0° C. in small portions (over 10-15 min) at 0° C. The reaction mixture was then gradually warmed to RT with stirring continued for 6 h. The reaction mixture was then diluted with DCM (10 mL). The organic phase was washed with 10% aqueous HCl (10 mL), water (10 mL), and brine (10 mL). The organic phase was dried over anhydrous sodium sulfate and concentrated under vacuum. The residue obtained was purified by flash column chromatography eluting with DCM followed by EtOAc/DCM (1% to 3%) to give 425 mg of N-[2-(benzothiophene-2-sulfonyl)amino]phenyl-benzothiophene-2-sulfonamide. LC: $T_r$ 1.18 min; MS: 501.7 $(M+1)^+$. $^1$H NMR (DMSO-$d_6$, 400 MHz): δ 7.14 ($A_2B_2$, 4H), 7.48 (dd, 2H), 7.54 (dd, 2H), 7.95 (s, 2H), 7.97 (d, 2H), 8.03 (d, 2H) ppm.

Example 27

To a solution of benzene-1,2-diamine (0.5 mmol) in DCM (2 mL) and pyridine (0.5 mL) at 0° C., benzofuran-2-sulfonyl chloride (1.1 mmol; prepared as in Example 12) was added at 0° C. in small portions over 10-15 min. The reaction mixture was then gradually warmed to RT with stirring continued for 6 h. The reaction mixture was then diluted with DCM (5 mL). The organic phase was washed with 10% aqueous HCl (5 mL), water (5 mL), and brine (5 mL). The organic phase was dried over anhydrous sodium sulfate and concentrated under vacuum. The residue obtained was purified by flash column chromatography eluting with DCM followed by EtOAc/ DCM (1% to 3%) to give 117 mg of N-{2-[(1-benzofuran-2-ylsulfonyl)amino]phenyl}-1-benzofuran-2-sulfonamide. $T_r$ 1.18 min; MS: 469.7 $(M+1)^+$.

Example 28

To a solution of o-phenylenediamine (4 mmol) in DCM (20 mL) and pyridine (4 mL) at 0° C., 3,4-dichlorobenzenesulfonyl chloride (4.4 mmol) was added in small portions. The reaction mixture was then gradually warmed to RT with stirring continued until the reaction was complete as determined by TLC or LC-MS. The reaction mixture was then diluted with DCM (20 mL). The organic phase was washed with water (2×20 mL) and 20 mL of brine. The organic phase was dried over anhydrous sodium sulfate and concentrated under vacuum. The residue obtained was purified by flash column chromatography eluting with DCM/EtOAc to give 760 mg of N-(2-amino-phenyl)-3,4-dichloro-benzenesulfonamide. LC: $T_r$ 0.98 min, MS: 317.0 $(M+1)^+$; $^1$H NMR (CDCl$_3$, 400 MHz): δ 4.95 (bs, 2H), 6.45 (t, 1H), 6.11 (d, 1H), 6.72 (d, 1H), 6.92 (t, 1H), 7.59 (dd, 1H), 7.80 (d, 3H) ppm.

The monosulfonamide (1 mmol) obtained as above was dissolved in DCM (2 mL) and pyridine (2 mL). 5-fluoro-2-methoxy-benzenesulfonyl chloride (1.1 mmol) was added at RT and the reaction mixture was then allowed to stir at RT overnight. The reaction mixture was then diluted with DCM (10 mL). The organic phase was washed with 10% aqueous HCl (10 mL), water (10 mL), and brine (10 mL). The organic phase was dried over anhydrous sodium sulfate and concentrated under vacuum. The residue obtained was purified by flash column chromatography eluting with DCM/EtOAc to give 302 mg of N-[2-(3,4-dichlorobenzenesulfonylamino)-phenyl]-5-fluoro-2-methoxybenzenesulfonamide. LC: $T_r$ 1.19 min; MS: 505.5 $(M+1)^+$; $^1$H NMR (DMSO-d6, 400 MHz): δ 3.92 (s, 3H), 6.85 (dd, 1H), 7.02 (m, 1H), 7.08 (m, 2H), 7.28 (dd, 1H), 7.40 (dd, 1H), 7.50 (m, 1H), 7.56 (dd, 1H), 7.80 (d, 1H), 7.82 (s, 1H), 9.11 (bs, 1H), 9.56 (bs, 1H) ppm.

Example 29

To a mixture of pyridine-4-boronic acid (3 mmol), 4-bromo-2-nitrophenylamine (2 mmol), and Pd(PPh$_3$)$_4$ (20 mg) in DME (10 mL), 2 M aqueous Na$_2$CO$_3$ was added. The suspension was then refluxed under nitrogen for 36 h. After cooling to the room temperature, the reaction mixture was diluted with ethyl acetate (150 mL). The organic phase was washed with brine (50 mL), dried over sodium sulfate, and concentrated under vacuum. The residue obtained was purified by column chromatography eluting with hexanes/ethyl acetate (1:1) then ethyl acetate/methanol (10:1) to give 516 mg of 2-nitro-4-pyridin-4-ylphenylamine. $^1$H NMR (DMSO-$d_6$, 400 MHz): LC: $T_r$ 0.44 min, MS: 216.1 $(M+1)^+$. $^1$H NMR (DMSO-$d_6$, 400 MHz): δ 7.13 (d, 1H), 7.60 (d, 2H), 7.69 (bs, 2H), 7.88 (dd, 1H), 8.37 (d, 1H), 8.55 (d, 2H) ppm.

To a solution of 2-nitro-4-pyridin-4-ylphenylamine (1 mmol) in pyridine (3 mL), 4-chloro-benzenesulfonyl chloride (1.2 mmol) was added and the resulting mixture was stirred at room temperature for 24 h. The reaction mixture was diluted with ethyl acetate (20 mL). The contents were washed with brine (25 mL), dried over sodium sulfate and concentrated under vacuum. The residue obtained was purified by column chromatography eluting with hexanes/ethyl acetate (1:1) then ethyl acetate to give 156 mg of 4-chloro-N-(2-nitro-4-pyridin-4-ylphenyl)benzene sulfonamide.

To a solution of 4-chloro-N-(2-nitro-4-pyridin-4-ylphenyl) benzene sulfonamide (0.2 mmol) in ethyl acetate (10 mL), palladium on activated carbon (10%, wet, 10 mg) was added.

The reaction mixture was deaerated under vacuum for 5 min and stirred under hydrogen atmosphere (1 atm) for 30 min. The reaction mixture was filtered through a short pad of Celite, washing the pad with methanol (10 mL) and ethyl acetate (15 mL). The combined organic phase was concentrated under vacuum to give 58 mg of N-(2-amino-4-pyridin-4-ylphenyl)-4-chlorobenzene sulfonamide.

To a solution of N-(2-amino-4-pyridin-4-ylphenyl)-4-chlorobenzene sulfonamide (0.1 mmol) in pyridine (0.5 mL), 5-bromo-2-methoxy-benzenesulfonyl chloride (0.12 mmol) was added. The reaction mixture was stirred at room temperature for 2 h and then was diluted with ethyl acetate (10 mL). The contents were washed with brine (10 mL), dried over sodium sulfate, and concentrated under vacuum. The residue obtained was purified by column chromatography eluting with hexanes/ethyl acetate (1:1) followed by ethyl acetate to give 49 mg of 5-bromo-N-[2-(4-chlorobenzenesulfonylamino) -5-pyridin-4-ylphenyl]-2-methoxybenzenesulfonamide. LC: $T_r$ 0.94 min, MS: 610.8 (M+1)$^+$.

Example 30

To a solution of 4-fluoro-2-nitroaniline (1 mmol) in pyridine (3 mL), 5-bromo-2-methoxybenzenesulfonyl chloride (1.2 mmol) was added and the resulting mixture was stirred at room temperature for 24 h. The reaction mixture was diluted with ethyl acetate (20 mL). The contents were washed with 10% aqueous HCl (20 mL) and brine (20 mL), dried over sodium sulfate, and concentrated under vacuum. The residue obtained was purified by column chromatography eluting with hexanes/ethyl acetate to give 223 mg of 5-bromo-N-(4-fluoro-2-nitrophenyl)-2-methoxybenzenesulfonamide.

The nitro intermediate (0.5 mmol) above was dissolved in EtOH (10 mL) and was treated with tin(II) chloride (2.5 mmol). The reaction mixture was heated to reflux for 12 h. The contents were cooled to RT and treated with 1 M aqueous NaOH until the pH of the reaction mixture was between 8-9 which resulted in formation of a precipitate. The precipitate was then filtered, washed with methanol (10 mL) and DCM (10 mL). The combined filtrate was concentrated in vacuo and the residue obtained was purified by column chromatography eluting with DCM/ethyl acetate as eluant to give 115 mg of 5-bromo-N-(4-fluoro-2-aminophenyl)-2-methoxybenzenesulfonamide.

To a solution of 5-bromo-N-(4-fluoro-2-aminophenyl)-2-methoxybenzenesulfonamide (0.1 mmol) in pyridine (0.5 mL) and DCM (2 mL), 4-chlorobenzenesulfonyl chloride (0.12 mmol) was added. The reaction mixture was stirred at room temperature for 4 h and then diluted with ethyl acetate (10 mL). The contents were washed with 10% aqueous HCl (10 mL) and brine (10 mL), dried over sodium sulfate, and concentrated under vacuum. The residue obtained was purified by column chromatography eluting with hexanes/ethyl acetate (1:1) followed by ethyl acetate to give 43 mg of 5-bromo-N-[2-(4-chlorobenzenesulfonylamino) -4-fluorophenyl]-2-methoxybenzenesulfonamide. LC: $T_r$ 1.10 min, MS: 551.8 (M+1)+

Example 31

To a solution of 4-fluorobenzene-1,2-diamine (1 mmol) in DCM (2 mL) and pyridine (2 mL) at 0° C., benzothiophene-2-sulfonyl chloride (2.2 mmol) was added in small portions. The reaction mixture was then stirred at rt until the reaction was complete as determined by TLC or LC-MS. The reaction mixture was then diluted with DCM (15 mL). The organic phase was washed with 10% aqueous HCl (5 mL), water (5 mL), and 5 mL of brine. The organic phase was dried over anhydrous sodium sulfate and concentrated under vacuum. The residue obtained was purified by flash column chromatography eluting with DCM/EtOAc to obtain 192 mg of N,N'-(4-fluoro-1,2-phenylene)bis(1-benzothiophene-2-sulfonamide) as a solid.

$^1$H NMR (DMSO-d$_6$; 300 MHz) δ 6.8-6.9 (m, 1H), 7.0-7.2 (m, 2H), 7.4-7.6 (m, 4H), 7.83 (s, 1H), 7.9-8.0 (m, 4H), 8.04 (s, 1H), 9.7-10.1 (br s, 2H) ppm.

Example 32

To a solution of 4-cyanobenzene-1,2-diamine (1 mmol) in pyridine (4 mL), benzothiophene-2-sulfonyl chloride (2.2 mmol) was added in small portions. The reaction mixture was then heated at 80° C. with stirring until the reaction was complete as determined by TLC or LC-MS. The reaction mixture was then diluted with ethyl acetate (20 mL). The organic phase was washed with 10% aqueous HCl solution (15 mL), water (15 mL) and brine (5 mL). The organic phase was dried over anhydrous sodium sulfate and concentrated under vacuum. The residue obtained was purified by flash column chromatography eluting with DCM/EtOAc to obtain 184 mg of N,N'-(4-cyano-1,2-phenylene)bis(1-benzothiophene-2-sulfonamide) as a solid.

$^1$H NMR (CDCl$_3$; 300 MHz) δ 7.31 (s, 1H); 7.4-7.6 (m, 6H), 7.65 (s, 1H), 7.7-7.9 (m, 5H) ppm.

Example 33

N,N'-(4-chloro-1,2-phenylene)bis(1-benzothiophene-2-sulfonamide) (310 mg) was prepared as in Example 31 using 4-chlorobenzene-1,2-diamine and benzothiophene-2-sulfonyl chloride as requisite starting materials.

$^1$H NMR (DMSO-d$_6$; 300 MHz) δ 7.18 (s, 2H), 7.22 (s, 1H), 7.4-7.6 (m, 4H), 7.9-8.1 (m, 6H), 9.8-10.1 (br s, 2H) ppm.

Example 34

N,N'-(4-bromo-1,2-phenylene)bis(1-benzothiophene-2-sulfonamide) (255 mg) was prepared as in Example 31 using 4-bromobenzene-1,2-diamine and benzothiophene-2-sulfonyl chloride as requisite starting materials.

$^1$H NMR (DMSO-d$_6$; 300 MHz) δ 7.06 (d, 1H), 7.2-7.4 (m, 2H), 7.4-7.7 (m, 4H), 7.9-8.1 (m, 6H), 9.8-10.2 (br s, 2H) ppm.

Example 35

N,N'-(4-methoxy-1,2-phenylene)bis(1-benzothiophene-2-sulfonamide) (472 mg) was prepared as in Example 31 using 4-methoxybenzene-1,2-diamine and benzothiophene-2-sulfonyl chloride as requisite starting materials.

$^1$H NMR (DMSO-d$_6$; 300 MHz) δ 3.58 (s, 3H), 6.62 (dd, 1H), 6.81 (d, 1H), 6.88 (d, 1H), 7.4-7.6 (m, 4H), 7.83 (s, 1H), 7.9-8.2 (m, 5H), 9.65 (br s, 2H) ppm.

Example 36

To a solution of 3-[2-(benzo[b]thiophene-2-sulfonylamino) -phenyl sulfamoyl]-4-methoxybenzoic acid (1 mmol, see Example 4) in anhydrous DMF (4 mL), DIEA (1.5 mmol) and HBTU (1.2 mmol) were added at rt and the mixture was stirred for 30 min. tert-Butylamine (1.2 mmol) was then added at rt with stirring continued for another 60 min.

The reaction mixture was diluted with water (20 mL) and the precipitate formed was filtered and washed with water. A white solid (488 mg) was obtained which was used for further transformation without purification.

$^1$H NMR (DMSO-d$_6$; 300 MHz) δ 1.36 (s, 9H), 4.05 (s, 3H), 6.90 (d, 1H), 6.98 (t, 1H), 7.12 (t, 1H), 7.23 (d, 1H), 7.30 (d, 1H), 7.4-7.6 (m, 2H), 7.85-8.05 (m, 3H), 8.05-8.15 (m, 3H), 9.10 (s, 1H), 9.82 (s, 1H) ppm.

The amide product from above (0.5 mmol) was suspended in dry benzene (10 mL) and was treated with phosphrous oxychloride (1 mL). The reaction mixture was refluxed for 3 h after which the reaction was complete. The solvent and excess POCl$_3$ was removed in vacuo and residue obtained was recrystallized from isopropanol to afford 125 mg of benzo[b]thiophene-2-sulfonic acid [2-(5-cyano-2-methoxybenzene-sulfonylamino)-phenyl]-amide as a light yellow solid.

$^1$H NMR (DMSO-d$_6$; 300 MHz) δ 4.05 (s, 3H), 6.90 (d, 1H), 7.02 (t, 1H), 7.14 (t, 1H), 7.25 (d, 1H), 7.4-7.6 (m, 3H), 7.91 (s, 1H), 7.95-8.05 (m, 2H), 8.06-8.14 (m, 2H), 9.18 (br s, 1H), 9.82 (br s, 1H) ppm.

Example 37

To a solution of 3-[2-(Benzo[b]thiophene-2-sulfonylamino)-phenyl sulfamoyl]-4-methoxybenzoic acid (1 mmol, see Example 4) in anhydrous DMF (4 mL), DIEA (4.5 mmol) and HBTU (1.2 mmol) were added at RT and the mixture was stirred for 30 min. N-Hydroxyacetamidine (2.0 mmol) was then added at RT with stirring continued for another 60 min. The reaction mixture was diluted with ethyl acetate (30 mL), washed with water (2×20 mL), and dried over anhydrous Na$_2$SO$_4$. After removal of the solvent in vacuo, 385 mg of the oxamate ester was obtained as a white solid, which was used for further transformation without any purification.

The oxamate obtained as above (0.35 mmol) was suspended in xylene (6 mL) and was treated with powdered 4 Å molecular sieves (1 g). The reaction mixture was heated to reflux for 6 h after which the reaction was complete. The contents were then filtered and the solvent was removed in vacuo to give 29 mg of benzo[b]thiophene-2-sulfonic acid {2-[2-methoxy-5-(3-methyl-[1,2,4]oxadiazol-5-yl)benzene-sulfonylamino]phenyl}-amide as an off-white solid.

$^1$H NMR (DMSO-d$_6$; 300 MHz) δ 2.38 (s, 3H), 4.05 (s, 3H), 6.90 (d, 1H), 6.98 (t, 1H), 7.12 (t, 1H), 7.23 (d, 1H), 7.30 (d, 1H), 7.4-7.6 (m, 2H), 7.85-8.05 (m, 3H), 8.05-8.15 (m, 3H), 9.10 (s, 1H), 9.82 (s, 1H) ppm.

Example 38

To a solution of 2-thipheneethylamine (1.5 g, 11.8 mmol) and 37% aqueous formaldehyde (3.9 ml, 47.2 mmol) in ethanol (10 mL), concentrated hydrochloric acid (3.9 mL) was added and the resulting solution was heated at 50° C. for 6 h. All volatiles were removed under reduced pressure. The residue was taken up in dioxane (13 mL) and 2 N aq. NaOH solution (12.8 mL) and cooled to 0° C. The reaction mixture was treated with di-t-butyldicarbonate (2.24 g, 10.28 mmol) and stirred for 10 at room temperature. The reaction mixture was diluted with ethyl acetate (25 mL) and the aqueous layer was extracted with ethyl acetate (10 mL). The combined organic phase was washed with water, brine, and dried over Na$_2$SO$_4$. Solvent was removed under reduced pressure and the product was purified by silica gel column chromatography eluting with 3% EtOAc/hexanes to obtain 1.7 g of 6,7-dihydro-4H-thieno[3,2-c]pyridine-5-carboxylic acid tert-butyl ester.

2-Chlorosulfonyl-6,7-dihydro-4H-thieno[3,2-c]pyridine-5-carboxylic acid tert-butyl ester (0.25 g) was prepared from 6,7-dihydro-4H-thieno[3,2-c]pyridine-5-carboxylic acid tert-butyl ester (1.6 g, 6.69 mmol) by using n-BuLi and N-chlorosuccinimide as described in the Example 12.

2-[2-(Benzo[b]thiophene-2-sulfonylamino)-phenylsulfamoyl]-6,7-dihydro-4H-thieno[3,2-c]pyridine-5-carboxylic acid tert-butyl ester (280 mg) was prepared by using 2-chlorosulfonyl-6,7-dihydro-4H-thieno[3,2-c]pyridine-5-carboxylic acid tert-butyl ester (0.049 g, 0.148 mmol) and benzo[b]thiophene-2-sulfonic acid (2-amino-phenyl)-amide (0.045 g, 0.148 mmol, prepared as in Example 1) using pyridine in DCM following procedure as in Example 2.

$^1$HNMR (400 MHz, CDCl$_3$) δ 1.48 (s, 9H), 2.76-2.85 (m, 2H), 3.65-3.75 (m, 2H), 4.39 (s, 2H), 7.06-7.24 (m, 5H), 7.36-7.52 (m, 4H), 7.71 (s, 1H), 7.78-7.86 (m, 2H) ppm.

Example 39

N,N'-(4,5-Dichloro-1,2-phenylene)bis(1-benzothiophene-2-sulfonamide) (120 mg) was prepared by using 4,5-dichloro-benzene-1,2-diamine (0.06 g, 0.33 mmol) and Benzo[b]thiophene-2-sulfonyl chloride (0.157 g, 0.67 mmol), following procedure as in Example 32.

$^1$HNMR (400 MHz, DMSO-d$_6$) δ 7.34 (s, 2H), 7.41-7.57 (m, 4H), 7.93-8.20 (m, 6H), 9.60-10.50 (br s, 2H) ppm.

Example 40

N,N'-(4-Trifluoromethyl-1,2-phenylene)bis(1-benzothiophene-2-sulfonamide) (100 mg) was prepared by using 4-trifluoromethyl-benzene-1,2-diamine (0.06 g, 0.33 mmol) and benzo[b]thiophene-2-sulfonyl chloride (0.157 g, 0.67 mmol), following procedure as in Example 32.

$^1$HNMR (400 MHz, DMSO-d$_6$) δ 7.48 (s, 1H), 7.42-7.55 (m, 6H), 7.89-8.08 (m, 6H), 9.90-10.40 (m, 2H) ppm.

Example 41

N,N'-(4-chloro-5-fluoro-1,2-phenylene)bis(1-benzothiophene-2-sulfonamide) (0.108 g) was prepared by using 4-chloro-5-fluoro-benzene-1,2-diamine (0.054 g, 0.33 mmol) and Benzo[b]thiophene-2-sulfonyl chloride (0.157 g, 0.67 mmol), following the procedure as in Example 32.

$^1$HNMR (400 MHz, DMSO-d$_6$) δ 7.15-7.26 (dd, 2H), 7.42-7.56 (m, 4H), 7.90-8.09 (m, 6H), 9.60-10.30 (br s, 2H) ppm.

Example 42

N,N'-(4,5-fluoro-1,2-phenylene)bis(1-benzothiophene-2-sulfonamide) (0.095 g) was prepared employing 4,5-difluoro-benzene-1,2-diamine (0.048 g, 0.33 mmol) and benzo[b]thiophene-2-sulfonyl chloride (0.157 g, 0.67 mmol), following procedure as in Example 32.

$^1$HNMR (400 MHz, DMSO-d$_6$) δ 7.16 (t, 2H), 7.44-7.56 (m, 4H), 7.93-8.30 (m, 6H), 9.80-10.02 (br s, 2H) ppm.

Biological Assays

GalR1 Binding Assay

The affinity of compounds for GalR1 were studied in an [$^{125}$I]galanin displacement binding assay. Bowes melanoma cell membranes were used in the GalR1 binding assay. Compound was diluted in 40% DMSO/water. The final assay concentration ranging from 0.1 nM to 10 uM in 4% final DMSO concentration was used. The final binding assay conditions were 25 mM Tris-HCL, pH 7.4 buffer containing 10 mM MgCl$_2$, 1-10 ug membrane, 300 pM [$^{125}$I]galanin (SA=2200 Ci/mmoL, (Perkin Elmer part no. NEX333), and compound in final DMSO concentration of 4% (final assay volume of 100 uL). Positive control wells (C+) lacked compound, and negative control wells (C−) lacked compound and contained cold excess galanin (1 micromolar). The reaction was carried out at room temp for 60-90 min. Membrane containing bound [$^{125}$I]galanin ligand was isolated following filtration onto Unifilter-96 GF/C filter plates (PerkinElmer part no. 6005177) using a cell harvester instrument. Plates were washed 5 times with cold 25 mM Tris-HCL, pH 7.5 containing 0.05% bovine serum albumin (BSA). Following filtration, 50 uL of Microscint PS (Packard part no. 6013631) was added, plates were sealed with TopSeal-A adhesive seals (Packard part no. 6005185). $^{125}$I isotope bound to the Unifilter-96 GF/C plates was counted using a TopCount instrument (Packard).

Data Analysis

Raw Data Conversion

Percent inhibition of [$^{125}$I]galanin binding was calculated according to the equation [100×1−{(Sample$_{cpm}$−C−$_{cpm}$)/ C+$_{cpm}$−C−$_{cpm}$)}]. Percent inhibition of [$^{125}$I]galanin binding (Y) vs compound concentration (X) data were generated.

Curve Fitting

The IC$_{50}$ values were calculated by fitting the data using parameters for a sigmoidal dose response, variable slope non-linear regression (GraphPAD Prizm, San Diego, Calif.) according to the equation: Y=Bottom+(Top−Bottom)/(1+10^((LogEC50−X)*HillSlope)); X is the logarithm of concentration. Y is the response; Y starts at Bottom and goes to Top with a sigmoid shape. This is identical the the "four parameter logistic equation."

The compounds of Formula (I) in Table 1 showed an IC$_{50}$ of less than or about 10 micromolar in the binding assay described above.

Functional Cell-Based Assay

The agonist functional activity of compounds in Bowes cells was determined by measuring forskolin-stimulated intracellular cAMP. cAMP was quantitated using a cAMP detection kit. Bowes cells were grown minimum essential medium eagle containing Earle's salts, L-glutamine and sodiumk bicarbonate, supplemented with 10% fetal bovine serum. Cells were harvested by incubating cell monolayers in 15 mL PBS (Ca$^{2+}$, Mg$^{2+}$-free) for 20 min in humidified 37° C. incubator containing 95% O$_2$, 5% CO$_2$. Gentle tapping of flasks dislodged cells, and cell suspensions were centrifuged 600×g for 5 min (4° C.). Cells were counted using a hemocytometer and diluted in stimulation mix (containing anti-cAMP antibody and isobutyl methyl xanthine) to a final cell density of 1- to 5×10$^6$ cell/mL. Typically, assays used between 10,000 and 50,000 of cells per well. Compound was diluted in 1% DMSO/PBS to final assay concentration ranging from 0.1 nM to 10 uM, and 5 uL was dispensed in Costar black 384-well plates. Forskolin was filuted in 1% DMSO/ PBS. Galanin was diluted in PBS containing complete protease inhibitor cocktail (Complete Mini, EDTA-free, Roche Diagnostics). Cells (10 uL) were pre-incubated with compound for 15 min, and then forskolin (5 to 20 uM) and galanin (0.1 to 10 nM) were added to a final assay volume of 20 uL. Following 30 min incubation of cells in a humidified 37° C. incubator with 95% O$_2$, 5% CO$_2$, Alexa Fluor 594-cAMP detection mix was added (20 uL), and plates were incubated at room temp with shaking for 1 hr. The degree of fluorescence polarization (expressed as mP units) was measured using an Envision (Perkin Elmer) fluorescence plate reader. Standard curves of cAMP (1-100 nM) were used to quantitate the amount of cAMP.

The compounds of Formula (I) in Table 1 showed an EC$_{50}$ of less than or about 10 micromolar in the functional cell based assay described above and were determined to be GalR1 agonists.

Behavioral Assessment

Animals

Male Sprague Dawley rats (100-150 g for nerve ligation) were purchased from Charles River (Portage, Mich.). Prior to surgery, animals were group-housed and maintained in a temperature regulated environment (lights on between 7:00 a.m. and 8:00 p.m.). Two weeks after surgery, experimentation began when animals were between 250-350 g. Rats had access to food and water ad libitum.

For the assessment of neuropathic pain, mechanical allodynia in the affected paw of animals who had undergone sciatic nerve ligation was evaluated using von Frey filaments. As described previously (Chaplan et al, Quantitative assessment of tactile allodynia in the rat paw. J Neurosci Meth, 1994; 53:55-62), two weeks following surgery, rats were acclimated to the testing box which was constructed of plexiglass with a wire mesh floor to allow access to the planter surface of the hind paws. Using the Dixons Up-Down method, a baseline level of allodynia was taken with allodynia defined as a withdrawal threshold of less than 4 g. Test compounds were then administered and subsequent withdrawal thresholds determined.

When dosed in the range between about 15 to 100 mg/kg with compounds of Examples 1-30 in Table 1, the withdrawal thresholds of the animals with sciatic nerve injury increased as compared to the withdrawal threshold of vehicle treated animals with sciatic nerve injury.

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the mammal being treated. Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

REFERENCES

1. Bedecs, Katarina; Berthold, Malin; Bartfai, Tamas. Galanin—10 years with a neuroendocrine peptide. International Journal of Biochemistry & Cell Biology (1995), 27(4), 337-49.
2. Kask, Kalev; Berthold, Malin; Bartfai, Tamas. Galanin receptors: involvement in feeding, pain, depression and Alzheimer's disease. Life Sciences (1997), 60(18), 1523-1533.
3. Kask, Kalev; Langel, Ulo; Bartfai, Tamas. Galanin-a neuropeptide with inhibitory actions. Cellular and Molecular Neurobiology (1995), 15(6), 653-73.
4. Branchek, T. A.; Smith, K. E.; Gerald, C.; Walker, M. W. Galanin receptor subtypes. Trends in Pharmacological Sciences (2000), 21(3), 109-117.

5. Waters, S. M.; Krause, J. E. Distribution of galanin-1, -2 and -3 receptor messenger RNAs in central and peripheral rat tissues. Neuroscience (Oxford) (1999), Volume Date 2000, 95(1), 265-271.
6. Heuillet, Edith; Bouaiche, Zakia; Menager, Jean; Dugay, Philippe; Munoz, Noelli; Dubois, Herve; Amiranoff, Brigitte; Crespo, Andre; Lavayre, Jacques; et al. The human galanin receptor: ligand-binding and functional characteristics in the Bowes melanoma cell line. European Journal of Pharmacology, Molecular Pharmacology Section (1994), 269(2), 139-47.
7. Branchek, T. A.; Smith, K. E.; Gerald, C.; Walker, M. W. Galanin receptor subtypes. Trends in Pharmacological Sciences (2000), 21(3), 109-117.
8. Liu, Hong-Xiang; Hokfelt, Tomas. The participation of galanin in pain processing at the spinal level. Trends in Pharmacological Sciences (2002), 23(10), 468-474.
9. Ma, W.; Bisby, M. A. Differential expression of galanin immunoreactivities in the primary sensory neurons following partial and complete sciatic nerve injuries. Neuroscience (Oxford) (1997), 79(4), 1183-1195.
10. Wood, Jackie D.; Liu, Sumei. Galanin receptors and actions. Drugs of the Future (2004), 29(2), 149-161.
11. Hua, Xiao-Ying; Hayes, Carol S.; Hofer, Anthony; Fitzsimmons, Bethany; Kilk, Kalle; Langel, Uelo; Bartfai, Tamas; Yaksh, Tony L. Galanin acts at GalR1 receptors in spinal antinociception: Synergy with morphine and AP-5. Journal of Pharmacology and Experimental Therapeutics (2004), 308(2), 574-582.
12. Zachariou, Venetia; Brunzell, Darlene H.; Hawes, Jessica; Stedman, Diann R.; Bartfai, Tamas; Steiner, Robert A.; Wynick, David; Langel, Uelo; Picciotto, Marina R. The neuropeptide galanin modulates behavioral and neurochemical signs of opiate withdrawal. Proceedings of the National Academy of Sciences of the United States of America (2003), 100(15), 9028-9033.
13. Liu, Hong-Xiang; Brumovsky, Pablo; Schmidt, Ralf; Brown, William; Payza, Kemal; Hodzic, Lejla; Pou, Chantevy; Godbout, Claude; Hokfelt, Tomas. Receptor subtype-specific pronociceptive and analgesic actions of galanin in the spinal cord: selective actions via GalR1 and GalR2 receptors. Proceedings of the National Academy of Sciences of the United States of America (2001), 98(17), 9960-9964.
14. Bennett, G. J., Xie, Y.-K. A peripheral mononeuropathy in rat that produces disorders of pain sensation like those seen in man. Pain (1988), 33(988), 87-107.
15. Henson, B. S., et al. Galanin Receptor 1 Has Anti-Proliferative Effects In Oral Squamous Cell Carcinoma. J. Biol. Chem. (2005).
16. Millan, M. J. (1999) The Induction of Pain: An Integrative Review, Progress in Neurobiology, 57, 1-164 (Pergamon Press).
17. McQuay et al. (1995) Anticonvulsant Drugs For The Management of Pain: A Systematic Review, British Medical Journal, 311, 1047-52.

We claim:

1. A compound of Formula (I):

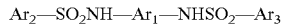

$$Ar_2—SO_2NH—Ar_1—NHSO_2—Ar_3 \quad (I)$$

wherein
Ar$_1$ is a phenylene group optionally substituted 1 to 4 times, wherein the substituents of Ar$_1$ are selected from the group consisting of
a) -hydrogen;
b) -halo;
c) -cyano;
d) -nitro;
e) -perhaloalkyl;
I) -alkyl;
g) -aryl;
h) -heteroaryl;
i) -cycloalkyl;
j) -L-aryl;
k) -L-arylene-aryl;
l) -L-arylene-alkyl;
m) -Q-alkyl;
n) -Q-aryl;
o) -Q-alkylene-aryl;
p) -Q-arylene-alkyl;
q) -L-Q-alkylene-aryl;
r) -arylene-Q-alkyl;
s) -L-Q-alkyl;
t) -L-Q-aryl;
u) -L-Q-heteroaryl;
v) -L-Q-cycloalkyl;
w) -L-Q-arylene-alkyl;
x) -D$_4$-alkylene-NR$_1$R$_2$;
y) -D$_4$-NR$_1$R$_2$;
z) -D$_4$-alkyl; and
aa) -D$_4$-H;
wherein
D$_4$ comprises a direct bond, —CH$_2$—, —O—, —N(R$_4$)—, —C(O)—, —CON(R$_4$)—, —N(R$_4$)C(O)—, —N(R$_4$)CON(R$_4'$)—, —N(R$_4$)C(O)O—, —OC(O)N(R$_4$)—, —N(R$_4$)SO$_2$—, —SO$_2$N(R$_4$)—, —C(O)—O—, —O—C(O)—, —S—, —S(O)—, —S(O)$_2$—, —N(R$_4$)SO$_2$N(R$_4'$)—, or —N=N—;
wherein
R$_4$ and R$_{4'}$ are independently selected from the group consisting of -hydrogen, -alkyl, -aryl, -arylene-alkyl, and -alkylene-aryl;
R$_1$ and R$_2$ are independently selected from the group consisting of hydrogen, alkyl, and aryl, wherein R$_1$ and R$_2$ may be taken together to form a ring having the formula —(CH$_2$)$_o$-Z$_4$-(CH$_2$)$_p$— bonded to the nitrogen atom to which R$_1$ and R$_2$ are attached,
wherein
o and p are, independently, 1, 2, 3, or 4 and o+p is less than or equal to 6,
Z$_4$ is a direct bond, —CH$_2$—, —C(O)—, —O—, —N(H)—, —S—, —S(O)—, —S(O)$_2$—, —CON(H)—, —NHC(O)—, —NHC(O)N(H)—, —NH(SO$_2$)—, —S(O)$_2$N(H)—, —(O)CO—, —NHS(O)$_2$NH—, —OC(O)—, —N(R$_{31}$)—, —N(C(O)R$_{31}$)—, —N(C(O)NHR$_{31}$)—, —N(C(O)NR$_{31}$R$_{32}$)—, —N(S(O)$_2$NHR$_{31}$)—, —N(SO$_2$R$_{31}$)—, or —N(C(O)OR$_{31}$)—;
wherein
R$_{31}$ and R$_{32}$ are independently selected from the group consisting of -hydrogen, -alkyl, -aryl, and -alkylene-aryl;
L is a direct bond, -alkylene, -alkenylene, or -alkynylene; and
Q is a direct bond, —CH$_2$—, —O—, or —S—;
Ar$_2$ is a benzothiophene group;
Ar$_3$ is selected from the group consisting of an aryl, heteroaryl, fused cycloalkylaryl, fused cycloalkylheteroaryl, fused heterocyclylaryl, and fused heterocyclylheteroaryl group,
wherein at least one of Ar$_2$ and Ar$_3$ has an oxygen atom or sulfur atom vicinal or geminal to the point of attachment to the —NHSO$_2$— group, and wherein Ar$_2$ and Ar$_3$ may be optionally substituted 1 to 5 times with a substituent selected from the group consisting of
a) -hydrogen;
b) -halo;
c) -cyano;
d) -nitro;
e) -alkyl;
f) -aryl;
g) -cycloalkyl;
h) -heterocyclyl;
i) -alkylene-cycloalkyl;
j) -perhaloalkyl;
k) heteroaryl;
l) -alkylene-aryl;
m) -D$_1$-H;
n) -D$_1$-R$_3$;
o) -D$_1$-alkyl;
p) -D$_1$-aryl;
q) -D$_1$-perhaloalkyl;
r) -D$_1$-alkylene-R$_3$;
s) -D$_1$-alkylene-aryl;
t) -D$_1$-alkylene-D$_2$-R$_3$;
u) -D$_1$-cycloalkyl;
v) -D$_1$-heterocyclyl;
w) -D$_1$-aryl;
x) -D$_1$-heteroaryl;
y) -D$_1$-arylene-D$_2$-R$_3$;
z) -D$_1$-heteroarylene-D$_2$-R$_3$;
aa) -D$_1$-alkylene-heteroaryl;
bb) -D$_1$-alkylene-heterocyclyl;
cc) -D$_1$-alkylene-aryl;
aa) -D$_1$-alkylene-arylene-D$_2$-R$_3$;
bb) -D$_1$-alkylene-heteroarylene-D$_2$-R$_3$;
ff) -D$_1$-alkylene-NR$_5$R$_6$;
gg) -D$_1$-arylene-NR$_5$R$_6$; and
hh) -acid isostere;
wherein
D$_1$ is a direct bond, —CH$_2$—, —O—, —N(R$_7$)—, —C(O)—, —CON(R$_7$)—, —N(R$_7$)C(O)—, —N(R$_7$)CON(R$_8$)—, —N(R$_7$)C(O)O—, —OC(O)N(R$_7$)—, —N(R$_7$)SO$_2$—, —SO$_2$N(R$_7$)—, —C(O)—O—, —O—C(O)—, —S—, —S(O)—, —S(O)$_2$—, —N(R$_7$)SO$_2$N(R$_8$)—, or —N=N—;
wherein
R$_7$ and R$_8$ are independently selected from the group consisting of -hydrogen, -alkyl, -aryl, -arylene-alkyl, -alkylene-aryl, and -alkylene-arylene-alkyl;
R$_3$ is -hydrogen, -alkyl, -aryl, -heterocyclyl, or -heteroaryl; and
R$_5$ and R$_6$ are independently selected from the group consisting of hydrogen, alkyl, and aryl, wherein R$_5$ and R$_6$ may be taken together to form a ring having the formula —(CH$_2$)$_o$-Z$_1$-(CH$_2$)$_p$— bonded to the nitrogen atom to which R$_5$ and R$_6$ are attached,
wherein
o and p are, independently, 1, 2, 3, or 4 and o+p is less than or equal to 6,
Z$_1$ is a direct bond, —CH$_2$—, —C(O)—, —O—, —N(H)—, —S—, —S(O)—, —S(O)$_2$—, —CON(H)—, —NHC(O)—, —NHC(O)N(H)—, —NH(SO$_2$)—, —S(O)$_2$N(H)—, —(O)CO—, —NHS(O)$_2$NH—, —OC(O)—, —N(R$_9$)—, —N(C(O)R$_9$)—, —N(C(O)NHR$_9$)—, —N(C(O)NR$_9$R$_{10}$)—, —N(S(O)$_2$NHR$_9$)—, —N(SO$_2$R$_9$)—, or —N(C(O)OR$_9$)—;
wherein
R$_9$ and R$_{10}$ are independently selected from the group consisting of -hydrogen, -alkyl, -aryl, and -alkylene-aryl;
D$_2$ is -alkylene-, -alkenylene-, -alkylene-S—, —S-alkylene-, -alkylene-O—, —O-alkylene-, -alkylene-S(O)$_2$—, —S(O)$_2$-alkylene, —O—, —N(R$_{11}$)—, —C(O)—, —CON(R$_{11}$)—, —N(R$_{11}$)C(O)—, —N(R$_{11}$)CON(R$_{12}$)—, —N(R$_{11}$)C(O)O—, —OC(O)N(R$_{11}$)—, —N(R$_{11}$)SO$_2$—, —SO$_2$N(R$_{11}$)—, —C(O)—O—, —O—C(O)—, —S—, —S(O)—, —S(O)$_2$—, or —N(R$_{11}$)SO$_2$N(R$_{12}$)—,
wherein
R$_{11}$ and R$_{12}$ are independently selected from the group consisting of -hydrogen, -alkyl, and -aryl;
and wherein
the alkyl, cycloalkyl, heterocyclyl, aryl, heteroaryl, alkylene, cycloalkylene, heterocyclylene, arylene, and heteroaryl in Ar$_2$, Ar$_3$, R$_1$ through R$_{32}$ may be optionally substituted independently 1 to 4 times with a substituent group selected from the group consisting of
a) -hydrogen;
b) -halo;
c) -cyano;
d) -nitro;
e) -perhaloalkyl;
f) -A-perhaloalkyl;
g) -A-R$_{40}$;
h) -A-alkyl;
i) -A-aryl;
j) -A-alkylene-aryl;
k) -A-alkylene-NR$_{41}$R$_{42}$; and
l) -A-alkyl-E-R$_{43}$;
wherein
A and E are independently selected from the group consisting of —CH$_2$—, —O—, —N(R$_{44}$)—, —C(O)—, —CON(R$_{44}$)—, —N(R$_{44}$)C(O)—, —N(R$_{44}$)CON(R$_{45}$)—, —N(R$_{44}$)C(O)O—, —OC(O)N(R$_{44}$)—, —N(R$_{44}$)SO$_2$—, —SO$_2$N(R$_{44}$)—, —C(O)—O—, —O—C(O)—, and —N(R$_{44}$)SO$_2$N(R$_{45}$)—,
wherein R$_{44}$ and R$_{45}$ are independently selected from the group consisting of -hydrogen, -alkyl, -aryl, -arylene-alkyl, -alkylene-aryl, and -alkylene-arylene-alkyl;
R$_{40}$ and R$_{43}$ are independently selected from the group consisting of -hydrogen, -alkyl, -aryl, -arylene-alkyl, -alkylene-aryl, and -alkylene-arylene-alkyl; and
R$_{41}$ and R$_{42}$ are independently selected from the group consisting of hydrogen, aryl, and alkyl, wherein R$_{41}$ and R$_{42}$ may be taken together to form a ring having the formula —(CH$_2$)$_o$-Z$_4$-(CH$_2$)$_p$— bonded to the nitrogen atom to which R$_{41}$ and R$_{42}$ are attached,
wherein
o and p are, independently, 1, 2, 3, or 4 and o+p is less than or equal to 6,
Z$_4$ is a direct bond a direct bond, —CH$_2$—, —C(O)—, —O—, —N(H)—, —S—, —S(O)—, —S(O)$_2$—, —CON(H)—, —NHC(O)—, —NHC(O)N(H)—, —NH(SO$_2$)—, —S(O)$_2$N(H)—, —(O)CO—, —NHS(O)$_2$NH—, —OC(O)—, —N(R$_{46}$)—, —N(C(O)R$_{46}$)—, —N(C(O)NHR$_{46}$)—, —N(C(O)NR$_{46}$R$_{47}$)—, —N(S(O)$_2$NHR$_{46}$)—, —N(SO$_2$R$_{46}$)—, or —N(C(O)OR$_{46}$)—;

wherein
R$_{46}$ and R$_{47}$ are independently selected from the group consisting of hydrogen, aryl, alkyl, and -alkylene-aryl;
or a pharmaceutically acceptable salt or biohydrolyzable amide or biohydrolyzable ester thereof,
and
wherein the compound of Formula (I) is a GalR1 agonist.

2. The compound of Formula (I) in claim 1, or a pharmaceutically acceptable salt thereof, wherein the —NHSO$_2$—Ar$_2$ and the —NHSO$_2$—Ar$_3$ substituent groups of Ar$_1$ are located on adjacent atoms in the Ar$_1$ ring.

3. The compound of Formula (I) in claim 1, or a pharmaceutically acceptable salt thereof, having the formula

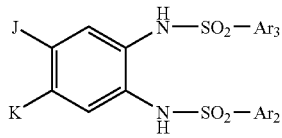

wherein J and K are independently selected from the group consisting of
a) -hydrogen;
b) -halo;
c) -cyano;
d) -nitro;
e) -perhaloalkyl;
f) -alkyl;
g) -aryl;
h) -heteroaryl;
i) -cycloalkyl;
j) -L-aryl;
k) -L-arylene-aryl;
l) -L-arylene-alkyl;
m) -Q-alkyl;
n) -Q-aryl;
o) -Q-alkylene-aryl;
p) -Q-arylene-alkyl;
q) -L-Q-alkylene-aryl;
r) -arylene-Q-alkyl;
s) -L-Q-alkyl;
t) -L-Q-aryl;
u) -L-Q-heteroaryl;
v) -L-Q-cycloalkyl;
w) -L-Q-arylene-alkyl;
x) -D$_4$-alkylene-NR$_1$R$_2$;
y) -D$_4$-NR$_1$R$_2$;
z) -D$_4$-alkyl; and
aa) -D$_4$-H;
wherein
D$_4$ is a direct bond, —CH$_2$—, —O—, —N(R$_4$)—, —C(O)—, —CON(R$_4$)—, —N(R$_4$)C(O)—, —N(R$_4$)CON(R$_{4'}$)—, —N(R$_4$)C(O)O—, —OC(O)N(R$_4$)—, —N(R$_4$)SO$_2$—, —SO$_2$N(R$_4$)—, —C(O)O—, —O—C(O)—, —S—, —S(O)—, —S(O)$_2$—, —N(R$_4$)SO$_2$N(R$_{4'}$)—, or —N═N—;
wherein R$_4$ and R$_{4'}$ are independently selected from the group consisting of -hydrogen, -alkyl, -aryl, -arylene-alkyl, and -alkylene-aryl;
R$_1$ and R$_2$ are independently selected from the group consisting of hydrogen, alkyl, and aryl, wherein R$_1$ and R$_2$ may be taken together to form a ring having the formula —(CH$_2$)$_o$-Z$_4$-(CH$_2$)$_p$— bonded to the nitrogen atom to which R$_1$ and R$_2$ are attached, wherein
o and p are, independently, 1, 2, 3, or 4 and o+p is less than or equal to 6,
Z$_4$ is a direct bond, —CH$_2$—, —C(O)—, —O—, —N(H)—, —S—, —S(O)—, —S(O)$_2$—, —CON(H)—, —NHC(O)—, —NHC(O)N(H)—, —NH(SO$_2$)—, —S(O)$_2$N(H)—, —(O)CO—, —NHS(O)$_2$NH—, —OC(O)—, —N(R$_{31}$)—, —N(C(O)R$_{31}$)—, —N(C(O)NHR$_{31}$)—, —N(C(O)NR$_{31}$R$_{32}$)—, —N(S(O)$_2$NHR$_{31}$)—, —N(SO$_2$R$_{31}$)—, or —N(C(O)OR$_{31}$)—;
wherein
R$_{31}$ and R$_{32}$ are independently selected from the group consisting of -hydrogen, -alkyl, -aryl, and -alkylene-aryl;
L is a direct bond, -alkylene, -alkenylene, or -alkynylene; and
Q is a direct bond, —CH$_2$—, —O—, or —S—.

4. The compound of Formula (I) in claim 3, or a pharmaceutically acceptable salt thereof, wherein J and K are independently selected from the group consisting of hydrogen, halo, haloalkyl, alkoxy, haloalkoxy, cyano, carboxy, amide, -D$_4$-alkyl, -D$_4$-alkylene-NR$_1$R$_2$, -D$_4$-NR$_1$R$_2$, -D$_4$-alkyl; -D$_4$-H, wherein D$_4$ is a —C(O)—, —CON(R$_4$)—, —SO$_2$N(R$_4$)—, or —C(O)—O—, wherein R$_4$ is -hydrogen, -alkyl, -aryl, -arylene-alkyl, or -alkylene-aryl;
wherein
R$_1$ and R$_2$ are independently selected from the group consisting of hydrogen, alkyl, and aryl, wherein R$_1$ and R$_2$ may be taken together to form a ring having the formula —(CH$_2$)$_o$-Z$_4$-(CH$_2$)$_p$— bonded to the nitrogen atom to which R$_1$ and R$_2$ are attached,
wherein
o and p are, independently, 1, 2, 3, or 4 and o+p is less than or equal to 6,
Z$_4$ is a direct bond, —CH$_2$—, —C(O)—, —O—, —N(H)—, —S—, —S(O)—, —S(O)$_2$—, —CON(H)—, —NHC(O)—, —NHC(O)N(H)—, —NH(SO$_2$)—, —S(O)$_2$N(H)—, —(O)CO—, —NHS(O)$_2$NH—, —OC(O)—, —N(R$_{31}$)—, —N(C(O)R$_{31}$)—, —N(C(O)NHR$_{31}$)—, —N(C(O)NR$_{31}$R$_{32}$)—, —N(S(O)$_2$NHR$_{31}$)—, —N(SO$_2$R$_{31}$)—, or —N(C(O)OR$_{31}$)—;
wherein
R$_{31}$ and R$_{32}$ are independently selected from the group consisting of -hydrogen, -alkyl, -aryl, and -alkylene-aryl,
wherein at least one of J and K is a group other than hydrogen.

5. The compound of Formula (I) in claim 3, or a pharmaceutically acceptable salt thereof, wherein Ar$_2$ and Ar$_3$ are unsubstituted benzothiophene group.

6. The compound of Formula (I) in claim 1, or a pharmaceutically acceptable salt thereof, wherein Ar$_1$ is an unsubstituted phenylene group.

7. The compound of Formula (I) in claim 1, or a pharmaceutically acceptable salt thereof, wherein Ar$_1$ is an unsubstituted phenylene group and the —NHSO$_2$—Ar$_2$ and the —NHSO$_2$—Ar$_3$ substituent groups are located on adjacent carbon atoms in the Ar$_1$ ring.

8. The compound of Formula (I) in claim 1, or a pharmaceutically acceptable salt thereof, wherein Ar$_2$ and Ar$_3$ are different.

9. The compound of Formula (I) in claim 1, or a pharmaceutically acceptable salt thereof, wherein $Ar_3$ is selected from the group consisting of an aryl, heteroaryl, and fused heterocyclylheteroaryl group.

10. The compound of Formula (I) in claim 1, or a pharmaceutically acceptable salt thereof, wherein $Ar_3$ is selected from the group consisting of an optionally substituted or unsubstituted phenyl, benzothiophenyl, benzofuranyl, or a 4,5,6,7-tetrahydrothieno[3,2-c]pyridinyl group.

11. The compound of Formula (I) in claim 1, or a pharmaceutically acceptable salt thereof, wherein $Ar_3$ is selected from the group consisting of an aryl, heteroaryl, fused cycloalkylaryl, fused cycloalkylheteroaryl, fused heterocyclylaryl, and fused heterocyclylheteroaryl group optionally substituted 1 to 5 times, wherein at least one of $Ar_2$ and $Ar_3$ is either

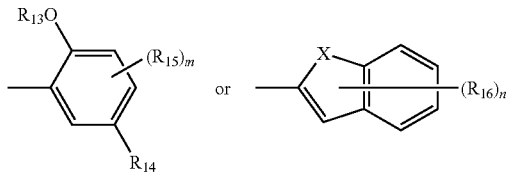

wherein
$R_{13}$ is alkyl, alkylene-cycloalkyl, haloalkyl, perhaloalkyl, or cycloalkyl;
$R_{14}$ is
a) -halo;
b) -cyano;
c) -nitro;
d) -perhaloalkyl;
e) $-D_1-R_{17}$;
f) $-D_1$-alkyl;
g) $-D_1$-alkylene-$R_{17}$;
h) $-D_1$-alkylene-$D_2-R_{17}$;
i) $-D_1$-aryl;
j) -D-heteroaryl;
k) $-D_1$-arylene-$D_2-R_{17}$;
l) $-D_1$-heteroarylene-$D_2-R_{17}$;
m) $-D_1$-alkylene-heteroaryl;
n) $-D_1$-alkylene-heterocyclyl;
o) $-D_1$-alkylene-aryl;
p) $-D_1$-alkylene-arylene-$D_2-R_{17}$;
q) $-D_1$-alkylene-heteroarylene-$D_2-R_{17}$;
r) $-D_1$-alkylene-$NR_{18}R_{19}$;
s) $-D_1$-arylene-$NR_{18}R_{19}$; or
t) -acid isostere;
wherein
$D_1$ is a direct bond, $-S(O)_2-$, $-CON(R_{20})-$, $-SO_2N(R_{20})-$, $-C(O)-O-$, $-S-$, or $-S(O)-$;
wherein $R_{20}$ is -hydrogen, -alkyl, -aryl, -heterocyclyl, or -heteroaryl;
$R_{17}$ is -hydrogen, -alkyl, -aryl, -heterocyclyl, or -heteroaryl;
$R_{18}$ and $R_{19}$ are independently selected from the group consisting of hydrogen, aryl, and alkyl, wherein $R_{18}$ and $R_{19}$ may be taken together to form a ring having the formula $-(CH_2)_o-Z_2-(CH_2)_p-$ bonded to the nitrogen atom to which $R_{18}$ and $R_{19}$ are attached,
wherein
o and p are, independently, 1, 2, 3, or 4 and o+p is less than or equal to 6, $Z_2$ is a direct bond, $-CH_2-$, $-C(O)-$, $-O-$, $-N(H)-$, $-S-$, $-S(O)-$, $-S(O)_2-$, $-CON(H)-$, $-NHC(O)-$, $-NHC(O)N(H)-$, $-NH(SO_2)-$, $-S(O)_2N(H)-$, $-(O)CO-$, $-NHS(O)_2NH-$, $-OC(O)-$, $-N(R_{20})-$, $-N(C(O)R_{20})-$, $-N(C(O)NHR_{20})-$, $-N(C(O)NR_{20}R_{21})-$, $-N(S(O)_2NHR_{20})-$, $-N(SO_2R_{20})-$, or $-N(C(O)OR_{20})-$;
wherein
$R_{20}$ and $R_{21}$ are independently selected from the group consisting of -hydrogen, -alkyl, -aryl, and -alkylene-aryl;
$D_2$ is -alkylene-, -alkenylene-, -alkylene-S—, —S-alkylene-, -alkylene-O—, —O-alkylene-, -alkylene-$S(O)_2-$, $-S(O)_2$-alkylene, $-O-$, $-N(R_{22})-$, $-C(O)-$, $-CON(R_{22})-$, $-N(R_{22})C(O)-$, $-N(R_{22})CON(R_{23})-$, $-N(R_{22})C(O)O-$, $-OC(O)N(R_{22})-$, $-N(R_{22})SO_2-$, $-SO_2N(R_{22})-$, $-C(O)-O-$, $-O-C(O)-$, $-S-$, $-S(O)-$, $-S(O)_2-$, or $-N(R_{22})SO_2N(R_{23})-$,
wherein
$R_{22}$ and $R_{23}$ are independently selected from the group consisting of -hydrogen, -alkyl, and -aryl;
$R_{15}$ and $R_{16}$ are independently selected from the group consisting of
a) -hydrogen;
b) -halogen;
c) -cyano;
d) -alkyl;
e) -aryl;
f) -alkylene-aryl;
g) $-D_3$-H;
h) $-D_3$-alkyl;
i) $-D_3$-aryl;
j) $-D_3$-alkylenearyl;
k) -Y-alkyl;
l) -Y-aryl;
m) -Y-alkylene-aryl;
n) -Y-alkylene-$NR_{24}R_{25}$; and
o) -Y-alkylene-W—$R_{26}$;
wherein
$D_3$ is $-O-$, $-C(O)-O-$, $-C(O)-NH-$, $-SO_2-$, $-SO_2-NH-$, or $-C(O)-$;
Y and W are independently selected from the group consisting of, $-CH_2-$, $-O-$, $-N(H)$, $-S-$, $SO_2-$, $-CON(H)-$, $-NHC(O)-$, $-NHCON(H)-$, $-NHSO_2-$, $-SO_2N(H)-$, $-C(O)-O-$, $-NHSO_2NH-$, and $-O-CO-$,
$R_{26}$ is aryl, alkyl, alkylene-aryl, alkoxy, or alkoxyaryl;
$R_{24}$ and $R_{25}$ are independently selected from the group consisting of hydrogen, aryl, or alkyl, wherein $R_{24}$ and $R_{25}$ may be taken together to form a ring having the formula $-(CH_2)_o-Z_3-(CH_2)_p-$ bonded to the nitrogen atom to which $R_{24}$ and $R_{25}$ are attached,
wherein
o and p are, independently, 1, 2, 3, or 4 and o+p is less than or equal to 6,
$Z_3$ is a direct bond, $-CH_2-$, $-C(O)-$, $-O-$, $-N(H)-$, $-S-$, $-S(O)-$, $-S(O)_2-$, $-CON(H)-$, $-NHC(O)-$, $-NHC(O)N(H)-$, $-NH(SO_2)-$, $-S(O)_2N(H)-$, $-(O)CO-$, $-NHS(O)_2NH-$, $-OC(O)-$, $-N(R_{29})-$, $-N(C(O)R_{29})-$, $-N(C(O)NHR_{29})-$, $-N(C(O)NR_{29}R_{30})-$, $-N(S(O)_2NHR_{29})-$, $-N(SO_2R_{29})-$, or $-N(C(O)OR_{29})-$;

wherein
R$_{29}$ and R$_{30}$ are independently selected from the group consisting of hydrogen, aryl, alkyl, and -alkylaryl;
R$_{26}$ is hydrogen, alkyl, aryl, or alkylene-aryl,
X is sulfur; and
m and n are independently 0, 1, or 2.

12. The compound of Formula (I) in claim 1, or a pharmaceutically acceptable salt thereof wherein Ar$_3$ is

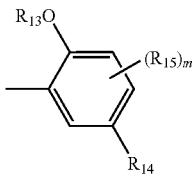

wherein
R$_{14}$ is
a) -D$_1$-perhalo C$_2$-C$_6$ alkyl;
b) -D$_1$-alkylene-heteroaryl;
c) -D$_1$-alkylene-heterocyclyl;
d) -D$_1$-alkylene-NR$_{18}$R$_{19}$; or
e) -acid isostere.

13. The compound of Formula (I) in claim 11, or a pharmaceutically acceptable salt thereof, wherein Ar$_3$ is the group

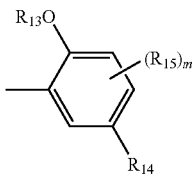

and Ar$_2$ is

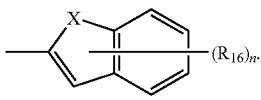

14. The compound of Formula (I) in claim 11, or a pharmaceutically acceptable salt thereof, wherein Ar$_3$ is a phenyl group substituted with at least one halo group.

15. The compound of Formula (I) in claim 11, or a pharmaceutically acceptable salt thereof, wherein Ar$_2$ is the group

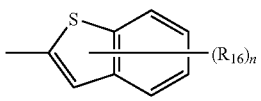

and
Ar$_3$ is a phenyl, a benzothiopheneyl, or benzofuranyl group optionally substituted 1 to 5 times,
wherein
Ar$_2$ and Ar$_3$ are the same or different.

16. The compound of Formula (I) in claim 11, or a pharmaceutically acceptable salt thereof, wherein Ar$_2$ is an unsubstituted benzothiophene group.

17. A compound selected from the group consisting of:
Benzo[b]thiophene-2-sulfonic acid [2-(2-chloro-5-trifluoromethylbenzenesulfonylamino)phenyl] amide;
Benzo[b]thiophene-2-sulfonic acid {2-[2-methoxy-5-(propane-2-sulfonyl)benzenesulfonylamino]phenyl} amide;
3-[2-(Benzo[b]thiophene-2-sulfonylamino) -phenylsulfamoyl]-4-methoxy-benzoic acid methyl ester;
3-[2-(Benzo[b]thiophene-2-sulfonylamino) -phenylsulfamoyl]-4-methoxy-benzoic acid;
5-Chloro-3-methyl-benzo[b]thiophene-2-sulfonic acid [2-(2-methoxy-5-trifluoromethane sulfonyl-benzenesulfonylamino) -phenyl]-amide;
Benzo[b]thiophene-2-sulfonic acid [2-(5-bromo-2-methoxy-benzene sulfonylamino)-phenyl]-amide;
Benzo[b]thiophene-2-sulfonic acid [2-(4-chloro-benzenesulfonylamino)phenyl] amide;
Benzo[b]thiophene-2-sulfonic acid [2-(4-methoxy-2-nitro-benzenesulfonylamino)phenyl]amide;
Benzo[b]thiophene-2-sulfonic acid [2-(4-methanesulfonyl-2-methoxy-benzenesulfonylamino) -phenyl] amide;
Benzo[b]thiophene-2-sulfonic acid [2-(2-methoxy-5-methylbenzenesulfonylamino)phenyl] amide;
Benzo[b]thiophene-2-sulfonic acid [2-(2-methoxy-5-trifluoromethylbenzenesulfonylamino)phenyl] amide;
Benzo[b]thiophene-2-sulfonic acid {2-[5-(2-dimethylaminoethanesulfonyl)-2-methoxy-benzenesulfonylamino]phenyl} amide;
Benzo[b]thiophene-2-sulfonic acid {2-[2-methoxy-5-(2-tetrazol-2-yl-ethanesulfonyl)-benzenesulfonylamino]-phenyl}-amide;
Benzo[b]thiophene-2-sulfonic acid {2-[2-methoxy-5-(2-pyrrolidin-1-yl-ethanesulfonyl)-benzenesulfonylamino]-phenyl}-amide;
Benzo[b]thiophene-2-sulfonic acid {2-[2-methoxy-5-(2-pyrrolidin-1-yl-ethanesulfonyl)-benzenesulfonylamino]-phenyl}-amide;
Benzo[b]thiophene-2-sulfonic acid [2-(5-(1,1-Dichloro-2,2,2-trifluoroethyl)-2-methoxy-benzenesulfonylamino) phenyl] amide;
Benzo[b]thiophene-2-sulfonic acid [2-(4-imidazol-1-yl-2-methoxybenzenesulfonylamino)phenyl] amide;
N-[2-(Benzothiophene-2-sulfonyl)amino]phenylbenzothiophene-2-sulfonamide;
N-[2-(Benzothiophene-2-sulfonyl)amino]phenylbenzothiophene-2-sulfonamide;
N,N'-(4-fluoro-1,2-phenylene)bis(1-benzothiophene-2-sulfonamide);
N,N'-(4-cyano-1,2-phenylene)bis(1-benzothiophene-2-sulfonamide);
2-[2-(Benzo[b]thiophene-2-sulfonylamino)-phenylsulfamoyl]-6,7-dihydro-4H-thieno[3,2-c]pyridine-5-carboxylic acid tert-butyl ester;
N,N'-(4,5-dichloro-1,2-phenylene)bis(1-benzothiophene-2-sulfonamide);
N,N'-(4-trifluoromethyl-1,2-phenylene)bis(1-benzothiophene-2-sulfonamide);
N,N'-(4-chloro-5-fluoro-1,2-phenylene)bis(1-benzothiophene-2-sulfonamide);
N,N'-(4,5-fluoro-1,2-phenylene)bis(1-benzothiophene-2-sulfonamide);
Benzo[b]thiophene-2-sulfonic acid [2-(5-cyano-2-methoxy-benzenesulfonylamino)-phenyl]-amide;
Benzo[b]thiophene-2-sulfonic acid {2-[2-methoxy-5-(3-methyl-[1,2,4]oxadiazol-5-yl)-benzenesulfonylamino]-phenyl}-amide;

N,N'-(4-chloro-1,2-phenylene)bis(1-benzothiophene-2-sulfonamide);

N,N'-(4-bromo-1,2-phenylene)bis(1-benzothiophene-2-sulfonamide); and

N,N'-(4-methoxy-1,2-phenylene)bis(1-benzothiophene-2-sulfonamide), or a pharmaceutically acceptable salts thereof.

18. A pharmaceutical composition comprising the compound of Formula (I) as in claim 1, or a pharmaceutically acceptable salt thereof 19. The pharmaceutical composition of claim 18, further comprising a pharmaceutically suitable carrier, excipient, diluent, or mixture thereof.

20. The pharmaceutical composition of claim 18, wherein the compound of Formula (I), or a pharmaceutically acceptable salt thereof, is present in an amount sufficient to increase activity of a GalR1 receptor.

21. The pharmaceutical composition of claim 18, wherein the compound of Formula (I), or a pharmaceutically acceptable salt thereof, is present in an amount sufficient to stimulate GalR1 in a subject.

22. The pharmaceutical composition of claim 18, comprising a therapeutically effective amount of a compound of Formula (I), or a pharmaceutically acceptable salt thereof, wherein said therapeutically effective amount is an amount of the compound of Formula (I) capable of at least partially activating the GalR1 receptor in a subject.

23. The pharmaceutical composition of claim 18 in the form of an oral dosage unit.

24. The pharmaceutical composition of claim 18 in the form of a parenteral dosage unit.

25. The pharmaceutical composition of claim 18, further comprising one or more additional therapeutic agents.

26. The pharmaceutical composition of claim 25, further comprising one or more therapeutic agents selected from the group consisting of biologic response modifiers, analgesics, NSAIDs, DMARDs, glucocorticoids, sulfonylureas, biguanides, acarbose, PPAR agonists, DPP-IV inhibitors, GK activators, insulin, insulin mimetics, insulin secretagogues, insulin sensitizers, GLP-1, GLP-1 mimetics, cholinesterase inhibitors, antipsychotics, antidepressants, anticonvulsants, HMG CoA reductase inhibitors, cholestyramine, and fibrates.

27. The pharmaceutical composition of claim 25, further comprising one or more therapeutic agents selected from the group consisting of anticancer agents.

28. A pharmaceutical composition comprising the compound of Formula (I) as in claim 2, or a pharmaceutically acceptable salt thereof.

29. A pharmaceutical composition comprising the compound of Formula (I) as in claim 3, or a pharmaceutically acceptable salt thereof.

30. A pharmaceutical composition comprising the compound of Formula (I) as in claim 4, or a pharmaceutically acceptable salt thereof.

31. A pharmaceutical composition comprising the compound of Formula (I) as in claim 5, or a pharmaceutically acceptable salt thereof.

32. A pharmaceutical composition comprising the compound of Formula (I) as in claim 6, or a pharmaceutically acceptable salt thereof.

33. A pharmaceutical composition comprising the compound of Formula (I) as in claim 7, or a pharmaceutically acceptable salt thereof.

34. A pharmaceutical composition comprising the compound of Formula (I) as in claim 8, or a pharmaceutically acceptable salt thereof.

35. A pharmaceutical composition comprising the compound of Formula (I) as in claim 9, or a pharmaceutically acceptable salt thereof.

36. A pharmaceutical composition comprising the compound of Formula (I) as in claim 10, or a pharmaceutically acceptable salt thereof.

37. A pharmaceutical composition comprising the compound of Formula (I) as in claim 11, or a pharmaceutically acceptable salt thereof.

38. A pharmaceutical composition comprising the compound of Formula (I) as in claim 12, or a pharmaceutically acceptable salt thereof.

39. A pharmaceutical composition comprising the compound of Formula (I) as in claim 13, or a pharmaceutically acceptable salt thereof.

40. A pharmaceutical composition comprising the compound of Formula (I) as in claim 14, or a pharmaceutically acceptable salt thereof.

41. A pharmaceutical composition comprising the compound of Formula (I) as in claim 15, or a pharmaceutically acceptable salt thereof.

42. A pharmaceutical composition comprising the compound of Formula (I) as in claim 16, or a pharmaceutically acceptable salt thereof.

43. A pharmaceutical composition comprising the compound of Formula (I) as in claim 17, or a pharmaceutically acceptable salt thereof.

44. A compound of Formula (Ia)

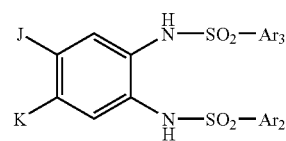

(Ia)

wherein wherein J and K are independently selected from the group consisting of a) -hydrogen;
b) -halo;
c) -cyano;
d) -nitro;
e) -perhaloalkyl;
f) -alkyl;
g) -aryl;
h) -heteroaryl;
i) -cycloalkyl;
j) -L-aryl;
k) -L-arylene-aryl;
l) -L-arylene-alkyl;
m) -Q-alkyl;
n) -Q-aryl;
o) -Q-alkylene-aryl;
p) -Q-arylene-alkyl;
q) -L-Q-alkylene-aryl;
r) -arylene-Q-alkyl;
s) -L-Q-alkyl;
t) -L-Q-aryl;
u) -L-Q-heteroaryl;
v) -L-Q-cycloalkyl;
w) -L-Q-arylene-alkyl;
x) -$D_4$-alkylene-$NR_1R_2$;
y) -$D_4$-$NR_1R_2$;

z) -$D_4$-alkyl; and
aa) -$D_4$-H;
wherein
$D_4$ is a direct bond, —$CH_2$—, —O—, —N($R_4$)—, —C(O)—, —CON($R_4$)—, —N($R_4$)C(O)—, —N($R_4$)CON($R_{4'}$)—, —N($R_4$)C(O)O—, —OC(O)N($R_4$)—, —N($R_4$)$SO_2$—, —$SO_2$N($R_4$)—, —C(O)O—, —O—C(O)—, —S—, —S(O)—, —S(O)$_2$—, —N($R_4$)$SO_2$N($R_{4'}$)—, or —N=N—;
wherein $R_4$ and $R_{4'}$ are independently selected from the group consisting of -hydrogen, -alkyl, -aryl, -arylene-alkyl, and -alkylene-aryl;
$R_1$ and $R_2$ are independently selected from the group consisting of hydrogen, alkyl, and aryl, wherein $R_1$ and $R_2$ may be taken together to form a ring having the formula —$(CH_2)_o$-$Z_4$-$(CH_2)_p$— bonded to the nitrogen atom to which $R_1$ and $R_2$ are attached,
wherein
o and p are, independently, 1, 2, 3, or 4 and o +p is less than or equal to 6,
$Z_4$ is a direct bond, —$CH_2$—, —C(O)—, —O—, —N(H)—, —S—, —S(O)—, —S(O)$_2$—, —CON(H)—, —NHC(O)—, —NHC(O)N(H)—, —NH($SO_2$)—, —S(O)$_2$N(H)—, —(O)CO—, —NHS(O)$_2$NH—, —OC(O)—, —N($R_{31}$)—, —N(C(O)$R_{31}$)—, —N(C(O)NH$R_{31}$)—, —N(C(O)N$R_{31}R_{32}$)—, —N(S(O)$_2$NH$R_{31}$)—, —N($SO_2R_{31}$)—, or —N(C(O)O$R_{31}$)—;
wherein
$R_{31}$ and $R_{32}$ are independently selected from the group consisting of -hydrogen, -alkyl, -aryl, and -alkylene-aryl;
L is a direct bond, -alkylene, -alkenylene , or -alkynylene;
Q is a direct bond, —$CH_2$—, —O—, or —S—;
$Ar_2$ is

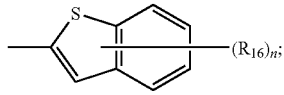

and
$Ar_3$ is either

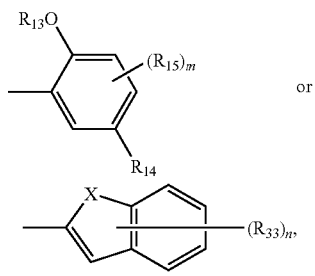

wherein
$R_{13}$ is alkyl, alkylene-cycloalkyl, haloalkyl, perhaloalkyl, or cycloalkyl;
$R_{14}$ is
a) -halo;
b) -cyano;
c) -nitro;
d) -perhaloalkyl;
e) $D_1$-$R_{17}$;
f) -$D_1$-alkyl;
g) -$D_1$-alkylene-$R_{17}$;
h) -$D_1$-alkylene-$D_2$-$R_{17}$;
i) -$D_1$-aryl;
j) -$D_1$-heteroaryl;
k) -$D_1$-arylene-$D_2$-$R_{17}$;
l) -$D_1$-heteroarylene-$D_2$-$R_{17}$;
m) -$D_1$-alkylene-heteroaryl;
n) -$D_1$-alkylene-heterocyclyl;
o) -$D_1$-alkylene-aryl;
p) -$D_1$-alkylene-arylene-$D_2$-$R_{17}$;
q) -$D_1$-alkylene-heteroarylene-$D_2$-$R_{17}$;
r) -$D_1$-alkylene-$NR_{18}R_{19}$;
s) -$D_1$-arylene-$NR_{18}R_{19}$;
t) -$D_1$-perhalo $C_2$-$C_6$ alkyl; or
u) -acid isostere;
wherein
$D_1$ is a direct bond, —S(O)$_2$—, —CON($R_{20}$)—, —$SO_2$N($R_{20}$)—, —C(O)—O—, —S—, or —S(O)—;
wherein $R_{20}$ is -hydrogen, -alkyl, -aryl, -heterocyclyl, or -heteroaryl;
$R_{17}$ is -hydrogen, -alkyl, -aryl, -heterocyclyl, or -heteroaryl;
$R_{18}$ and $R_{19}$ are independently selected from the group consisting of hydrogen, aryl, and alkyl, wherein $R_{18}$ and $R_{19}$ may be taken together to form a ring having the formula —$(CH_2)_o$-$Z_2$-$(CH_2)_p$— bonded to the nitrogen atom to which $R_{18}$ and $R_{19}$ are attached,
wherein
o and p are, independently, 1, 2, 3, or 4 and o +p is less than or equal to 6,
$Z_2$ is a direct bond, —$CH_2$—, —C(O)—, —O—, —N(H)—, —S—, —S(O)—, —S(O)$_2$—, —CON(H)—, —NHC(O)—, —NHC(O)N(H)—, —NH($SO_2$)—, —S(O)$_2$N(H)—, —(O)CO—, —NHS(O)$_2$NH—, —OC(O)—, —N($R_{20}$)—, —N(C(O)$R_{20}$)—, —N(C(O)NH$R_{20}$)—, —N(C(O)N$R_{20}R_{21}$)—, —N(S(O)$_2$NH$R_{20}$)—, —N($SO_2R_{20}$)—, or —N(C(O)O$R_{20}$)—;
wherein
$R_{20}$ and $R_{21}$ are independently selected from the group consisting of -hydrogen, -alkyl, -aryl, and -alkylene-aryl;
$D_2$ is -alkylene-, -alkenylene-, -alkylene-S—, —S-alkylene-, -alkylene-O—, —O—alkylene-, -alkylene-S(O)$_2$—, —S(O)$_2$-alkylene, —O—, —N($R_{22}$)—, —C(O)—, —CON($R_{22}$)—, —N($R_{22}$)C(O)—, —N($R_{22}$)CON($R_{23}$)—, —N($R_{22}$)C(O)O—, —OC(O)N($R_{22}$)—, —N($R_{22}$)$SO_2$—, —$SO_2$N($R_{22}$)—, —C(O)—O—, —O—C(O)—, —S—, —S(O)—, —S(O)$_2$—, or —N($R_{22}$)$SO_2$N($R_{23}$)—,
wherein
$R_{22}$ and $R_{23}$ are independently selected from the group consisting of -hydrogen, -alkyl, and -aryl;
$R_{15}$, $R_{16}$ and $R_{33}$ are independently selected from the group consisting of
a) -hydrogen;
b) -halogen;
c) -cyano;
d) -alkyl;
e) -aryl;
f) -alkylene-aryl;
g) -$D_3$-H;

h) -$D_3$-alkyl;
i) -$D_3$-aryl;
j) -$D_3$-alkylenearyl;
k) -Y-alkyl;
l) -Y-aryl;
m) -Y-alkylene-aryl;
n) -Y-alkylene-$NR_{24}R_{25}$; and
o) -Y-alkylene-W—$R_{26}$;

wherein $D_3$ is —O—, —C(O)—O—, —C(O)—NH—, —$SO_2$—, —$SO_2$—NH—, or —C(O)—;

Y and W are independently selected from the group consisting of —$CH_2$—, —O—, —N(H), —S—, $SO_2$—, —CON(H)—, —NHC(O)—, —NHCON(H)—, —$NHSO_2$—, —$SO_2$N(H)—, —C(O)—O—, —$NHSO_2$NH—, and —O—CO—, $R_{26}$ is aryl, alkyl, alkylene—aryl, alkoxy, or alkoxyaryl;

$R_{24}$ and $R_{25}$ are independently selected from the group consisting of hydrogen, aryl, and alkyl, wherein $R_{24}$ and $R_{25}$ may be taken together to form a ring having the formula —$(CH_2)_o$-$Z_3$-$(CH_2)_p$— bonded to the nitrogen atom to which $R_{24}$ and $R_{25}$ are attached, wherein o and p are, independently, 1, 2, 3, or 4 and o +p is less than or equal to 6, $Z_3$ is a direct bond, —$CH_2$—, —C(O)—, —O—, —N(H)—, —S—, —S(O)—, —$S(O)_2$—, —CON(H)—, —NHC(O)—, —NHC(O)N(H)—, —NH($SO_2$)—, —$S(O)_2$N(H)—, —(O)CO—, —NHS(O)$_2$NH—, —OC(O)—, —N($R_{29}$)—, —N(C(O)$R_{29}$)—, —N(C(O)NH$R_{29}$)—, —N(C(O)NR$_{29}$R$_{30}$)—, —N(S(O)$_2$NHR$_{29}$)—, —N($SO_2R_{29}$)—, or —N(C(O)O$R_{29}$)—;

wherein $R_{29}$ and $R_{30}$ are independently selected from the group consisting of hydrogen, aryl, alkyl, and -alkylaryl;

$R_{26}$ is hydrogen, alkyl, aryl, or alkylene-aryl,

X is sulfur or oxygen; and m and n are independently 0, 1, or 2, or a pharmaceutically acceptable salt thereof, and wherein the compound of Formula (I) is a $GalR_1$ agonist.

45. The compound of Formula (I) in claim 44, or a pharmaceutically acceptable salt thereof, wherein $Ar_3$ is

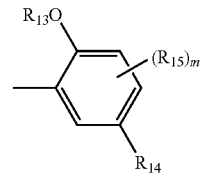

wherein $R_{14}$ is a) -$D_1$-perhalo $C_2$-$C_6$ alkyl;
b) -$D_1$-alkylene-heteroaryl;
c) -$D_1$-alkylene-heterocyclyl;
d) -$D_1$-alkylene-$NR_{18}R_{19}$; or
e) -acid isostere.

46. The compound of Formula (I) in claim 44, or a pharmaceutically acceptable salt thereof, wherein $Ar_3$ is a phenyl group substituted with at least one halo group.

47. The compound of Formula (I) in claim 44, or a pharmaceutically acceptable salt thereof, wherein $Ar_2$ is the group

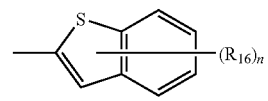

and $Ar_3$ is a phenyl, a benzothiopheneyl, or benzofuranyl group optionally substituted 1 to 5 times, wherein $Ar_2$ and $Ar_3$ are the same or different.

48. The compound of Formula (I) in claim 44, or a pharmaceutically acceptable salt thereof, wherein $Ar_2$ is an unsubstituted benzothiophene group.

49. A pharmaceutical composition comprising the compound of Formula (Ia) as in claim 44, or a pharmaceutically acceptable salt thereof.

50. A pharmaceutical composition comprising the compound of Formula (Ia) as in claim 45, or a pharmaceutically acceptable salt thereof.

51. A pharmaceutical composition comprising the compound of Formula (Ia) as in claim 46, or a pharmaceutically acceptable salt thereof.

52. A pharmaceutical composition comprising the compound of Formula (Ia) as in claim 47, or a pharmaceutically acceptable salt thereof.

53. A pharmaceutical composition comprising the compound of Formula (Ia) as in claim 48, or a pharmaceutically acceptable salt thereof.

* * * * *

UNITED STATES PATENT AND TRADEMARK OFFICE
CERTIFICATE OF CORRECTION

PATENT NO.       : 7,582,673 B2
APPLICATION NO.  : 11/255000
DATED            : September 1, 2009
INVENTOR(S)      : Adnan M. M. Mjalli et al.

It is certified that error appears in the above-identified patent and that said Letters Patent is hereby corrected as shown below:

Page 1, Column 2, under Other Publications, line 1, please delete "Costitutive", please insert -- Constitutive --.

Page 1, Column 2, under Other Publications, line 2, please delete "on", please insert -- of --.

Page 2, Column 1, under Other Publications, line 17, please delete "Pepties", please insert -- Peptides --.

Page 2, Column 2, under Other Publications, line 25, please delete "Distibution", please insert -- Distribution --.

Page 2, Column 2, under Other Publications, line 36, please delete "1.2- and 2.6-", please insert -- 1,2- and 2,6- --.

Page 2, Column 2, under Other Publications, line 52, please delete "Gch", please insert -- Sch --.

Page 2, Column 2, under Other Publications, line 53, please delete "Antagoinist", please insert -- Antagonist --.

Page 2, Column 2, under Other Publications, line 59, please delete "fo", please insert -- of --.

Column 3, line 55, please delete "arrythmias.", please insert -- arrhythmias. --.

Column 4, lines 2-3, please delete "pharmceutically", please insert -- pharmaceutically --.

Column 9, line 14, please delete "-D –alkylene-heteroaryl;", please insert -- -$D_1$-alkylene-heteroaryl; --.

Column 9, line 15, please delete "-D –alkylene-heterocyclyl;", please insert -- -$D_1$-alkylene-heterocyclyl; --.

Column 9, line 43, please delete "-N(C(O)NR$_2$OR$_{21}$)-", please insert -- -N(C(O)NR$_{20}$OR$_{21}$)- --.

UNITED STATES PATENT AND TRADEMARK OFFICE
CERTIFICATE OF CORRECTION

PATENT NO. : 7,582,673 B2
APPLICATION NO. : 11/255000
DATED : September 1, 2009
INVENTOR(S) : Adnan M. M. Mjalli et al.

It is certified that error appears in the above-identified patent and that said Letters Patent is hereby corrected as shown below:

Column 11, line 55 (Approx.), please delete "benzothiopheneyl", please insert -- benzothiophenyl --.

Columns 31-32, line 2 (Table 1), please delete "bis(1", please insert -- bis(1- --.

Column 36, lines 67 (Approx.), please delete "like", please insert -- like. --.

Column 40, line 62, please delete "–$CH_2$–$SO_2$-$CH_2$–", please insert -- –$CH_2$–$SO_2$–$CH_2$–, --.

Column 42, line 59, please delete "-alklylaryl.", please insert -- -alkylaryl. --.

Column 45, line 56 (Approx.), please delete "alchol.", please insert -- alcohol. --.

Column 46, line 17, please delete "injectible", please insert -- injectable --.

Column 46, line 51, please delete "sunstantially", please insert -- substantially --.

Column 47, line 54, please delete "Hydrocloride", please insert -- Hydrochloride --.

Column 48, line 2, please delete "oxlate", please insert -- oxalate --.

Column 48, line 3, please delete "tartarate", please insert -- tartrate --.

Column 49, line 22, please delete "dyslipidimia", please insert -- dyslipidemia --.

Column 50, lines 9-10, please delete "dyslipidimia", please insert -- dyslipidemia --.

Column 50, line 42, please delete "admistered", please insert -- administered --.

Column 51, line 10, please delete "limted", please insert -- limited --.

Column 52, line 2, please delete "administerd", please insert -- administered --.

Column 57, line 44, after "solution" please delete "of".

Column 58, line 26 (Approx.), please delete "$(M+)^+$.", please insert -- $(M+1)^+$. --.

UNITED STATES PATENT AND TRADEMARK OFFICE
CERTIFICATE OF CORRECTION

PATENT NO. : 7,582,673 B2
APPLICATION NO. : 11/255000
DATED : September 1, 2009
INVENTOR(S) : Adnan M. M. Mjalli et al.

It is certified that error appears in the above-identified patent and that said Letters Patent is hereby corrected as shown below:

Column 58, line 53, after "solution", please delete "of".

Column 64, line 11, please delete "(M+1).", please insert -- $(M+1)^+$. --.

Column 64, line 28, please delete "(M+1).", please insert -- $(M+1)^+$. --.

Column 66, line 34, please delete "d6", please insert -- $d_6$ --.

Column 67, line 18, please delete "amino) -5", please insert -- amino)-5 --.

Column 67, line 38, please delete "precipate.", please insert -- precipitate. --.

Column 67, line 55, please delete "amino) -4", please insert -- amino)-4 --.

Column 67, line 57, please delete "(M+1)+", please insert -- $(M+1)^+$. --.

Column 69, line 10, please delete "phosphrous", please insert -- phosphorus --.

Column 71, line 32, after "identical", please delete "the", please insert -- to --.

Column 71, lines 43-44, please delete "sodiumk", please insert -- sodium --.

Column 71, line 56, please delete "filuted", please insert -- diluted --.

Column 74, line 3, in Claim 1, please delete "I)", please insert -- f) --.

Column 74, line 26, in Claim 1, please delete "comprises", please insert -- is --.

Column 75, line 15 (Approx.), in Claim 1, please delete "heteroaryl;", please insert -- -heteroaryl; --.

Column 75, line 34 (Approx.), in Claim 1, please delete "aa)", please insert -- dd) --.

Column 75, line 35 (Approx.), in Claim 1, please delete "bb)", please insert -- ee) --.

Column 76, line 24, in Claim 1, after "substituted", please delete "independently".

UNITED STATES PATENT AND TRADEMARK OFFICE
CERTIFICATE OF CORRECTION

PATENT NO. : 7,582,673 B2
APPLICATION NO. : 11/255000
DATED : September 1, 2009
INVENTOR(S) : Adnan M. M. Mjalli et al.

It is certified that error appears in the above-identified patent and that said Letters Patent is hereby corrected as shown below:

Column 77, line 66, in Claim 3, please delete "—($CH_2$)$_0$-$Z_4$-($CH_2$)$_p$", please insert -- —($CH_2$)$_0$-$Z_4$—($CH_2$)$_p$— --.

Column 78, line 25 (Approx.), in Claim 4, please delete "-$D_4$-alkyl;", please insert -- -$D_4$-alkyl, and --.

Column 79, line 8, in Claim 10, please delete "or", please insert -- and --.

Column 79, line 40 (Approx.), in Claim 11, please delete "-D-heteroaryl;", please insert -- -$D_1$-heteroaryl; --.

Column 80, line 53, in Claim 11, please delete "or", please insert -- and --.

Column 81, line 9, in Claim 12, please delete "thereof", please insert -- thereof, --.

Column 81, line 61, in Claim 15, please delete "benzothiopheneyl", please insert -- benzothiophenyl --.

Column 82, lines 46-47, in Claim 17, below "sulfonamide;", please delete "N-[2-(Benzothiophene-2-sulfonyl)amino]phenylbenzothiophene-2-sulfonamide;".

Column 83, line 6, in Claim 17, please delete "salts", please insert -- salt --.

Column 83, line 10, in Claim 18, please delete "thereof", please insert -- thereof. --.

Column 84, line 39, in Claim 44, below " 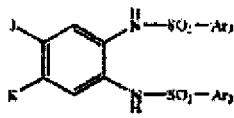 ", please delete "wherein".

Column 86, line 41, in Claim 44, please delete "—N(C(O)NR$_{20}$R$_{21}$ )--", please insert -- —N(C(O)NR$_{20}$R$_{21}$)— --.

Column 87, line 17, in Claim 44, please delete "—S —", please insert -- —S— --.

Column 87, line 23, in Claim 44, please delete "alkylene-aryl", please insert -- alkylenearyl --.

UNITED STATES PATENT AND TRADEMARK OFFICE
CERTIFICATE OF CORRECTION

PATENT NO. : 7,582,673 B2
APPLICATION NO. : 11/255000
DATED : September 1, 2009
INVENTOR(S) : Adnan M. M. Mjalli et al.

It is certified that error appears in the above-identified patent and that said Letters Patent is hereby corrected as shown below:

Column 87, line 57, in Claim 44, please delete "$GalR_1$", please insert -- GalR1 --.

Column 88, line 35 (Approx.), in Claim 47, please delete "benzothiopheneyl", please insert -- benzothiophenyl --.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,582,673 B2 Page 1 of 1
APPLICATION NO. : 11/255000
DATED : September 1, 2009
INVENTOR(S) : Mjalli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 498 days.

Signed and Sealed this

Fourteenth Day of September, 2010

David J. Kappos
*Director of the United States Patent and Trademark Office*